US011028453B2

(12) United States Patent
Atwood et al.

(10) Patent No.: US 11,028,453 B2
(45) Date of Patent: Jun. 8, 2021

(54) QTLS ASSOCIATED WITH AND METHODS FOR IDENTIFYING LODGING RESISTANCE IN SOYBEAN

(71) Applicant: PIONEER HI-BRED INTERNATIONAL, INC., Johnston, IA (US)

(72) Inventors: Sarah Atwood, Ankeny, IA (US); Laura Jean Wolf, Ohio, IL (US); Leslie Charles Kuhlman, Lawrence, KS (US); Donald Earl Kyle, Princeton, IL (US); Daniel Lewis Thomas, Lawrence, KS (US); John Bryan Woodward, Ankeny, IA (US); Ming Yang, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 93 days.

(21) Appl. No.: 16/061,046

(22) PCT Filed: Feb. 10, 2017

(86) PCT No.: PCT/US2017/017326
§ 371 (c)(1),
(2) Date: Jun. 11, 2018

(87) PCT Pub. No.: WO2017/139544
PCT Pub. Date: Aug. 17, 2017

(65) Prior Publication Data

US 2019/0024191 A1 Jan. 24, 2019

Related U.S. Application Data

(60) Provisional application No. 62/293,998, filed on Feb. 11, 2016.

(51) Int. Cl.

| | |
|---|---|
| ***C12Q 1/68*** | (2018.01) |
| ***C12P 19/34*** | (2006.01) |
| ***C12Q 1/6895*** | (2018.01) |
| ***A01H 1/04*** | (2006.01) |
| ***C07K 14/415*** | (2006.01) |
| ***A01H 6/54*** | (2018.01) |
| ***A01H 5/10*** | (2018.01) |
| ***C12Q 1/686*** | (2018.01) |

(52) U.S. Cl.
CPC ............ *C12Q 1/6895* (2013.01); *A01H 1/04* (2013.01); *A01H 5/10* (2013.01); *A01H 6/542* (2018.05); *C07K 14/415* (2013.01); *C12Q 1/686* (2013.01); *C12Q 2600/13* (2013.01); *C12Q 2600/156* (2013.01)

(58) Field of Classification Search
CPC .......... A01H 1/04; A01H 6/542; C12Q 1/686; C12Q 1/6895; C12Q 2600/13; C12Q 2600/156
See application file for complete search history.

(56) References Cited

FOREIGN PATENT DOCUMENTS

CN 103 088 148 A 5/2013

OTHER PUBLICATIONS

Wang, J. et al. "A Bayesian model for detection of highorder interactions among genetic variants in genome-wide association studies". BMC Genomics (2015) 16:1011 (Year: 2015).*
SoyBase Soybean Genetic Map, Chromosome 13, 32622925-38075291, printed from SoyBase.org, pp. 1-9, printed on May 22, 2020 (Year: 2020).*
SoyBase LocusName Satt554, 1 page printed from SoyBase.org on May 22, 2020 (Year: 2020).*
SoyBase LocusName SNP BARC-038503-10136, 1 page printed from SoyBase.org on May 22, 2020 (Year: 2020).*
Lucentini, J. "Gene Association Studies Typically Wrong", The Scientist, p. 20, Dec. 20. (Year: 2004).*
Hegele, R.A. "SNP Judgments and Freedom of Association", Arterioscler Thromb Vasc Biol. 2002;22:1058-1061. (Year: 2002).*
Wall, J.D. et al "Haplotype Blocks and Linkage Disequilibrium in the Human Genome", Nature Reviews—Genetics, vol. 4, August, (Year: 2003).*
Schultz, J.L. et al. D758-D765 Nucleic Acids Research, 2006, vol. 34, Database issue. (Year: 2006).*
Hayward, A.C. et al. "Marker Applications in Plants" Chapter2, pp. 13-27 in Plant Genotyping: Methods and Protocols, edited by Jaqueline Batley, Humana Press (2015) (Year: 2015).*
Lee, Sungwoo, et al: "SNP markers linked to QTL conditioning plant height, lodging and maturity in soybean", Euphytica, Sep. 13, 2014 (Sep. 13, 2014), vol. 203, No. 3, pp. 521-532.
Yamaguchi, Naoya, et al.: "Quantitative trait loci associated with lodging tolerance in soybean cultivar Toyoharuka'", Breeding Science, Jan. 1, 2014 (Jan. 1, 2014), vol. 64, No. 4, pp. 300-308.
International Search Report and Written Opinion, International Application No. PCT/US2017/017326 dated May 30, 2017.

* cited by examiner

*Primary Examiner* — Stephen T Kapushoc

(57) ABSTRACT

The disclosure relates to methods and compositions for identifying and/or selecting soybean plants that have resistance to lodging, have improved resistance to lodging, or are susceptible to lodging. The methods use molecular genetic markers to identify, select and/or construct resistant plants or identify and counter-select susceptible plants. Also provided are soybean plants that display resistance or improved resistance to lodging that are generated by the methods described herein. This abstract is intended as a scanning tool for purposes of searching in the particular art and is not intended to be limiting of the present disclosure.

13 Claims, 9 Drawing Sheets

Specification includes a Sequence Listing.

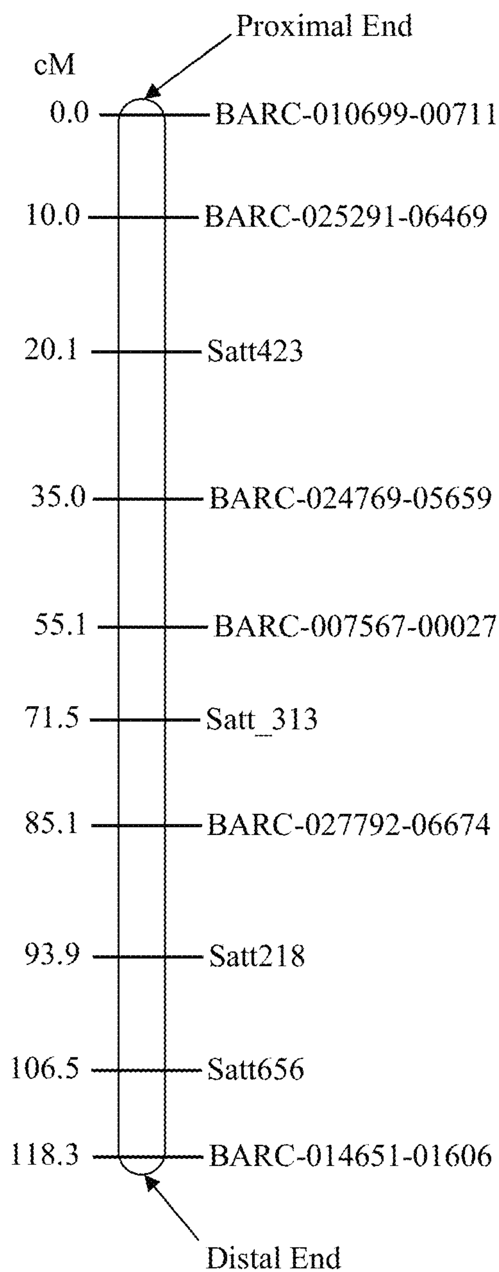
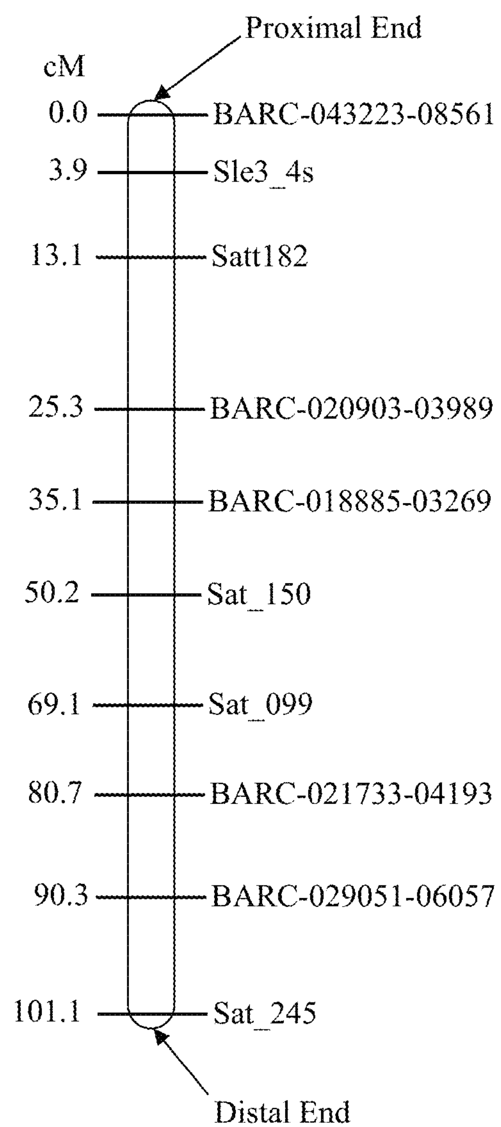
FIGURE 1

| Marker Locus Name | Marker type | Chromosome (Linkage Group) | Position (cM) |
|---|---|---|---|
| BARC-029581-06217 | SNP | 13(F) | 40.041 |
| Bng118_1 | RFLP | 13(F) | 40.07 |
| BARC-014103-01542 | SNP | 13(F) | 40.75 |
| BARC-029167-06103 | SNP | 13(F) | 40.796 |
| Sat_297 | SSR | 13(F) | 43.041 |
| Satt114 | SSR | 13(F) | 43.898 |
| Sat_229 | SSR | 13(F) | 44.08 |
| Mng157_1 | RFLP | 13(F) | 44.411 |
| BARC-050235-09520 | SNP | 13(F) | 44.849 |
| Sat_103 | SSR | 13(F) | 44.911 |
| BARC-050657-09804 | SNP | 13(F) | 45.033 |
| BLT053_7 | RFLP | 13(F) | 46.677 |
| A757_1 | RFLP | 13(F) | 46.727 |
| BARC-024569-04979 | SNP | 13(F) | 48.349 |
| A186_1 | RFLP | 13(F) | 48.838 |
| BARC-025599-06528 | SNP | 13(F) | 49.32 |
| BARC-042681-08346 | SNP | 13(F) | 49.32 |
| BARC-025897-05144 | SNP | 13(F) | 49.424 |
| L063_1 | RFLP | 13(F) | 49.633 |
| Sat_234 | SSR | 13(F) | 49.752 |
| BARC-024569-04982 | SNP | 13(F) | 49.81 |
| BARC-017133-02214 | SNP | 13(F) | 49.876 |
| BARC-007730-00066 | SNP | 13(F) | 49.924 |
| BARC-029983-06769 | SNP | 13(F) | 49.932 |
| BARC-017133-02218 | SNP | 13(F) | 50.103 |
| BARC-008001-00154 | SNP | 13(F) | 50.395 |
| L28831 | RFLP | 13(F) | 50.502 |
| BARC-038413-10074 | SNP | 13(F) | 50.707 |
| Sat_154 | SSR | 13(F) | 51.094 |
| Satt334 | SSR | 13(F) | 51.197 |
| K644_1 | RFLP | 13(F) | 51.411 |
| BARC-031461-07098 | SNP | 13(F) | 51.598 |
| BARC-038411-10073 | SNP | 13(F) | 51.602 |
| BARC-010137-00527 | SNP | 13(F) | 51.666 |
| BARC-065495-19507 | SNP | 13(F) | 51.896 |
| BARC-010279-00576 | SNP | 13(F) | 51.936 |
| Rpg1 | other | 13(F) | 52.069 |

FIGURE 2A

| | | | |
|---|---|---|---|
| BARC-064707-18784 | SNP | 13(F) | 52.218 |
| BARC-007567-00030 | SNP | 13(F) | 52.261 |
| BARC-029823-06439 | SNP | 13(F) | 52.338 |
| BARC-022043-04271 | SNP | 13(F) | 52.389 |
| BARC-042991-08492 | SNP | 13(F) | 52.428 |
| R045_1 | RFLP | 13(F) | 52.627 |
| B212_1 | RFLP | 13(F) | 53.189 |
| BARC-032747-09031 | SNP | 13(F) | 53.202 |
| BARC-041671-08065 | SNP | 13(F) | 53.202 |
| BARC-063863-18477 | SNP | 13(F) | 53.202 |
| BARC-030853-06954 | SNP | 13(F) | 54.078 |
| BARC-047961-10449 | SNP | 13(F) | 54.078 |
| BARC-017917-02451 | SNP | 13(F) | 54.149 |
| BARC-027412-06564 | SNP | 13(F) | 54.374 |
| BARC-042515-08280 | SNP | 13(F) | 54.922 |
| BARC-007567-00027 | SNP | 13(F) | 55.076 |
| BARC-013633-01184 | SNP | 13(F) | 55.317 |
| Satt510 | SSR | 13(F) | 55.596 |
| BARC-060107-16382 | SNP | 13(F) | 55.781 |
| BARC-014579-01586 | SNP | 13(F) | 55.858 |
| BARC-043227-08562 | SNP | 13(F) | 55.989 |
| BARC-015903-02010 | SNP | 13(F) | 56.031 |
| BARC-018521-02929 | SNP | 13(F) | 56.171 |
| BARC-010501-00676 | SNP | 13(F) | 56.243 |
| BARC-044829-08813 | SNP | 13(F) | 56.243 |
| Sct_033 | SSR | 13(F) | 56.466 |
| BARC-030899-06963 | SNP | 13(F) | 56.609 |
| Sat_317 | SSR | 13(F) | 56.891 |
| BARC-029683-06313 | SNP | 13(F) | 56.94 |
| BARC-017917-02456 | SNP | 13(F) | 57.158 |
| BARC-018521-02928 | SNP | 13(F) | 57.409 |
| K007_2 | RFLP | 13(F) | 57.56 |
| BARC-041141-07916 | SNP | 13(F) | 57.817 |
| BARC-059311-15739 | SNP | 13(F) | 57.817 |
| Sat_120 | SSR | 13(F) | 58.425 |
| BARC-048575-10669 | SNP | 13(F) | 58.631 |
| BARC-044877-08831 | SNP | 13(F) | 58.717 |
| BARC-900492-00930 | SNP | 13(F) | 58.878 |
| BARC-018079-02510 | SNP | 13(F) | 60.486 |
| Satt335 | SSR | 13(F) | 61.053 |
| BARC-055499-13329 | SNP | 13(F) | 61.354 |
| A245_1 | RFLP | 13(F) | 62.496 |

FIGURE 2B

| BARC-061189-17109 | SNP | 13(F) | 64.119 |
|---|---|---|---|
| Satt362 | SSR | 13(F) | 64.422 |
| BARC-039631-07532 | SNP | 13(F) | 65.091 |
| BARC-030359-06859 | SNP | 13(F) | 65.095 |
| BARC-013257-00462 | SNP | 13(F) | 65.125 |
| A708_1 | RFLP | 13(F) | 66.497 |
| BARC-038503-10136 | SNP | 13(F) | 66.907 |
| Satt072 | SSR | 13(F) | 68.11 |
| BARC-041649-08056 | SNP | 13(F) | 68.55 |
| BARC-024045-04714 | SNP | 13(F) | 68.704 |
| BARC-039765-07568 | SNP | 13(F) | 68.728 |
| Sct_188 | SSR | 13(F) | 69.123 |
| BARC-047893-10417 | SNP | 13(F) | 69.328 |
| BARC-039135-07450 | SNP | 13(F) | 69.448 |
| Sat_375 | SSR | 13(F) | 69.981 |
| BARC-018605-02982 | SNP | 13(F) | 70.039 |
| BARC-030473-06874 | SNP | 13(F) | 71.024 |
| BARC-027502-06598 | SNP | 13(F) | 71.112 |
| BARC-032717-09021 | SNP | 13(F) | 71.221 |
| BARC-044875-08829 | SNP | 13(F) | 71.259 |
| Sat_313 | SSR | 13(F) | 71.543 |
| BARC-031567-07110 | SNP | 13(F) | 71.893 |
| BARC-045235-08913 | SNP | 13(F) | 71.893 |
| BARC-055229-13122 | SNP | 13(F) | 71.893 |
| Bng190_1 | RFLP | 13(F) | 72.701 |
| BARC-055801-13734 | SNP | 13(F) | 73.652 |
| BARC-042673-08344 | SNP | 13(F) | 73.681 |
| B1 | other | 13(F) | 73.72 |
| BARC-018007-02494 | SNP | 13(F) | 74.033 |
| BARC-052431-11446 | SNP | 13(F) | 74.202 |
| BARC-063121-18247 | SNP | 13(F) | 74.334 |
| BARC-027622-06625 | SNP | 13(F) | 74.541 |
| BARC-007975-00192 | SNP | 13(F) | 74.635 |
| Satt490 | SSR | 13(F) | 74.88 |
| BARC-041127-07909 | SNP | 13(F) | 75.329 |
| BARC-025859-05126 | SNP | 13(F) | 75.44 |
| BARC-041647-08054 | SNP | 13(F) | 75.485 |
| BARC-028583-05961 | SNP | 13(F) | 75.921 |
| BARC-014349-01327 | SNP | 13(F) | 75.947 |
| BARC-018177-02535 | SNP | 13(F) | 75.947 |
| BARC-028887-06033 | SNP | 13(F) | 76.682 |
| BARC-055613-13490 | SNP | 13(F) | 77.164 |

FIGURE 2C

| | | | |
|---|---|---|---|
| Sat_197 | SSR | 13(F) | 77.324 |
| BARC-028887-06034 | SNP | 13(F) | 77.766 |
| BARC-025561-06521 | SNP | 13(F) | 78.335 |
| L195_2 | RFLP | 13(F) | 78.377 |
| Satt144 | SSR | 13(F) | 78.888 |
| BARC-014657-01608 | SNP | 13(F) | 79.425 |
| BARC-039175-07463 | SNP | 13(F) | 80.29 |
| K014_2 | RFLP | 13(F) | 82.094 |
| B148_1 | RFLP | 13(F) | 85.08 |
| BARC-027792-06674 | SNP | 13(F) | 85.177 |
| BARC-046144-10286 | SNP | 13(F) | 85.177 |
| Satt554 | SSR | 13(F) | 87.785 |
| A566_1 | RFLP | 13(F) | 91.086 |
| Satt657 | SSR | 13(F) | 91.393 |
| BARC-061571-17276 | SNP | 13(F) | 91.631 |
| BARC-063309-18328 | SNP | 13(F) | 91.631 |
| Satt522 | SSR | 13(F) | 93.726 |
| Satt218 | SSR | 13(F) | 93.869 |
| BARC-026113-05263 | SNP | 13(F) | 95.847 |
| BARC-038355-10050 | SNP | 13(F) | 96.91 |
| BARC-031367-07070 | SNP | 13(F) | 96.937 |
| AW756935 | SSR | 13(F) | 98.171 |
| BARC-025915-05157 | SNP | 13(F) | 98.455 |
| BARC-013325-00483 | SNP | 13(F) | 99.365 |
| BARC-013325-00484 | SNP | 13(F) | 100.61 |
| BARC-032527-08994 | SNP | 13(F) | 100.61 |
| BARC-042953-08476 | SNP | 13(F) | 102.161 |
| Sat_090 | SSR | 13(F) | 102.946 |
| BARC-015049-02538 | SNP | 13(F) | 103.88 |
| Sat_417 | SSR | 13(F) | 104.844 |
| Satt656 | SSR | 13(F) | 106.553 |
| Bng172_1 | RFLP | 13(F) | 106.842 |
| BARC-018741-02997 | SNP | 13(F) | 107.33 |

FIGURE 2D

| Marker Locus Name | Marker type | Chromosome (Linkage Group) | Position (cM) |
|---|---|---|---|
| BARC-043223-08561 | SNP | 19(L) | 0 |
| BARC-060295-16596 | SNP | 19(L) | 0 |
| BARC-060177-18775 | SNP | 19(L) | 0.091 |
| Sat_408 | SSR | 19(L) | 0.143 |
| A169_1 | RFLP | 19(L) | 0.902 |
| Satt723 | SSR | 19(L) | 1.498 |
| Satt495 | SSR | 19(L) | 2.739 |
| BARC-039375-07304 | SNP | 19(L) | 3.362 |
| BARC-039375-07306 | SNP | 19(L) | 3.735 |
| Sle3_4s | RFLP | 19(L) | 3.946 |
| BLT010_2 | RFLP | 19(L) | 7.133 |
| R176_1 | RFLP | 19(L) | 8.476 |
| BLT007_1 | RFLP | 19(L) | 8.653 |
| Sat_301 | SSR | 19(L) | 9.981 |
| Satt446 | SSR | 19(L) | 10.419 |
| Satt232 | SSR | 19(L) | 12.346 |
| Satt182 | SSR | 19(L) | 13.074 |
| BARC-065445-19463 | SNP | 19(L) | 18.022 |
| Satt238 | SSR | 19(L) | 18.067 |
| BARC-050993-10894 | SNP | 19(L) | 18.162 |
| Sat_071 | SSR | 19(L) | 18.825 |
| BLT039_1 | RFLP | 19(L) | 19.959 |
| Bng071_1 | RFLP | 19(L) | 20.04 |
| Satt388 | SSR | 19(L) | 21.14 |
| B164_1 | RFLP | 19(L) | 24.26 |
| A023_1 | RFLP | 19(L) | 24.683 |
| BARC-020903-03989 | SNP | 19(L) | 25.304 |
| BARC-024499-04939 | SNP | 19(L) | 25.431 |
| Satt523 | SSR | 19(L) | 25.565 |
| BARC-049521-09054 | SNP | 19(L) | 25.823 |
| BARC-049523-09055 | SNP | 19(L) | 25.823 |
| Satt278 | SSR | 19(L) | 25.843 |
| BARC-041643-08051 | SNP | 19(L) | 25.845 |
| BARC-016979-02172 | SNP | 19(L) | 26.109 |
| BARC-023727-03466 | SNP | 19(L) | 26.156 |
| BARC-018215-03169 | SNP | 19(L) | 26.194 |
| i8_2 | RFLP | 19(L) | 26.389 |

FIGURE 3A

| RGA_7 | RFLP | 19(L) | 26.576 |
|---|---|---|---|
| BARC-062745-18897 | SNP | 19(L) | 26.631 |
| BARC-047258-12902 | SNP | 19(L) | 26.633 |
| BARC-055067-12227 | SNP | 19(L) | 26.633 |
| BARC-057559-14826 | SNP | 19(L) | 26.633 |
| BARC-057953-15022 | SNP | 19(L) | 26.633 |
| BARC-062601-17944 | SNP | 19(L) | 26.633 |
| BARC-065415-19444 | SNP | 19(L) | 26.633 |
| BARC-065417-19447 | SNP | 19(L) | 26.633 |
| BARC-050189-09456 | SNP | 19(L) | 26.648 |
| A264_1 | RFLP | 19(L) | 26.852 |
| A204_2 | RFLP | 19(L) | 27.107 |
| A450_2 | RFLP | 19(L) | 27.262 |
| BARC-057829-14944 | SNP | 19(L) | 27.382 |
| A106_1 | RFLP | 19(L) | 27.534 |
| Sat_405 | SSR | 19(L) | 28.049 |
| Satt398 | SSR | 19(L) | 28.291 |
| Satt143 | SSR | 19(L) | 28.405 |
| BARC-058553-15312 | SNP | 19(L) | 28.677 |
| BARC-062231-17720 | SNP | 19(L) | 28.707 |
| Satt418 | SSR | 19(L) | 28.77 |
| B124_2 | RFLP | 19(L) | 29.049 |
| A459_1 | RFLP | 19(L) | 29.154 |
| Sat_195 | SSR | 19(L) | 29.154 |
| Sat_388 | SSR | 19(L) | 29.165 |
| Satt652 | SSR | 19(L) | 29.186 |
| Satt711 | SSR | 19(L) | 29.186 |
| Sat_187 | SSR | 19(L) | 29.191 |
| Satt694 | SSR | 19(L) | 29.193 |
| BARC-065555-19557 | SNP | 19(L) | 29.288 |
| BARC-013093-01432 | SNP | 19(L) | 29.315 |
| BARC-011665-00326 | SNP | 19(L) | 29.317 |
| BARC-011793-00875 | SNP | 19(L) | 29.317 |
| BARC-013895-01264 | SNP | 19(L) | 29.317 |
| Sat_134 | SSR | 19(L) | 29.32 |
| BARC-030043-06786 | SNP | 19(L) | 29.32 |
| BARC-035221-07142 | SNP | 19(L) | 29.32 |
| BARC-047086-12837 | SNP | 19(L) | 29.32 |
| BARC-047144-12870 | SNP | 19(L) | 29.32 |
| BARC-047244-12890 | SNP | 19(L) | 29.32 |
| BARC-047250-12895 | SNP | 19(L) | 29.32 |
| BARC-047428-12928 | SNP | 19(L) | 29.32 |

FIGURE 3B

| | | | |
|---|---|---|---|
| BARC-047933-10435 | SNP | 19(L) | 29.32 |
| BARC-048487-10599 | SNP | 19(L) | 29.32 |
| BARC-049759-09138 | SNP | 19(L) | 29.32 |
| BARC-052985-11687 | SNP | 19(L) | 29.32 |
| BARC-054881-12190 | SNP | 19(L) | 29.32 |
| BARC-055237-13132 | SNP | 19(L) | 29.32 |
| BARC-055799-13726 | SNP | 19(L) | 29.32 |
| BARC-058347-15244 | SNP | 19(L) | 29.32 |
| BARC-058601-15327 | SNP | 19(L) | 29.32 |
| BARC-060631-16759 | SNP | 19(L) | 29.32 |
| BARC-060887-16941 | SNP | 19(L) | 29.32 |
| BARC-061139-17079 | SNP | 19(L) | 29.32 |
| BARC-061163-17087 | SNP | 19(L) | 29.32 |
| BARC-061553-17266 | SNP | 19(L) | 29.32 |
| BARC-065719-19673 | SNP | 19(L) | 29.32 |
| Sat_397 | SSR | 19(L) | 29.4 |
| Sat_320 | SSR | 19(L) | 30.193 |
| Sat_191 | SSR | 19(L) | 30.36 |
| BARC-059443-15806 | SNP | 19(L) | 30.414 |
| Satt497 | SSR | 19(L) | 31.387 |
| G214_17 | RFLP | 19(L) | 31.809 |
| BARC-019365-03897 | SNP | 19(L) | 31.951 |
| Satt313 | SSR | 19(L) | 32.302 |
| BARC-050839-09924 | SNP | 19(L) | 32.607 |
| G214_16 | RFLP | 19(L) | 32.763 |
| BARC-061089-17037 | SNP | 19(L) | 32.773 |
| BARC-040695-07821 | SNP | 19(L) | 33.219 |
| Satt613 | SSR | 19(L) | 33.398 |
| BARC-055761-13695 | SNP | 19(L) | 33.799 |
| Satt284 | SSR | 19(L) | 33.938 |
| BARC-041465-08003 | SNP | 19(L) | 34.003 |
| BARC-064129-18562 | SNP | 19(L) | 34.396 |
| BARC-018885-03269 | SNP | 19(L) | 35.124 |
| BARC-060755-16853 | SNP | 19(L) | 35.3 |
| BARC-020457-04632 | SNP | 19(L) | 35.779 |
| BARC-031583-07115 | SNP | 19(L) | 36.16 |
| BARC-059725-16059 | SNP | 19(L) | 36.357 |
| Satt462 | SSR | 19(L) | 37.177 |
| BARC-022029-04261 | SNP | 19(L) | 37.655 |

FIGURE 3C

QTLS ASSOCIATED WITH AND METHODS FOR IDENTIFYING LODGING RESISTANCE IN SOYBEAN

FIELD

This disclosure relates to compositions and methods for identifying and/or selecting soybean plants or soybean germplasm that have resistance to lodging, have improved resistance to lodging, or are susceptible to lodging, where the methods use molecular genetic markers to identify, select and/or construct plants with lodging resistance. This disclosure also relates to soybean plants and soybean germplasm that display resistance or improved resistance to lodging that are generated by the methods described herein.

REFERENCE TO A SEQUENCE LISTING SUBMITTED AS A TEXT FILE VIA EFS-WEB

The Sequence Listing submitted Feb. 11, 2016 as a text file named "5924USPSP_ST25.txt," created on Jan. 5, 2016, and having a size of 41,000 bytes, is hereby incorporated by reference pursuant to 37 C.F.R. § 1.52(e)(5).

BACKGROUND

Soybean, a legume, has become the world's primary source of seed oil and seed protein. In addition, its utilization is being expanded to the industrial, manufacturing and pharmaceutical sectors. Soybean productivity is a vital agricultural and economic consideration. Thus, a continuing goal of plant breeding is to develop stable, high yielding soybean plants that are agronomically sound in order to maximize the plant yield.

It is the goal of the plant breeder to select plants and enrich the plant population for individuals that have desired traits leading ultimately to increased agricultural productivity. For field crops, these traits may include resistance to diseases and insects, tolerance to heat and drought, reducing time to crop maturity, greater yield, and better agronomic qualities. The mechanical harvesting of many crops has placed increased importance on the uniformity of plant characteristics such as germination, stand establishment, growth rate to maturity, and fruit size. It is important that the plant stalk has good mechanical properties and that the roots are firmly anchored into the soil. During late stages of pod fill it is common for soybean plants to lean over and lodge to the ground as weight from the filling pods increases. Selecting for cultivars that stand erect thru harvest gives the plant an advantage for improved photorespiration, disease resistance, and reduces harvest losses.

SUMMARY

Specific chromosomal loci (or intervals) can be mapped in an organism's genome that correlate with particular quantitative phenotypes. Such loci are termed quantitative trait loci, or QTL. The plant breeder can advantageously use molecular markers to identify desired individuals by identifying marker alleles that show a statistically significant probability of co-segregation with a desired phenotype (e.g., resistance to lodging). By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS).

Despite significant advances in research directed towards soybean plants with traits for improved crop yield, there remains a need in the art for improved soybean strains that are resistant to lodging. There is a need in the art for methods that identify soybean plants or populations (germplasm) that display resistance to lodging. What is needed in the art is to identify molecular genetic markers that are linked to lodging resistance loci in order to facilitate MAS. Such markers can be used to select individual plants and plant populations that show favorable marker alleles in soybean populations and then employed to select the resistance to lodging or decreased lodging phenotype, or alternatively, be used to counterselect plants or plant populations that show a lodging phenotype. The present disclosure provides these and other advantages.

Compositions and methods for identifying soybean plants or germplasm with decreased lodging are provided. Methods of making soybean plants or germplasm that have decreased lodging, e.g., through introgression of desired resistance marker alleles and/or by transgenic production methods, as well as plants and germplasm made by these methods, are also provided. Systems and kits for selecting plants and germplasm with resistance or improved resistance to lodging are also a feature of the disclosure.

Disclosed are methods for identifying and/or selecting a first soybean plant or soybean germplasm (e.g., a line or variety) that has decreased lodging, or susceptibility to lodging. In the methods, at least one allele of one or more marker locus (e.g., a plurality of marker loci) that is associated with the resistance, improved resistance, or susceptibility is detected in the first soybean plant or soybean germplasm.

Also disclosed is a method of selecting a first soybean plant or soybean germplasm that displays improved lodging resistance, the method comprising: (a) detecting in a first soybean plant or soybean germplasm at least one allele of one or more marker locus within or linked to a quantitative trait locus (QTL) associated with improved lodging resistance, wherein the allele positively correlates with improved lodging resistance, and wherein the one or more marker locus localizes within a chromosomal interval from about 67 cM to about 88 cM from the proximal end of chromosome 13; (b) selecting a first soybean plant or soybean germplasm comprising the at least one allele from step (a), thereby selecting a soybean plant or soybean germplasm that displays improved lodging resistance; and (c) crossing the selected first soybean plant or soybean germplasm with a second soybean plant or soybean germplasm to introgress the QTL into a progeny soybean plant or soybean germplasm. In some embodiments, the method further comprises analyzing progeny soybean germplasm to determine the presence of improved lodging resistance and selecting progeny soybean germplasm that test positive for the presence of improved lodging resistance as being soybean germplasm into which germplasm having said QTL has been introgressed.

Also disclosed is a kit for selecting at least one soybean plant by marker assisted selection of a QTL associated with improved lodging resistance comprising: (a) primers or probes for detecting a polymorphism in the soybean genome, wherein the physical position of the polymorphism is: (i) selected from the group consisting of 36,431,456 bp on chromosome 13, 36,490,271 bp on chromosome 13, 36,491,753 bp on chromosome 13, 36,491,754 bp on chromosome 13, 36,492,037 bp on chromosome 13, 36,492,926 bp on chromosome 13, 36,492,955 bp on chromosome 13, 36,493, 615 bp on chromosome 13, 36,494,839 bp on chromosome 13, 36,517,239 bp on chromosome 13, 36,539,789 bp on chromosome 13, 36,539,798 bp on chromosome 13, 36,540, 415 bp on chromosome 13, 36,593,549 bp on chromosome 13, 36,613,902 bp on chromosome 13, 36,644,196 bp on chromosome 13, 36,644,203 bp on chromosome 13, 36,644, 207 bp on chromosome 13, 36,678,427 bp on chromosome 13, 36,697,528 bp on chromosome 13, 36,795,108 bp on chromosome 13, 36,704,369 bp on chromosome 13, 36,300, 296 bp on chromosome 13, 36,567,042 bp on chromosome 13, 36,792,347 bp on chromosome 13, 36,864,280 bp on chromosome 13, 37,443,784 bp on chromosome 13 and a combination thereof; (ii) localized between 36,410 and 36,419 kbp of chromosome 13; or (iii) a combination of (i) and (ii); and (b) instructions for using the primers or probes to detect the marker loci and correlating the loci with predicted improved lodging resistance.

Also disclosed is a method of selecting a first soybean plant or soybean germplasm that displays improved lodging resistance, the method comprising: (a) detecting in a first soybean plant or soybean germplasm at least one allele of one or more marker locus within or linked to a QTL associated with improved lodging resistance, wherein the allele positively correlates with improved lodging resistance, and wherein the one or more marker locus localizes within a chromosomal interval from about 5 cM to about 15 cM from the proximal end of chromosome 19; (b) selecting a first soybean plant or soybean germplasm comprising the at least one allele from step (a), thereby selecting a soybean plant or soybean germplasm that displays improved lodging resistance; and (c) crossing the selected first soybean plant or soybean germplasm with a second soybean plant or soybean germplasm to introgress the QTL into a progeny soybean plant or soybean germplasm. In some embodiments, the method further comprises analyzing progeny soybean germplasm to determine the presence of improved lodging resistance and selecting progeny soybean germplasm that test positive for the presence of improved lodging resistance as being soybean germplasm into which germplasm having said QTL has been introgressed.

Also disclosed is a kit for selecting at least one soybean plant by marker assisted selection of a QTL associated with improved lodging resistance comprising: (a) primers or probes for detecting a polymorphism in the soybean genome, wherein the physical position of the polymorphism is selected from the group consisting of 1,306,591 bp on chromosome 19, 1,635,254 bp on chromosome 19, 841,738 bp on chromosome 19, 1,589,758 bp on chromosome 19 and a combination thereof; and (b) instructions for using the primers or probes to detect the marker loci and correlating the loci with predicted improved lodging resistance.

Also disclosed is a method of selecting a first soybean plant or soybean germplasm that displays improved lodging resistance, the method comprising: (a) detecting in a first soybean plant or soybean germplasm at least one allele of one or more marker locus within or linked to a QTL associated with improved lodging resistance, wherein the allele positively correlates with improved lodging resistance, and wherein the one or more marker locus is selected from the group consisting of: (1) a marker locus localizing within a chromosomal interval flanked by and including marker loci BARO-038503-10136 and Satt554 on chromosome 13; (2) a marker locus localizing within a genetic recombination distance of less than or equal to 5 cM from marker locus Gm13:36704369 on chromosome 13; (3) a marker locus localizing within a genetic recombination distance of less than or equal to 5 cM from marker locus Gm13:36300296 on chromosome 13; and (4) a marker locus localizing within a genetic recombination distance of less than or equal to 5 cM from marker locus Gm13:36593549 on chromosome 13; (b) selecting a first soybean plant or soybean germplasm comprising the at least one allele from step (a), thereby selecting a soybean plant or soybean germplasm that displays improved lodging resistance; and (c) crossing the selected first soybean plant or soybean germplasm with a second soybean plant or soybean germplasm to introgress the QTL into a progeny soybean plant or soybean germplasm. In some embodiments, the method further comprises analyzing progeny soybean germplasm to determine the presence of improved lodging resistance and selecting progeny soybean germplasm that test positive for the presence of improved lodging resistance as being soybean germplasm into which germplasm having said QTL has been introgressed.

Also disclosed is a method of selecting a first soybean plant or soybean germplasm that displays improved lodging resistance, the method comprising: (a) detecting in a first soybean plant or soybean germplasm at least one allele of one or more marker locus within or linked to a QTL associated with improved lodging resistance, wherein the allele positively correlates with improved lodging resistance, and wherein the one or more marker locus is selected from the group consisting of: (1) a marker locus localizing within a chromosomal interval flanked by and including marker loci BARC-039375-07306 and BARC-050993-10894 on chromosome 19; (2) a marker locus localizing within a genetic recombination distance of less than or equal to 5 cM from marker locus Gm19:1306591 on chromosome 19; (3) a marker locus localizing within a genetic recombination distance of less than or equal to 5 cM from marker locus Gm19:1635254 on chromosome 19; (4) a marker locus localizing within a genetic recombination distance of less than or equal to 5 cM from marker locus Gm19:841738 on chromosome 19; and (5) a marker locus localizing within a genetic recombination distance of less than or equal to 5 cM from marker locus Gm19:1589758 on chromosome 19; (b) selecting a first soybean plant or soybean germplasm comprising the at least one allele from step (a), thereby selecting a soybean plant or soybean germplasm that displays improved lodging resistance; and (c) crossing the selected first soybean plant or soybean germplasm with a second soybean plant or soybean germplasm to introgress the QTL into a progeny soybean plant or soybean germplasm. In some embodiments, the method further comprises analyzing progeny soybean germplasm to determine the presence of improved lodging resistance and selecting progeny soybean germplasm that test positive for the presence of improved lodging resistance as being soybean germplasm into which germplasm having said QTL has been introgressed.

Also disclosed are introgressed soybean plants or germplasms produced by the disclosed methods.

BRIEF DESCRIPTION OF THE DRAWINGS

FIG. 1 shows diagrams of the chromosome 13 (left) and chromosome 19 (right) of soybean. The mapping positions of representative marker loci are provided in centiMorgan (cM). The arrows indicate the proximal and distal ends of each chromosome, it being understood that the proximal end is the end of the chromosome closest to and above the marker locus or loci at the 0 cM position based upon Hyten et al., "A High Density Integrated Linkage Map of Soybean and the Development of a 1536 Universal Soy Linkage Panel for Quantitative Trait Locus Mapping" (2010) Crop. Sci. 50:960-968 while the distal end is the end of the chromosome most distal from the marker locus or loci at the 0 cM position.

FIG. 2A illustrates a genetic map comprising a portion of chromosome 13 of soybean and provides a list of marker loci in linkage group F between genetic map positions 40.041 cM and 52.069 cM. Map positions are provided in cM using a genetic map based upon Hyten et al. (2010), and is also available at the USDA affiliated soybean website (www.soybase.org).

FIG. 2B is a continuation of FIG. 2A and illustrates a genetic map comprising a portion of chromosome 13 of soybean and provides a list of marker loci in linkage group F between genetic map positions 52.218 cM and 62.496 cM.

FIG. 2C is a continuation of FIG. 2B and illustrates a genetic map comprising a portion of chromosome 13 of soybean and provides a list of marker loci in linkage group F between genetic map positions 64.119 cM and 77.164 cM.

FIG. 2D is a continuation of FIG. 2C and illustrates a genetic map comprising a portion of chromosome 13 of soybean and provides a list of marker loci in linkage group F between genetic map positions 77.324 cM and 107.33 cM.

FIG. 3A illustrates a genetic map comprising a portion of chromosome 19 of soybean and provides a list of marker loci in linkage group L between genetic map positions 0 cM and 26.389 cM. Map positions are provided in cM using a genetic map based upon Hyten et al. (2010), and is also available at the USDA affiliated soybean website (www.soybase.org).

FIG. 3B is a continuation of FIG. 3A and illustrates a genetic map comprising a portion of chromosome 19 of soybean and provides a list of marker loci in linkage group L between genetic map positions 26.576 cM and 29.32 cM.

FIG. 3C is a continuation of FIG. 3B and illustrates a genetic map comprising a portion of chromosome 19 of soybean and provides a list of marker loci in linkage group L between genetic map positions 29.32 cM and 37.655 cM.

BRIEF DESCRIPTION OF BIOLOGICAL SEQUENCES

Figure 4:
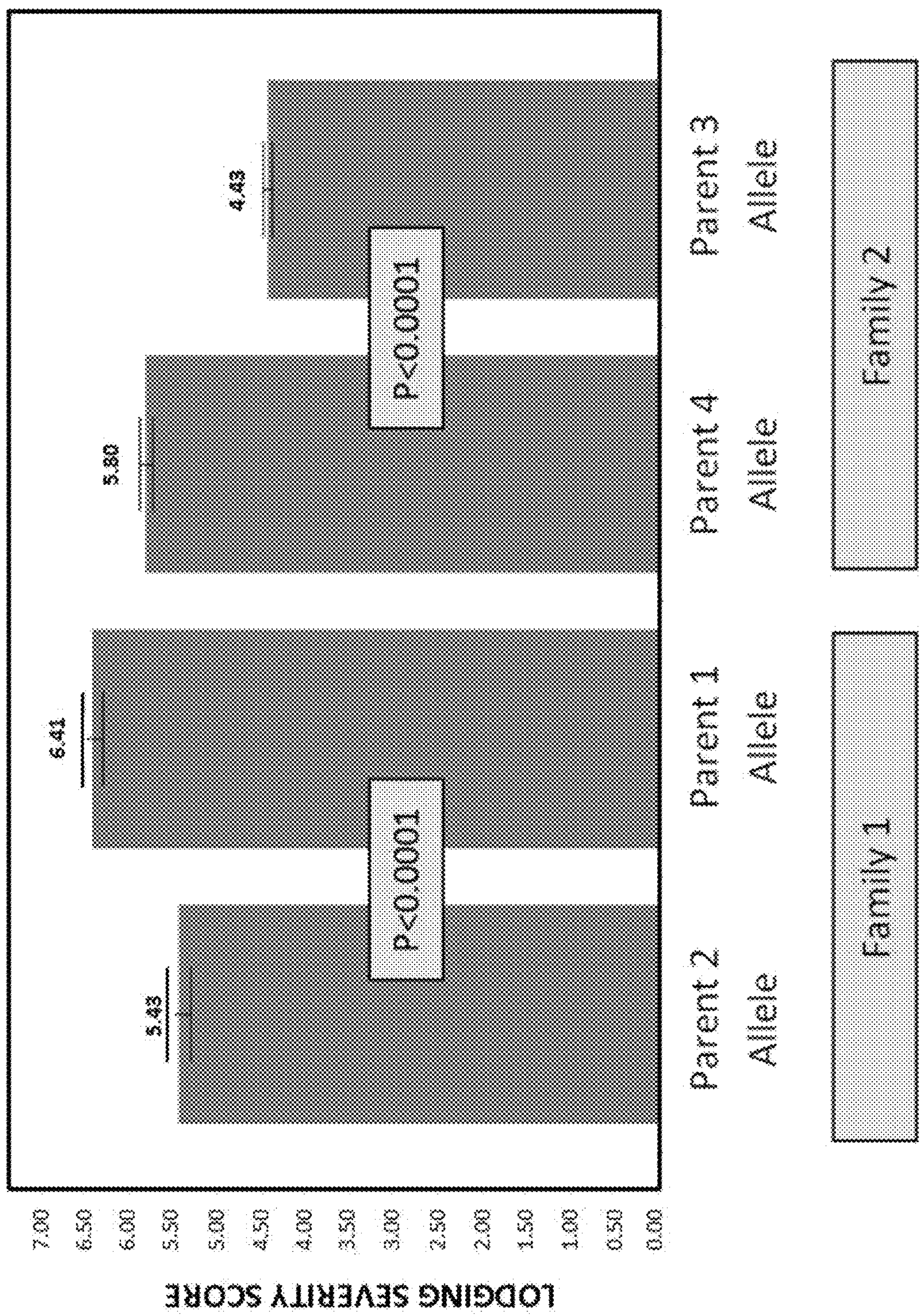
FIG. 4 shows representative data for lodging severity between parental alleles within two families of near isogenic lines ("NILs"). The y-axis depicts lodging severity score.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NOs:1-27 are genomic DNA regions encompassing the marker loci described on Table 1.

SEQ ID NOs: 28-31 are genomic DNA regions encompassing the marker loci described on Table 2.

SEQ ID NOs: 32-35 comprise nucleotide sequences of regions of the soybean genome, each capable of being used as a probe or primer, either alone or in combination, for the detection of a marker locus Gm13:36704369 on chromosome 13 (LG-F). In certain methods, SEQ ID NOs: 32 and 33 are used as primers and SEQ ID NOs: 34 and 35 are used as allele specific probes.

SEQ ID NOs: 36-39 comprise nucleotide sequences of regions of the soybean genome, each capable of being used as a probe or primer, either alone or in combination, for the detection of a marker locus Gm13:36300296 on chromosome 13 (LG-F). In certain methods, SEQ ID NOs: 36 and 37 are used as primers and SEQ ID NOs: 38 and 39 are used as allele specific probes.

SEQ ID NOs: 40-43 comprise nucleotide sequences of regions of the soybean genome, each capable of being used as a probe or primer, either alone or in combination, for the detection of a marker locus Gm13:36567042 on chromosome 13 (LG-F). In certain methods, SEQ ID NOs: 40 and 41 are used as primers and SEQ ID NOs: 42 and 43 are used as allele specific probes.

SEQ ID NOs: 44-47 comprise nucleotide sequences of regions of the soybean genome, each capable of being used as a probe or primer, either alone or in combination, for the detection of a marker locus Gm13:36792347 on chromosome 13 (LG-F). In certain methods, SEQ ID NOs: 44 and 45 are used as primers and SEQ ID NOs: 46 and 47 are used as allele specific probes.

SEQ ID NOs: 48-51 comprise nucleotide sequences of regions of the soybean genome, each capable of being used as a probe or primer, either alone or in combination, for the detection of a marker locus Gm13:36864280 on chromosome 13 (LG-F). In certain methods, SEQ ID NOs: 48 and 49 are used as primers and SEQ ID NOs: 50 and 51 are used as allele specific probes.

SEQ ID NOs: 52-55 comprise nucleotide sequences of regions of the soybean genome, each capable of being used as a probe or primer, either alone or in combination, for the detection of a marker locus Gm13:37443784 on chromosome 13 (LG-F). In certain methods, SEQ ID NOs: 52 and 53 are used as primers and SEQ ID NOs: 54 and 55 are used as allele specific probes.

SEQ ID NOs: 56-59 comprise nucleotide sequences of regions of the soybean genome, each capable of being used as a probe or primer, either alone or in combination, for the detection of a marker locus Gm13:36593549 on chromosome 13 (LG-F). In certain methods, SEQ ID NOs: 56 and 57 are used as primers and SEQ ID NOs: 58 and 59 are used as allele specific probes.

SEQ ID NOs: 60-63 comprise nucleotide sequences of regions of the soybean genome, each capable of being used as a probe or primer, either alone or in combination, for the detection of a marker locus Gm19:1306591 on chromosome 19 (LG-L). In certain methods, SEQ ID NOs: 60 and 61 are used as primers and SEQ ID NOs: 62 and 63 are used as allele specific probes.

SEQ ID NOs: 64-67 comprise nucleotide sequences of regions of the soybean genome, each capable of being used as a probe or primer, either alone or in combination, for the detection of a marker locus Gm19:1635254 on chromosome 19 (LG-L). In certain methods, SEQ ID NOs: 64 and 65 are used as primers and SEQ ID NOs: 66 and 67 are used as allele specific probes.

SEQ ID NOs: 68-71 comprise nucleotide sequences of regions of the soybean genome, each capable of being used as a probe or primer, either alone or in combination, for the detection of a marker locus Gm19:841738 on chromosome 19 (LG-L). In certain methods, SEQ ID NOs: 68 and 69 are used as primers and SEQ ID NOs: 70 and 71 are used as allele specific probes.

SEQ ID NOs: 72-75 comprise nucleotide sequences of regions of the soybean genome, each capable of being used as a probe or primer, either alone or in combination, for the detection of a marker locus Gm19:1589758 on chromosome 19 (LG-L). In certain methods, SEQ ID NOs: 72 and 73 are used as primers and SEQ ID NOs: 74 and 75 are used as allele specific probes.

SEQ ID NO: 76 is the amplicon produced by amplifying genomic DNA using SEQ ID NO: 32 as a forward or reverse primer in conjunction with SEQ ID NO: 33 as the other primer in the pair. This amplicon encompasses marker locus Gm13:36704369 on chromosome 13 (LG-F).

SEQ ID NO: 77 is the amplicon produced by amplifying genomic DNA using SEQ ID NO: 36 as a forward or reverse primer in conjunction with SEQ ID NO: 37 as the other primer in the pair. This amplicon encompasses marker locus Gm13:36300296 on chromosome 13 (LG-F).

SEQ ID NO: 78 is the amplicon produced by amplifying genomic DNA using SEQ ID NO: 40 as a forward or reverse primer in conjunction with SEQ ID NO: 41 as the other primer in the pair. This amplicon encompasses marker locus Gm13:36567042 on chromosome 13 (LG-F).

SEQ ID NO: 79 is the amplicon produced by amplifying genomic DNA using SEQ ID NO: 44 as a forward or reverse primer in conjunction with SEQ ID NO: 45 as the other primer in the pair. This amplicon encompasses marker locus Gm13:36792347 on chromosome 13 (LG-F).

SEQ ID NO: 80 is the amplicon produced by amplifying genomic DNA using SEQ ID NO: 48 as a forward or reverse primer in conjunction with SEQ ID NO: 49 as the other primer in the pair. This amplicon encompasses marker locus Gm13:36864280 on chromosome 13 (LG-F).

SEQ ID NO: 81 is the amplicon produced by amplifying genomic DNA using SEQ ID NO: 52 as a forward or reverse primer in conjunction with SEQ ID NO: 53 as the other primer in the pair. This amplicon encompasses marker locus Gm13:37443784 on chromosome 13 (LG-F).

SEQ ID NO: 82 is the amplicon produced by amplifying genomic DNA using SEQ ID NO: 56 as a forward or reverse primer in conjunction with SEQ ID NO: 57 as the other primer in the pair. This amplicon encompasses marker locus Gm13:36593549 on chromosome 13 (LG-F).

SEQ ID NO: 83 is the amplicon produced by amplifying genomic DNA using SEQ ID NO: 60 as a forward or reverse primer in conjunction with SEQ ID NO: 61 as the other primer in the pair. This amplicon encompasses marker locus Gm19:1306591 on chromosome 19 (LG-L).

SEQ ID NO: 84 is the amplicon produced by amplifying genomic DNA using SEQ ID NO: 64 as a forward or reverse primer in conjunction with SEQ ID NO: 65 as the other primer in the pair. This amplicon encompasses marker locus Gm19:1635254 on chromosome 19 (LG-L).

SEQ ID NO: 85 is the amplicon produced by amplifying genomic DNA using SEQ ID NO: 68 as a forward or reverse primer in conjunction with SEQ ID NO: 69 as the other primer in the pair. This amplicon encompasses marker locus Gm19:841738 on chromosome 19 (LG-L).

SEQ ID NO: 86 is the amplicon produced by amplifying genomic DNA using SEQ ID NO: 72 as a forward or reverse primer in conjunction with SEQ ID NO: 73 as the other primer in the pair. This amplicon encompasses marker locus Gm19:1589758 on chromosome 19 (LG-L).

SEQ ID NO: 87 is the genomic DNA region located from 36,410,000 bp to 36,419,000 by of chromosome 13.

DETAILED DESCRIPTION

The disclosures herein will be described more fully hereinafter with reference to the accompanying drawings, in which some, but not all possible embodiments are shown. Indeed, disclosures may be embodied in many different forms and should not be construed as limited to the embodiments set forth herein; rather, these embodiments are provided so that this disclosure will satisfy applicable legal requirements.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

It is also to be understood that the terminology used herein is for the purpose of describing particular aspects only and is not intended to be limiting. As used in the specification and in the claims, the term "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include embodiments encompassed by the terms "consisting essentially of" and "consisting of." Similarly, the term "consisting essentially of" is intended to include embodiments encompassed by the term "consisting of."

Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

I. Definitions

Before describing the present embodiments in detail, it is to be understood that this disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, the preferred materials and methods are described herein. In order to provide a clear and consistent understanding of the present disclosure and claims, including the scope to be given to such terms, the following definitions apply unless specifically stated otherwise.

A “plant” can be a whole plant, any part thereof, or a cell or tissue culture derived from a plant. Thus, the term “plant” can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term “soybean plant” includes whole soybean plants, soybean plant cells, soybean plant protoplast, soybean plant cell or soybean tissue culture from which soybean plants can be regenerated, soybean plant calli, soybean plant clumps and soybean plant cells that are intact in soybean plants or parts of soybean plants, such as soybean seeds, soybean pods, soybean flowers, soybean cotyledons, soybean leaves, soybean stems, soybean buds, soybean roots, soybean root tips and the like.

“Germplasm” refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

The term “allele” refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A “favorable allele” is the allele at a particular locus that positively correlates with, confers, and/or contributes to, an agronomically desirable phenotype, e.g., resistance to lodging, or alternatively, is an allele that allows the identification of susceptible plants that can be removed from a breeding program or planting. A “favorable allele” of a marker is a marker allele that segregates with the favorable phenotype, or alternatively, segregates with susceptible plant phenotype, therefore providing the benefit of identifying undesirable plants. A favorable allelic form of a chromosome segment is a chromosome segment that includes a nucleotide sequence that contributes to superior agronomic performance at one or more genetic loci physically located on the chromosome segment. “Allele frequency” refers to the frequency (proportion or percentage) at which an allele is present at a locus within an individual, within a line, or within a population of lines. For example, for an allele “A”, diploid individuals of genotype “AA”, “Aa”, or “aa” have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele “positively” correlates with a trait when it is linked to it and when the presence of the allele is an indictor that the desired trait or trait form will occur in a plant comprising the allele. An allele “negatively” correlates with a trait when it is linked to it and when the presence of the allele is an indicator that a desired trait or trait form will not occur in a plant comprising the allele.

An individual is “homozygous” if the individual has only one type of allele at a given locus (e.g., a diploid individual has a copy of the same allele at a locus for each of two homologous chromosomes). An individual is “heterozygous” if more than one allele type is present at a given locus (e.g., a diploid individual with one copy each of two different alleles). The term “homogeneity” indicates that members of a group have the same genotype at one or more specific loci. In contrast, the term “heterogeneity” is used to indicate that individuals within the group differ in genotype at one or more specific loci.

A “locus” is a chromosomal region where a polymorphic nucleic acid, trait determinant, gene or marker is located. Thus, for example, a “gene locus” is a specific chromosome location in the genome of a species where a specific gene can be found.

The term “quantitative trait locus” or “QTL” refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms “marker”, “molecular marker”, “marker nucleic acid”, and “marker locus” refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A “marker probe” is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are “complementary” when they specifically hybridize in solution, e.g., according to Watson-Crick base pairing rules. A “marker locus” is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a “marker allele”, alternatively an “allele of a marker locus”, is one of a plurality of polymorphic nucleotide sequences found at a marker locus in a population that is polymorphic for the marker locus. Any detectable polymorphic trait can be used as a marker so long as it is inherited differentially and exhibits linkage disequilibrium with a phenotypic trait of interest. In some aspects, the present invention provides marker loci correlating with resistance to lodging in soybean. Each of the identified markers is expected to be in close physical and genetic proximity (resulting in physical and/or genetic linkage) to a genetic element, e.g., a QTL that contributes to and is associated with resistance to lodging.

"Genetic marker" or "genetic marker locus" as used herein refers to a type of molecular marker comprised of one or more nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. A "map location" or "map position" is an assigned location on a genetic map relative to linked genetic markers where a specified marker can be found in a given species. Map positions are generally provided in cM, and, unless otherwise indicated, genetic map positions are provided based on the *Glycine max* consensus map v 4.0 as provided by Hyten et al., (2010), which is also available at the USDA affiliated soybase website (www.soybase.org).

A "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "physical position" or "physical location" or "physical map location" is the position, typically in nucleotide bases, of a particular nucleotide, such as a SNP nucleotide, on a chromosome. Unless otherwise indicated, the physical position within the soybean genome provided is based on the Glyma 1.0 genome sequence described in Schmutz et al. (2010) Nature 463:178-183, available from the Phytozome website (http://phytozome.jgi.doe.gov/pz/portal.html).

A "proximal end" of a chromosome refers to the upstream terminus of the chromosome that is closest to and above the marker locus (or loci) having a genetic map location at the 0 cM position on a given chromosome. A "distal end" of a chromosome refers to the mapping position on a genetic map that is most distal from the 0 cM position and indicates the downstream terminus of the chromosome. For example, a chromosomal interval that is between about 50 cM and 60 cM from the proximal end of the chromosome indicates that the chromosomal interval begins at about 50 cM from the 0 cM position and ends at about 60 cM from the 0 cM position on a given genetic map.

A "genetic recombination frequency" is the frequency of a crossing over event (recombination) between two genetic loci. Recombination frequency can be observed by following the segregation of markers and/or traits following meiosis. A genetic recombination frequency can be expressed in cM, where one cM is the distance between two genetic markers that show a 1% recombination frequency (i.e., a crossing-over event occurs between those two markers once in every 100 cell divisions).

As used herein, the term "linkage" or "genetic linkage" is used to describe the degree with which one marker locus is "associated with" another marker locus or some other locus (for example, a resistance locus) based on the frequency of recombination between the loci during meiosis. Loci that are genetically linked are generally located in close proximity along a chromosome and tend to be inherited together. Linkage implies that relevant loci are within sufficient physical proximity along a length of a chromosome that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome.

As used herein, linkage equilibrium describes a situation where two markers have a random association in a population.

As used herein, linkage disequilibrium (LD) describes a situation where two markers have a non-random association in a population, Markers that show linkage disequilibrium are usually genetically linked. As used herein, linkage and LD can be between two markers, or alternatively between a marker and a phenotype. A marker locus can be associated with (linked to and in LD with) a trait, e.g., a marker locus can be associated with resistance or improved resistance to plant lodging when the marker locus is in linkage disequilibrium with the resistance trait. The degree of linkage of a molecular marker to a phenotypic trait is measured, e.g., as a statistical probability of co-segregation of that molecular marker with the phenotype.

The term "associated" or "association" when used in reference to a marker, marker allele, polymorphism and/or QTL and a phenotypic trait refers to any statistically significant correlation between the presence of a given allele of a marker locus and the phenotypic trait, which may be qualitative or quantitative.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "insignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., lodging resistance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15, 14, 13, 12, 11, 10, 9, 8, 7, 6, 5, 4, 3, 2, or 1 cM. In some aspects, it is advantageous to define a bracketed range of linkage, for example, between 1 and 5 cM, between 5 and 10 cM, between 1 and 10 cM, between 10 and 20 cM, between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to resistance and a proximal marker, "coupling" phase linkage indicates the state where the "favorable" allele at the lodging resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present disclosure, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the disclosure is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

As used herein, the term "lodging," "harvest stability," or "LDGSEV" refers to the bending or breakage of the plant stem, or the tilting over of the plant, which complicates harvest and can diminish the value of the harvested product. Lodging severity is scored visually for a plot and is rated using a 1-9 scale representing the percentage of plants in the plot at harvest maturity that were less than fully erect. A score of 1 indicates a plot with almost all plants lying on the ground, a score of 5 indicates that most plants are leaning at a 45° angle in relation to the ground, and a score of 9 indicates a plot with almost all plants fully erect.

It is to be understood that reference to plant "height" or "HGT" herein is a measurement wherein plant height is taken from the top of the soil to the top pod of the plant and is measured in inches.

As used herein, "variety" refers to a substantially homozygous soybean line and minor modifications thereof that retains the overall genetics of the soybean line including but not limited to a subline, a locus conversion, a mutation, a transgenic, or a somaclonal variant. Variety includes seeds, plants, plant parts, and/or seed parts of the instant soybean line.

As used herein, "seed yield" is the actual yield in bushels/acre of the grain at harvest.

As used herein, "inoculum" refers to a pathogen or its parts that can cause infection; that portion of individual pathogens that are brought into contact with the host.

As used herein, "inoculate" refers to bringing a pathogen into contact with a host plant or plant organ.

The term "crossed" or "cross" in the context of this disclosure means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired gene, QTL, haplotype, marker profile, marker locus, marker allele, trait and/or trait locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that is generally inbred to some degree and that are generally homozygous and homogeneous at most loci (isogenic or near isogenic). A "subline" refers to an inbred subset of descendants that is genetically distinct from other similarly inbred subsets descended from the same progenitor. Traditionally, a "subline" has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. In the context of the invention, marker-based sublines, that differ from each other based on qualitative polymorphism at the DNA level at one or more specific marker loci, are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, lodging resistance, herbicide tolerance, etc.).

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and its parents, grand parents, great-grand parents, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

In contrast, an "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "recurrent" plant or "recurrent parent" plant refers to a plant typically having a genetic background with favorable agronomic traits that can be crossed with a soybean plant comprising a desired trait or allele, which is sometimes referred to as a "donor" plant or "donor parent" plant. Backcrossing then enables the breeder to transfer the desired trait or allele from the donor plant into the favored genetic background of the recurrent plant.

The term "amplifying" in the context of nucleic acid amplification is any process whereby an additional copy or copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an expressed sequence tag (EST).

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a “native” or “endogenous” gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term “recombinant” in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference in its entirety.

The term recombinant can also refer to an organism that harbors recombinant material, e.g., a plant that comprises a recombinant nucleic acid is considered a recombinant plant. In some embodiments, a recombinant organism is a transgenic organism.

The term “introduced” when referring to translocating a heterologous or exogenous nucleic acid into a cell refers to the incorporation of the nucleic acid into the cell using any methodology. The term encompasses such nucleic acid introduction methods as “transfection”, “transformation” and “transduction”.

As used herein, the term “vector” is used in reference to polynucleotide or other molecules that transfer nucleic acid segment(s) into a cell. The term “vehicle” is sometimes used interchangeably with “vector”. A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A “cloning vector” or “shuttle vector” or “subcloning vector” contains operably linked parts that facilitate subcloning steps (e.g., a multiple cloning site containing multiple restriction endonuclease sites).

The term “expression vector” as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term “transgenic plant” refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. “Transgenic” is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term “transgenic” as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

A specified nucleic acid is “derived from” a given nucleic acid when it is constructed using the given nucleic acid’s sequence, or when the specified nucleic acid is constructed using the given nucleic acid. For example, a cDNA or EST is derived from an expressed mRNA.

The term “genetic element” or “gene” refers to a heritable sequence of DNA, i.e., a genomic sequence, with functional significance. The term “gene” can also be used to refer to, e.g., a cDNA and/or a mRNA encoded by a genomic sequence, as well as to that genomic sequence.

The term “genotype” is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual’s genetic constitution at a single locus, at multiple loci, or, more generally, the term genotype can be used to refer to an individual’s genetic make-up for all the genes in its genome. A “haplotype” is the genotype of an individual at a plurality of genetic loci. Typically, the genetic loci described by a haplotype are physically and genetically linked, i.e., on the same chromosome segment.

The terms “phenotype”, or “phenotypic trait” or “trait” refers to one or more trait of an organism. The phenotype can be observable to the naked eye, or by any other means of evaluation known in the art, e.g., microscopy, biochemical analysis, genomic analysis, or an assay for a particular disease resistance. In some cases, a phenotype is directly controlled by a single gene or genetic locus, i.e., a “single gene trait”. In other cases, a phenotype is the result of several genes.

A “molecular phenotype” is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

A "set" of markers or probes refers to a collection or group of markers or probes, or the data derived therefrom, used for a common purpose, e.g., identifying soybean plants with a desired trait (e.g., resistance to lodging). Frequently, data corresponding to the markers or probes, or data derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

II. Overview

Provided herein are soybean marker loci that demonstrate statistically significant co-segregation with decreased lodging. Detection of these loci or additional linked loci can be used in marker assisted soybean breeding programs to produce soybean plants or soybean germplasm with resistance or improved resistance to lodging. In certain embodiments, suitable marker loci are provided, including, but not limited to, Gm13:36704369 on chromosome 13 (LG-F), Gm13:36300296 on chromosome 13 (LG-F), Gm13:36593549 on chromosome 13 (LG-F), and/or Gm19:1589758 on chromosome 19 (LG-L).

Each of the marker loci can be visualized as PCR amplicons as described herein. Also provided herein are PCR primer pairs suitable for generating marker loci amplicons, including, but not limited to, oligonucleotides represented by SEQ ID NO: 32 and SEQ ID NO: 33 used to amplify a DNA region flanking Gm13:36704369; SEQ ID NO: 36 and SEQ ID NO: 37 used to amplify a DNA region flanking Gm13:36300296; SEQ ID NO: 56 and SEQ ID NO: 57 used to amplify a DNA region flanking Gm13:36593549; and SEQ ID NO: 72 and SEQ ID NO: 73 used to amplify a DNA region flanking Gm19:1589758. In various further aspects, certain alleles of the various marker loci can be visualized by probes such as the group consisting of SEQ ID NOs: 34, 35, 38, 39, 58, 59, 74, and 75.

The disclosure also provides chromosomal QTL intervals that correlate with decreased lodging located on chromosome 13. Any marker located within these intervals finds use as a marker for decreased lodging. In one aspect, the interval is located at about 67 cM to about 88 cM from the proximal end of chromosome 13. In other aspects, the interval is localized within a chromosomal interval flanked by and included marker loci BARC-038503-10136 and Satt554 on chromosome 13. Alternatively, the interval can be specified as a chromosomal interval located within about 2 Mbp of an interval at 36,410-36,419 kbp of chromosome 13 (SEQ ID NO: 87).

The disclosure also provides chromosomal QTL intervals that correlate with decreased lodging located on chromosome 19. Any marker located within this interval finds use as a marker for decreased lodging. In one aspect, the interval is located at about 5 cM to about 15 cM from the proximal end of chromosome 19. In other aspects, the interval is localized within a chromosomal interval flanked by and included marker loci BARC-039375-07306 and BARC-050993-10894 on chromosome 19. Alternatively, the interval can be specified as a chromosomal interval located within about 2 cM of 1,589,758 bp on chromosome 19. Testing and data demonstrate that a gene responsible for the lodging phenotype is within 2 cM of 1,589,758 bp on chromosome 19.

Methods for identifying soybean plants or germplasm that carry preferred alleles of resistance marker loci are a feature of the disclosure. In these methods, any of a variety of marker detection protocols is used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

In various aspects, disclosed are methods for identifying a first soybean plant or germplasm (e.g., a line or variety) that has improved lodging resistance (i.e., decreased lodging). In the methods, at least one allele of one or more marker locus (e.g., a plurality of marker loci) that is associated with the lodging resistance or improved lodging resistance is detected in the first soybean plant or germplasm. In other aspects, disclosed are methods for identifying a first soybean plant or germplasm (e.g., a line or variety) that displays lodging susceptibility (i.e., increased lodging). In such methods, at least one allele of one or more marker locus (e.g., a plurality of marker loci) that is associated with the susceptibility is detected in the first soybean plant or germplasm.

Also disclosed are methods of identifying and/or selecting a first soybean plant or germplasm that displays improved lodging resistance; the method comprising detecting in the first soybean plan or germplasm at least one allele of one or more marker locus within or linked to a QTL associated with the improved lodging resistance; wherein the marker locus is localized within a chromosomal interval from about 67 cM to about 88 cM from the proximal end of chromosome 13. In other aspects, the marker locus is localizing within a chromosomal interval flanked by and including BARC-038503-10136 and Satt554 on chromosome 13. Alternatively, the marker locus is localized within a chromosomal interval from about 5 cM to about 15 cM from the proximal end of chromosome 19 or a chromosomal interval flanked by and including BARC-039375-07306 and BARC-050993-10894 on chromosome 19.

Also disclosed are methods of identifying and/or selecting a first soybean plant or soybean germplasm that displays improved lodging resistance (i.e., decreased lodging); the method comprising the steps of: (a) detecting in the first soybean plan or soybean germplasm at least one allele of one or more marker locus within or linked to a QTL associated with the improved lodging resistance; wherein the QTL is a chromosomal interval located at about 67 cM to about 88 cM of chromosome 13 or about 5 cM to about 15 cM of chromosome 19; (b) selecting the first soybean plant or germplasm, or selecting a progeny of the first soybean plant or soybean germplasm comprising the at least one allele that is associated with lodging resistance or improved lodging resistance; and (c) crossing the selected first soybean plant or soybean germplasm with a second soybean plant or soybean germplasm to introgress the QTL into progeny soybean germplasm. In other aspects, the QTL is a chromosomal interval flanked by and including BARC-038503-10136 and Satt554 on chromosome 13 or BARC-039375-07306 and BARC-050993-10894 on chromosome 19. In yet other aspects, the marker locus is localized within the chromosomal intervals described herein.

Also disclosed are methods of identifying and/or selecting a first soybean plant or soybean germplasm that displays decreased lodging; the method comprising the steps of: (a) detecting in the first soybean plan or soybean germplasm at least one allele of one or more marker locus within or linked to a QTL associated with improved lodging resistance; wherein the QTL is a chromosomal interval located at about 67 cM to about 88 cM of chromosome 13 or about 5 cM to about 15 cM of chromosome 19; (b) selecting the first soybean plant or soybean germplasm, or selecting a progeny of the first soybean plant or soybean germplasm comprising the at least one allele associated with lodging resistance or improved lodging resistance; (c) crossing the selected first soybean plant or soybean germplasm with a second soybean plant or soybean germplasm to introgress the quantitative trait locus into progeny soybean germplasm; (d) analyzing progeny soybean germplasm to determine the presence of decreased lodging (i.e., resistance or improved resistance to lodging); and (e) selecting progeny soybean germplasm that tests positive for the presence of resistance to lodging as being soybean germplasm into which germplasm having said QTL has been introgressed. In other aspects, the QTL is a chromosomal interval flanked by and including BARC-038503-10136 and Satt554 on chromosome 13 or BARC-039375-07306 and BARC-050993-10894 on chromosome 19. In yet other aspects, the marker locus is localized within the chromosomal intervals described herein.

Although particular marker alleles can show co-segregation with a lodging resistance or susceptibility phenotype, it is important to note that the marker locus is not necessarily part of the QTL locus responsible for the resistance or susceptibility. For example, it is not a requirement that the marker polynucleotide sequence be part of a gene that imparts lodging resistance (for example, be part of the gene open reading frame). The association between a specific marker allele with the resistance or susceptibility phenotype is due to the original "coupling" linkage phase between the marker allele and the QTL resistance or susceptibility allele in the ancestral soybean line from which the resistance or susceptibility allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the genetic marker can be used to monitor segregation of the phenotype. It only changes which marker allele is considered favorable in a given segregating population.

Identification of soybean plants or germplasm that include a marker locus or marker loci linked to a lodging resistance trait or traits provides a basis for performing marker assisted selection of soybean. Soybean plants that comprise markers or marker alleles that are positively correlated with, or favorable for, lodging resistance are selected for, while soybean plants that comprise markers or marker alleles that are negatively correlated with lodging resistance can be selected against. Desired markers, marker alleles, and/or QTLs can be introgressed into soybean having a desired (e.g., elite or exotic) genetic background to produce an introgressed lodging resistant soybean plant or soybean germplasm. In some aspects, it is contemplated that a plurality of resistance markers are sequentially or simultaneous selected and/or introgressed. The combinations of resistance markers that are selected for in a single plant is not limited, and can include any combination of markers recited herein, or any markers located within or linked to the QTL intervals defined herein.

Various methods are known in the art for determining (and measuring) the lodging of a plant. They describe a resistance measurement scale of 1-9, with a score of 1 indicating plants that are lying on the ground, a score of 5 indicates plants are leaning at a 45° angle in relation to the ground, and a score of 9 indicates erect plants. It will be appreciated that all such scales are relative and that numbering and precise correlation to any scale can be performed at the discretion of the practitioner.

Typically, individual field tests are monitored for lodging during the middle to late vegetative stages. Data collection is usually done in one visit at crop Stage R8 (maturity). Soybean crops enter Stage R8 when 95% of the pods are mature and can be readily identified by one having ordinary skill in the art.

In general, while there is a certain amount of subjectivity to assigning severity measurements for lodging, assignment to a given scale as noted above is well within the skill of a practitioner in the field. Measurements can also be averaged across multiple scorers to reduce variation in field measurements.

Lodging resistance assays are useful to verify that the lodging resistance trait still segregates with the marker in any particular plant or population, and, of course, to measure the degree of lodging resistance improvement achieved by introgressing or recombinantly introducing the trait into a desired background.

Systems, including automated systems for selecting plants that comprise a marker and/or marker allele of interest and/or for correlating presence of the marker and/or marker allele with lodging resistance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or marker allele.

Also disclosed are introgressed soybean plants or soybean germplasms produced by the disclosed methods.

Kits are also a feature of the invention. For example, a kit can include appropriate primers or probes for detecting resistance associated marker loci and/or marker alleles and instructions in using the primers or probes for detecting the marker loci and correlating the marker loci or alleles thereof with predicted decreased lodging. The kits can further include packaging materials for packaging the probes, primers or instructions, controls such as control amplification reactions that include probes, primers or template nucleic acids for amplifications, molecular size markers, or the like.

Also disclosed are kits for selecting at least one soybean plant by marker assisted selection of a quantitative trait locus associated with improved lodging resistance comprising: (a) primers or probes for detecting a polymorphism in the soybean genome, wherein the physical position of the polymorphism is (i) selected from the group consisting of 36,431,456 bp on chromosome 13, 36,490,271 bp on chromosome 13, 36,491,753 bp on chromosome 13, 36,491,754 bp on chromosome 13, 36,492,037 bp on chromosome 13, 36,492,926 bp on chromosome 13, 36,492,955 bp on chromosome 13, 36,493,615 bp on chromosome 13, 36,494,839 bp on chromosome 13, 36,517,239 bp on chromosome 13, 36,539,789 bp on chromosome 13, 36,539,798 bp on chromosome 13, 36,540,415 bp on chromosome 13, 36,593,549 bp on chromosome 13, 36,613,902 bp on chromosome 13, 36,644,196 bp on chromosome 13, 36,644,203 bp on chromosome 13, 36,644,207 bp on chromosome 13, 36,678,427 bp on chromosome 13, 36,697,528 bp on chromosome 13, 36,795,108 bp on chromosome 13, 36,704,369 bp on chromosome 13, 36,300,296 bp on chromosome 13, 36,567,042 bp on chromosome 13, 36,792,347 bp on chromosome 13, 36,864,280 bp on chromosome 13, 37,443,784 bp on chromosome 13 and a combination thereof; (ii) localized between 36,410 and 36,419 kbp of chromosome 13; or (iii) a combination of (i) and (ii); and (b) instructions for using the primers or probes to detect the marker loci and correlating the loci with predicted improved lodging resistance.

In various aspects, the primers of the kit comprise a pair of oligonucleotides selected from the group consisting of: (a) SEQ ID NO:32 and SEQ ID NO:33; (b) SEQ ID NO:36 and SEQ ID NO:37; (c) SEQ ID NO:40 and SEQ ID NO:41; (d) SEQ ID NO:44 and SEQ ID NO:45; (e) SEQ ID NO:48 and SEQ ID NO:49; (f) SEQ ID NO:52 and SEQ ID NO:53; (g) SEQ ID NO:56 and SEQ ID NO:57; and (h) a combination thereof.

In various aspects, the probes of the kit comprise an oligonucleotide selected from the group consisting of SEQ ID NOs: 34, 35, 38, 39, 42, 43, 46, 47, 50, 51, 54, 55, 58, and 59, and wherein the oligonucleotide is linked to a detectable label.

Also disclosed are kits for selecting at least one soybean plant by marker assisted selection of a quantitative trait locus associated with improved lodging resistance: (a) primers or probes for detecting a polymorphism in the soybean genome, wherein the physical position of the polymorphism is selected from the group consisting of 1,306,591 bp on chromosome 19, 1,635,254 bp on chromosome 19, 841,738 bp on chromosome 19, 1,589,758 bp on chromosome 19, and a combination thereof; and (b) instructions for using the primers or probes to detect the marker loci and correlating the loci with predicted improved lodging resistance.

In various aspects, the primers of the kit comprise a pair of oligonucleotides selected from the group consisting of: (a) SEQ ID NO:60 and SEQ ID NO:61; (b) SEQ ID NO:64 and SEQ ID NO:65; (c) SEQ ID NO:68 and SEQ ID NO:69; (d) SEQ ID NO:72 and SEQ ID NO:73; and (h) a combination thereof.

In various aspects, the probes of the kit comprise an oligonucleotide selected from the group consisting of SEQ ID NOs: 62, 63, 66, 67, 70, 71, 74, and 75, and wherein the oligonucleotide is linked to a detectable label.

III. Resistance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in soybean, 1 cM correlates, on average, to about 400,000 base pairs (400 Kb).

Marker loci are themselves traits and can be assessed according to standard linkage analysis by tracking the marker loci during segregation. Thus, in the context of the present disclosure, one cM is equal to a 1% chance that a marker locus will be separated from another locus (which can be any other trait, e.g., another marker locus, or another trait locus that encodes a QTL), due to crossing over in a single generation. This means that the markers are sufficiently proximal to a resistance trait that they can be used as a predictor for the lodging resistance trait. This is extremely useful in the context of marker assisted selection (MAS), discussed in more detail herein. In brief, soybean plants or soybean germplasm can be selected for markers or marker alleles that positively correlate with resistance, without actually raising soybean and measuring for resistance or improved resistance (or, contrarily, soybean plants can be selected against if they possess markers that negatively correlate with resistance or improved resistance). MAS is a powerful shortcut to selecting for desired phenotypes and for introgres sing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

A favorable allele of a marker is that allele of the marker that co-segregates with a desired phenotype (e.g., lodging resistance). As used herein, a marker within or linked to a QTL has a minimum of one favorable allele, although it is possible that the marker might have two or more favorable alleles found in the population. Any favorable allele of that marker can be used advantageously for the identification and construction of soybean lines with resistance or improved resistance to lodging. Optionally, one, two, three or more favorable allele(s) of different markers are identified in, or introgressed into a plant, and can be selected for or against during MAS. Desirably, plants or germplasm are identified that have at least one such favorable allele that positively correlates with resistance or improved resistance to lodging.

Alternatively, a marker allele that co-segregates with lodging susceptibility also finds use with the invention, since that allele can be used to identify and counter select susceptible plants. Such an allele can be used for exclusionary purposes during breeding to identify alleles that negatively correlate with resistance, to eliminate susceptible plants or germplasm from subsequent rounds of breeding.

It is therefore an object of this disclosure to provide marker loci and alleles thereof that are suitable for use in the present methods. In a particular aspect, a method of identifying and/or selecting a soybean plant or soybean germplasm that displays improved lodging resistance is provided that includes detecting in a soybean plant or soybean germplasm at least one allele of one or more marker locus within or linked to a QTL associated with improved lodging resistance. In a preferred embodiment, the detected allele positively correlates with improved lodging resistance. In some embodiments, the QTL associated with improved lodging is localized on chromosome 13. In other embodiments, the QTL associated with improved lodging is localized on chromosome 19. In yet other embodiments, the method comprises the detection of multiple marker alleles to enable the detection of a QTL associated with improved lodging resistance on chromosome 13 and a QTL associated with improved lodging resistance on chromosome 19. In some embodiments, marker loci on chromosome 13 of soybean, such as the marker loci provided in Table 1, have been found to positively correlate with decreased lodging in soybean. In other embodiments, marker loci on chromosome 19 of soybean, such as the marker loci provided in Table 2, have been found to positively correlate with decreased lodging in soybean. In still other embodiments, chromosomal intervals, such as the chromosomal intervals located from about 67 cM to about 88 cM of chromosome 13 and/or about 5 cM to about 15 cM of chromosome 19, have been found to positively correlate with decreased lodging in soybean. In certain aspects of this disclosure, the chromosomal interval can be specified as a chromosomal interval located within about 2 Mbp of an interval at 36,410-36,419 kbp of chromosome 13 (SEQ ID NO: 87).

TABLE 1

Non-limiting embodiments of marker loci on chromosome 13 of soybean and suitable for detecting improved lodging resistance.

| Marker Locus | Map Position (cM)* | Physical position (bp)** | Allele (Res/Sus) | Reference Sequence [SNP]† | SEQ ID NO |
|---|---|---|---|---|---|
| Gm13:36704369 | 78.05 | 36,704,369 | C/T | TGCTCAATAATTTTGTCACATAACTGTTCTTGAAT<br>AACTTATGCCTTTTACAAATTCCGTCACATACGA<br>AGTTGTGGCATTTGTGAATTGTGATGAGAAGTGG<br>TAAACCATTGCTCTCTCCTTGCAATACCTTCACTA<br>TTGTGGTTGTTTGGCTTATTTCACTTTTTGAATTG<br>ATRTTGCATATGATTATTTGACATATG**Y**GCTGCTT<br>GCTTGACAAAACTTGCATATGTTTTTGAAATTTTA<br>TTTCATGAGCTAGGGTTTTCCATTGTTTTGAACAA<br>TGTTCATTTGTGTGTACATTTTATTCATTTGGCTT<br>TATTTTACAACACAATATATGAAGAGGATATATG<br>TCAACTAATTTCTAATTGTATATTTCTAATCATTC<br>AGGTTCTTGTGGCGCCAAA | 1 |
| Gm13:36300296 | 77.24 | 36,300,296 | A/C | GATTGGTTACAGAAGGATAGGATTGTATTGTAGT<br>ACTGGGATTTTCTTGTACTTGATCCAAACTTTTTT<br>AAGAAGCTACTTTTATAAATTTCCACCTTTGTTTT<br>GCAGCTAGAGATCTTATTGATACAAAGCACGTGG<br>AAGCAATAATAGGACCCCAAACATGGGAAGAGA<br>CAACTTTGGTGGCTGACATTTGCAGCCAA**M**ACAT<br>GACACCGGTTCTATCTCTAGCTGATGCAACTCCA<br>AACTGGTCAACTTTGAAGTGGCCATTCCTTGTGC<br>AAGCCTCACCTAATCACTTTAAGCAGATGAAAGC<br>AGTAGCAGCTATTGTTCATTCCTTTGGATGGTAC<br>GATGTTAACATAGTTTATGATGATAGGGATTCTT<br>CATCCACAAGAATGTTATCTCATCTC | 2 |
| Gm13:36567042 | 77.72 | 36,567,042 | T/G | ATCTTGAGGTTTCTTCAAACACAATCTGTTGTAA<br>AGTCATTGGTGGTCTTCTCAGCTATTCCACTTTTG<br>GTTCATATTTTCATTGCATAWGCCTTGATTTTCTG | 3 |

TABLE 1-continued

Non-limiting embodiments of marker loci on chromosome 13 of soybean and suitable for detecting improved lodging resistance.

| Marker Locus | Map Position (cM)* | Physical position (bp)** | Allele (Res/ Sus) | Reference Sequence [SNP]† | SEQ ID NO |
|---|---|---|---|---|---|
| | | | | CACAGATYTGAGTTTTATAGGTGCTCCTGTAGCA<br>GTTTCTATTTCATTATGGATATCCATACCATTGTT<br>GGTCATGTATATCATGTATGCAGAAAGKTTCAGG<br>CAGACTTGGACAGGATTTTCATTTGAGTCATTCA<br>ATTACATTTTCACAGACTTGAAACTAGCTTTGCTC<br>TCAGCAGCAATGGTATGGTATGTCTCTAAAAACC<br>TTACACTTAGCTAAACCCCTTTGATGATTGACCTT<br>AGAAAGTTAAATGAAGAGCAGTTTTGTTTGAAAA<br>TCTGTTTTCTGTTTTTCATTCT | |
| Gm13:36792347 | 78.26 | 36,792,347 | A/T | TATGGAATCTAAATTTATTAAATATCATTAATAT<br>GGCATGAATGAAATATATTTCTCATTAATGACAA<br>GACCTTTTATTAAAATATTTATTGCATTACATAAT<br>GTTTTTTTAACGCGTTGTGATCAAAGTCAACATC<br>AATTAAATGGCCACTGCTTTTCAAAAAAAATTAT<br>ATGAACGCTGACGGTTTTACAAACTTATGWGATC<br>TATAGGCGAAGGCTACGGTGAACCACATATTAA<br>GTGGTTCCCAGTAGACCATTATTTCTAACCATAG<br>GATGTATCTTGTTACCATAGTATAGTCCACACTA<br>GATCCATGCACCCTCCCAGCAACTCCCTTATCCA<br>ATTCCTCTGGCCACCATTTGCCGCCACTGGAAGC<br>AATTTTCAGCGGCAGCATTTGTTTTTT | 4 |
| Gm13:36864280 | 78.56 | 36,864,280 | A/G | TCAAGTGTWACTAACCACAATTGGAATGAATAT<br>AAATAATTTGATTATGGTCATATACAAAGATCTA<br>AAGTTATATTTTCAATTTATTCTCCATTTATAATT<br>TCTTAACCTTTACGGAAGCTTCGTAGTTGTTCATA<br>TTACTAATCAAATGCATGTGATCKTGTTTGAGAA<br>ATGTCATTTTTTTTAATTAGTTTAACGTRCGGGTG<br>GTTGGGGGAGGATCATGTATTCATGTTACAAGTT<br>AAAATTTTAATTTTACAATAATCAAATAGTAATC<br>ACTTGCCAATTKATGTTACTATGTGGATTTAAAT<br>GTAAGTATTTAATTTGCTYATGACCAGTACTATA<br>TCATTAGACGTTTGAAAAAAAAAAGTCACAAATT<br>AAAAAAGTATAGAGAATGCTTTAT | 5 |
| Gm13:37443784 | 80.27 | 37,443,784 | G/C | GTTTAATTTTTAAAAAAAAAAACTGCCTCAGATT<br>AAAAAGTGTTTRTTATTGTTCATCTATCTGTAAAT<br>TTTCCGTCGTCTTTGTTAAAAGACAAACCATTAG<br>AGGGTACAATGTTTGTTTTGATCCAAACAAATAT<br>ACGGCAGTTGGCATTGGACGGTACAATTGTTTGT<br>TTTGATCCAAACAAATATATGCAAGTTGGSAGCA<br>CCTCGTGTTACTCATAAGACACAATCGATCGACA<br>GGAGAGATTAATAACCAATTCCATTAATTATTGA<br>ACACAAAGTAATAAATTTTCTTTTTATCCAATAG<br>ATTGATAAATAGTAACAACGTAGAGTAATAACAT<br>ATAACAATCACCTTTTATTATTTATTTTTAAGTTA<br>AAGGCAATATCTTCCATATAAGAGA | 6 |
| Gm13:36593549 | 77.78 | 36,593,549 | C/T | TAAATGAATAAAAAGAGAAAAAAGATRATWTGA<br>AAATAATAATATAAAAATTTAATATAATAWTTAT<br>TTTTCTTGAACGACGTGACATAATTAAAATAACA<br>TTATACTCAAGGGACCGAGCAAGGACATTTTAAC<br>ATTTGTTTCAATGTTTCTACATTTTTCAATGCAAT<br>TGAATGTGATTAGGACAAGATTGGATGGAYGTTA<br>AACTGGGTTTTAAAGGAAGAGAGTCTAAGGTGT<br>GAAACTAAAACRTATTTGTATGGTGTGAAAGGAA<br>AAATAAATTTTYARCAGTTGAATTTATTAATAAA<br>AAAYATAAATGGATGAGATTGATTTTCAATTTTT<br>TATTTTTATTTTTTTCTATTTACTTTTTTTCTTCCTC<br>CCCATTATACCCTTGTACCTTTC | 7 |
| Gm13:36540415 | 77.66 | 36,540,415 | C/T | TAAGGATATTTTGCTTWAAAAAKTAAGGATATTT<br>AATAATTATTTTAAACCGGATTAAGAATTATTGA<br>ATAAAAAAGGTATAACACATTCACTAATGATTYA<br>AGTATAAGACAAATACCTCGCTACATAATAGGA<br>GATACTTGCATAACTCGTGTATCTAATATGGATA<br>CAGCTAGGTATCTATTAATCATGATGGTAATT | 8 |
| Gm13:36490271 | 77.53 | 36,490,271 | T/C | CGTGTTGCATCTCAATGACTTTTTGGCCCAACCCT<br>TTCTTTGCTTTCGGCTTTTGACCATGACCAATATG<br>AAATTACTATATTGCTCTTCAAGTTGTCTTYAACA<br>ATACTCATTAATTTCAAGATATGATTGGTATACT | 9 |

TABLE 1-continued

Non-limiting embodiments of marker loci on chromosome 13 of soybean and suitable for detecting improved lodging resistance.

| Marker Locus | Map Position (cM)* | Physical position (bp)** | Allele (Res/Sus) | Reference Sequence [SNP]† | SEQ ID NO |
|---|---|---|---|---|---|
| | | | | GTTGTGGTTTTCAAGTATATATGTAAATGGGGAT CTAATGTTTTCGTTTGTGTCTCAGAAAG | |
| Gm13:36491753 | 77.54 | 36,491,753 | T/G | GAAATCGTTCAAATACATTTTCATTCAAA TTAACCTAATAATATAATTCAACAAAAA AAAWATCTAACAGCATTAGTGAAGATAT AAGATTGACTGAAGT**K**WAAAAAAACTA AAAAAGAGAAATGTTACATGTTTCATTCG TTCCGTTAACAAAAATTAATAATCTAACA ATTAATATTTCATAATAATAAAAGCCTAA CA | 10 |
| Gm13:36491754 | 77.54 | 36,491,754 | T/A | AAATCGTTCAAATACATTTTCATTCAAATTAACC TAATAATATAATTCAACAAAAAAAAWATCTAAC AGCATTAGTGAAGATATAAGATTGACTGAAGTK **W**AAAAAAACTAAAAAGAGAAATGTTACATGTT TCATTCGTTCCGTTAACAAAAATTAATAATCTAA CAATTAATATTTCATAATAATAAAAGCCTAACAA | 11 |
| Gm13:36492037 | 77.54 | 36,492,037 | T/C | AAAAATTATAAGCATTCATAATTAAGTATTTTTTT TTTCATTCAGTGTTGATGCAAGAGAATAAAAGAT TCCAACCTTTATCTGAATATTATAGTGTACA**Y**GA CATCAAAGGATTCCTTGACAACATTGATGGCAAA AGATTTCTTTAGACAGAAAGTTTTGATAGACATT GATATCATGATATTTCAGATTATTTTCAGC | 12 |
| Gm13:36492926 | 77.54 | 36,492,926 | G/C | AGTTGTGTTTGGAAACTTAGAATAATGAATGCAT CTACCGCACAAAGCCACCATGGGAATACAAGTG AGGCTATCCTAGGATAAAAATGGGTAGGATTGA**S** TAGAATAATATCGTATTTGTATTCATATMCACAT TTAAAAAAAAATATTTGTATCCGATTTCTTATCC GTGTGAATAATAATTTTAATTTTTATTCTTAT | 13 |
| Gm13:36492955 | 77.54 | 36,492,955 | A/C | TGCATCTACCGCACAAAGCCACCATGGGAATACA AGTGAGGCTATCCTAGGATAAAAATGGGTAGGA TTGASTAGAATAATATCGTATTTGTATTCATAT**M** CACATTTAAAAAAAAATATTTGTATCCGATTTCT TATCCGTGTGAATAATAATTTTAATTTTTATTCTT ATATCTATTGAATACTTGTATACTCATATTC | 14 |
| Gm13:36493615 | 77.54 | 36,493,615 | G/A | AAATAATAGGTTAAAAGTTCTAACTCTTCATCCT TTTACATTATTTTATGAGATAATTAATGAAACTAT CTAGCTATAAGAACTAAGAAGCAATGTAATT**R**CA ATACTAATAAAAATGCATAAARCCTTTAATTGGT TTAAATATAGAAAGATCAAATCTTATGAGTACCT TAAAGAATAAATTATACTATTTTTTCTTAT | 15 |
| Gm13:36494839 | 77.55 | 36,494,839 | G/A | CTCAAACTACTTATCTTTTTTATCTTTGTAAGAGT ACTTAATTATCTTTTCAACTTAAATGAGGACCAT AGTTTCGAAACACCTCAATCATCAAGTTGAT**R**CT TTTTTTTATCAAGCAACATTAAGTGAAATTCTATT ACTAAAAAGGAAACTAGCAATGTATTGATCAGTC CTTACTATTGCTTTCTTATTTTGATGGTG | 16 |
| Gm13:36539789 | 77.65 | 36,539,789 | T/A | ATCAATTAAAGCCCCAATTTAAGCAATCCCCATT TCCACTTTTAATAAAAACAACTAAACAAGGTATA TTTTCAAAAGCAGCATCATATACTTGAGAGTG**W** GACATCAAYGAGAGTTGTGCATAAAGTTTCTTAG AAGATATTTCATATGTTTTTGGGGYGGATGACTA AAATTATTCATGTATTTTTGTTGATTACAGAC | 17 |
| Gm13:36539798 | 77.65 | 36,539,798 | T/C | AGCCCCAATTTAAGCAATCCCCATTTCCACTTTTA ATAAAAACAACTAAACAAGGTATATTTTCAAAA GCAGCATCATATACTTGAGAGTGWGACATCAA**Y** GAGAGTTGTGCATAAAGTTTCTTAGAAGATATTT CATATGTTTTTGGGGYGGATGACTAAAATTATTC ATGTATTTTTGTTGATTACAGACRGTATTTAA | 18 |

TABLE 1-continued

Non-limiting embodiments of marker loci on chromosome 13 of soybean and suitable for detecting improved lodging resistance.

| Marker Locus | Map Position (cM)* | Physical position (bp)** | Allele (Res/ Sus) | Reference Sequence [SNP]† | SEQ ID NO |
|---|---|---|---|---|---|
| Gm13:36697528 | 78.04 | 36,697,528 | G/A | AAAAAAAATCAAATTTTTGTCAATATACTTTAAA<br>AATTCAACTATATATCAACTTGAGTAAATGAATC<br>TTGTTGYTATGAAAAAAAAACTAAGGRCATTG**R**T<br>AGCCATGACAACAATGATRATTATGTTAAAAATG<br>ATCATAATAGCGATCACAATGATSRATGATTATA<br>GTAATAATCTTAACATACATCAAATATTTAA | 19 |
| Gm13:36795108 | 78.27 | 36,795,108 | T/C | GAAACATGAAAGCAAATATTATATATTTATAGTA<br>TATTCTATTAGCTACATGTGCATAGATTCTATAG<br>AAGTTATTAAGAACATCTGCTGTGGAAAATAA**Y**G<br>TACCTTGGGTTTGGATATATCATTCTCTTATAAAT<br>TGATATATCTTTGCCAATGTAAATACACCACTTC<br>CCTTCAAAAGAACAGGAACAAAAACGGAAA | 20 |
| Gm13:36431456 | 77.39 | 36,431,456 | A/G | TACTTAGCAAAAATAGGAGGTCCAAATGAGAAA<br>TACCAAATTTAAATGGATACCCAAYCAATATTTG<br>TTTTTTTTTTKTTAAAATATGTTTTTGGTTTTC**R**TG<br>AAAATGTTCAAAATTTATCTCTACAAAATTTTTA<br>GTATATTTTTTGTCCTCACAAATGTGAAATATATA<br>ATTTTTTAGCACAAATGTAGGTTAGGATA | 21 |
| Gm13:36644196 | 77.91 | 36,644,196 | T/C | TACAAAACTGAAATAYTTATCAAAAGGTCTCTST<br>GGTGTGGTGTGGAAATCACTGTCTTSGAAGTAAA<br>ATTTGRYTAAATCTCAATGCAAATTTGAAATG**Y**C<br>AACCRYTTTYCAAGGTTAACACAATRAACCTATT<br>AACGCGCACTCGTGGTCTTAGGCTGCAATTGCCA<br>TTGTCAACACAAGAGGGTTTTGCTTCGGGCA | 22 |
| Gm13:36644203 | 77.91 | 36,644,203 | T/C | CTGAAATAYTTATCAAAAGGTCTCTSTGGTGTGG<br>TGTGGAAATCACTGTCTTSGAAGTAAAATTTGRY<br>TAAATCTCAATGCAAATTTGAAATGYCAACCR**Y**T<br>TTYCAAGGTTAACACAATRAACCTATTAACGCGC<br>ACTCGTGGTCTTAGGCTGCAATTGCCATTGTCAA<br>CACAAGAGGGTTTTGCTTCGGGCACCAGCAT | 23 |
| Gm13:36644207 | 77.91 | 36,644,207 | T/C | AATAYTTATCAAAAGGTCTCTSTGGTGTGGTGTG<br>GAAATCACTGTCTTSGAAGTAAAATTTGRYTAAA<br>TCTCAATGCAAATTTGAAATGYCAACCRYTTT**Y**C<br>AAGGTTAACACAATRAACCTATTAACGCGCACTC<br>GTGGTCTTAGGCTGCAATTGCCATTGTCAACACA<br>AGAGGGTTTTGCTTCGGGCACCAGCATTTGC | 24 |
| Gm13:36517239 | 77.6 | 36,517,239 | A/C | CAATTTTTCATTGCATAAATGATGCTTGGCCACA<br>AATGTAGAACCATTCGTATTATACATCAGCCTGA<br>ATTTTGTATTAATTGCTTGCCTTCTCTTCTGG**M**GA<br>AAAGAATCAGAATGTCCGTAAAGATCTTCACCAA<br>AAAATCATGTCCATCATGTTGAACTGGTTTTGGT<br>CCCCTTGCTCTTCCTTTTATTCTTTCGCTA | 25 |
| Gm13:36678427 | 77.99 | 36,678,427 | A/T | TTTTCAAAAAGTAACGAACACATATTAGTATTTT<br>ATATTTTATTACGATTCTGTTAACAAGTATCTAAA<br>CACATTTAATTTATACTCCCAAAAAGAGTAA**W**A<br>AATTTCGTTCTTATTCATATAACTCAACTATAAGC<br>CGTGTTTGTTACTTGAGTTTGATGTGTCGGTTAAA<br>ATTAAATTATTTTAAAGATAAATAAAATT | 26 |
| Gm13:36613902 | 77.83 | 36,613,902 | T/C | AATGTAATGTAATGTATTTTGCGTTGAGTTTCTCC<br>AAGTTTAAGTTTAAATTACTCTTTAAWTTTTTTT<br>WAAAAAAGAWTTAAATATAGTCGCTGCATTT**Y**C<br>ATCAGTATTGTTCACGAGACATTCCGAGTAACAA<br>AAAATATTTTATTAATGGATAGAGTCTCTTTGAC<br>AAACTTTTTCACARTTATTTATATTAGAAGA | 27 |

*Physical position (bp) on the Glyma 1 Assembly reference (Schmutz et al., 2010).
**Genetic positio (cM) on the Soybean Consensus Map 4.0 (Hyten et al., 2010).
†The position of the SNP within the sequence is indicated in bold and underline.
Res, increased lodging score or increased resistance to lodging.
Sus, decreased lodging score or decreased resistance to lodging.

TABLE 2

Non-limiting embodiments of marker loci on chromosome 19 of soybean and suitable for detecting improved lodging resistance.

| Marker Locus | Map Position (cM)* | Physical position (bp)** | Allele (Res/Sus) | Reference Sequence [SNP]† | SEQ ID NO |
|---|---|---|---|---|---|
| Gm19:1306591 | 7.78 | 1,306,591 | C/T | ATGGCTAAACAACGACAACCCATGCATTCCCAA<br>MTTGTTAACTGAATATCATGCAACTCCGTTAGGT<br>GGTCATCTGGGTGTAGCTAAGACCACCCATCGCA<br>TCGAATCCAATTTCTTCTGGACAAGCCTGAAACA<br>GGATGTTAAACGTTTTGTTAAAGAGTGCTCGACA<br>TGCCAGCAAACTAAGAGTATTACCAGGCGTT**Y**AG<br>CAGGCYTGCTGCAGCCATTGYCACCRCCGACTGG<br>GGTGTGGGAAGACCTCTCAATGGACTTCATCACA<br>CACCTCCCCTTTCCAATGGCTTCACGGTTATACTC<br>RTCGTAGTTGATCGATATTCAAAAGGGRTGCACC<br>TGGGTGCCTTGCCCACTGGTTTCACTGCATTCAA<br>GGTCGCCACCTTGTTCCTGGMCATTA | 28 |
| Gm19:1635254 | 10.43 | 1,635,254 | A/G | GTCTGAGTAGTGGTGACAGTTTTGTAAATACAAC<br>CAACATTTCAACAACGGTTTCCCTGAAAATGTTA<br>TTAAAACCTCAAAACGAAAACGGTTTTCAGGAA<br>AATCATTGTCCTTTTCGAGTATTAAAAGATGGTTT<br>TCGAGTATTCAAACTGTCTTTGAATGAAACCAAT<br>TTTGATGTGAAGGACTTGTGCCCCAGCCCT**R**TCT<br>CACTTCGTTCACTCCGACATGATCAACCTCTTTGC<br>ACCCCTCTCACTTTGTTTGTGTCACTCCGCCTCTG<br>TCAGTGTCGCCATTGTAGCCTGCACCATCGCTCT<br>GTCACCGTTGAAGTCGCCATTGTTGTCATGGGGG<br>TCATGAGGACATATTGTTGTTGTTKCATMTGGTA<br>TGCGTCTATTTCCATTTAATTCGTT | 29 |
| Gm19:841738 | 4.02 | 841,738 | G/A | ATGCAGTGGAAATCACAGGCTTCACCTAGTTAAG<br>TCTCACTATTTTGTTGAAGGAACTGAAGGTCTTTC<br>ATTTGTAGTTCCACAGCTTCTTTCGATAGAGGCTT<br>GAGTTCTGAAACATATTCCTCATCAACTCCTGCT<br>GCTACTTTCTCTGCCTTGTCTTTGACAAGGYGCCG<br>GATCTCTTCGCGCTGAACTGACGGGAA**R**ACAGCA<br>CCGAGCATTGCAGTCAGMAGTCTCTCGTCTTCTT<br>CCTCTATGGAGTCCTTTCCAAAGCAACACACATA<br>GATAGCATCAAGAGCCTTCCCAGCTCGAATCTCC<br>ATTGGGACTGCAGGAGGATCAGCGTTTTGCCTTG<br>CCCGTCTCTACAGTGTTGAATATAATTTTTTTGAG<br>TTGTTAGGGTACTAGGGTAGTGT | 30 |
| Gm19:1589758 | 10.06 | 1,589,758 | G/T | TGCGAGCAACCTTCGAAAYGAGGGAAGTGGTGG<br>CTTGTTATCTTCCACTACTTCTTCAACAATATTGT<br>TATCGTCACCACCACCAATACGAGGTATCGAGTT<br>GGTGGAGCTAGAACGGMTCATCACAACAGAGAG<br>CCTACGGCTACTCGTGTTGTGATTGTCTTTGTTCG<br>ATATGGACGAAGGAGGAGTAGGATGAAAAA**K**GG<br>TGTCTTCTTTTTCATTTTTTGCTTGTTGGAGACGA<br>ACTAGTGAGGTGTAAAGGCCATTGTCGTTTTGGA<br>TTAGTTCATGGTGTGATCCCATCTCCATGATTTTC<br>CCACTTTGCACAACAGCAATCACATTTGCATTCC<br>TTATGGTGGATAATCTATGTGCAATGATGATTGT<br>TGTGCGCCCTACTGCTRCTTTGTCTA | 31 |

*Physical position (bp) on the Glyma 1 Assembly reference (Schmutz et al., 2010).
**Genetic position (cM) on the Soybean Consensus Map 4.0 (Hyten et al., 2010).
†The position of the SNP within the sequence is indicated in bold and underline.
Res, increased lodging score or increased resistance to lodging.
Sus, decreased lodging score or decreased resistance to lodging.

In certain aspects of this disclosure, a method of identifying and/or selecting a soybean plant or soybean germplasm with improved resistance to lodging is provided and comprises detecting in the soybean plant or soybean germplasm at least one allele of one or more marker locus within or linked to a QTL associated improved lodging resistance. In one embodiment, the one or more allele detected is of one or more marker locus localizing on chromosome 13 (LG-F), such as the marker loci provided in FIGS. 2A-2D and Table 1. In some embodiments, the one or more allele detected is of one or more marker locus localizing within a chromosomal interval from about 67 cM to about 88 cM from the proximal end of chromosome 13. FIG. 1 depicts a diagram of chromosome 13 showing the proximal and distal ends in relation to several marker loci. In another embodiment, the one or more allele detected is of one or more marker locus localizing within a chromosomal interval from about 68 cM to about 87 cM from the proximal end of chromosome 13. In yet other embodiments, the one or more allele detected is of one or more marker locus localizing within a chromosomal interval: (i) from about 69 cM to about 86 cM from the proximal end of chromosome 13; (ii) from about 70 cM to about 85 cM from the proximal end of chromosome 13; (iii) from about 75 cM to about 80 cM from the proximal end of chromosome 13; (iv) from about 75.4 cM to about 79.5 cM from the proximal end of chromosome 13; (v) from about 75.9 cM to about 79 cM from the proximal end of chromosome 13; (vi) from about 76.4 cM to about 78.5 cM from the proximal end of chromosome 13; or (vii) from about 76.9 cM to about 78 cM from the proximal end of chromosome 13.

In other aspects, chromosomal intervals are defined by the marker loci flanking either end of the interval. In some embodiments, the one or more allele detected is of one or more marker locus localizing within a chromosomal interval flanked by and including marker loci BARC-038503-10136 and Satt554 on chromosome 13. In another embodiment, the one or more marker locus is localized within a chromosomal interval flanked by and including marker loci Satt072 and BARC-027792-06674 on chromosome 13. In a preferred embodiment, the one or more marker locus is localized within a chromosomal interval flanked by and including marker loci BARC-018605-02982 and BARC-027792-06674 on chromosome 13 or a chromosomal interval flanked by and including marker loci BARC-025859-05126 and BARC-014657-01608 on chromosome 13. In a more preferred embodiment, the one or more marker locus is localized within a chromosomal interval flanked by and including marker loci Gm13:36704369 and Gm13:36300296 on chromosome 13. In yet other embodiments, the one or more marker locus within or linked to the QTL associated with improved lodging resistance is localized within a chromosomal interval flanked by and including marker loci: (i) BARC-028583-05961 and BARC-025561-06521 on chromosome 13; (ii) BARC-028887-06033 and BARC-027792-06674 on chromosome 13; or (iii) BARC-018007-02494 and Satt522 on chromosome 13.

In another embodiment, marker loci suitable for use in the methods provided herein are localized on chromosome 13. In a preferred embodiment, the at least one allele detected is of one or more marker locus selected from the group consisting of Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784 and a combination thereof. In a more preferred embodiment, the at least one allele detected is of one or more marker locus selected from the group consisting of Gm13:36704369, Gm13:36300296, Gm13:36593549, and a combination thereof. In a most preferred aspect, the marker locus is Gm13:36593549.

In some embodiments, the method comprises detecting one or more polymorphisms of and/or linked to one or more marker locus selected from the group consisting of Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784 and a combination thereof.

In further embodiments, the one or more allele detected is of one or more marker locus localizing within one or more of the genomic DNA regions of SEQ ID NOs: 1-27. In some embodiments, the one or more allele detected is of one or more marker locus localizing within 1 cM, 2 cM, 3 cM, 4 cM, 5 cM, 6 cM, 7 cM, 8 cM, 9 cM, 10 cM, 11 cM, 12 cM, 13 cM, 14 cM, 15 cM, 20 cM, or 30 cM of marker locus Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784, or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784, or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from a favorable allele of marker locus Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784, or a combination thereof.

In some aspects, the method comprises detecting one or more polymorphisms having a physical position on chromosome 13 of the soybean genome based on the Glyma 1 Assembly (Schmutz et al., 2010) (see Table 1). In such aspects, the physical position is on chromosome 13 of the soybean genome and selected from the group consisting of 36,431,456 bp on chromosome 13, 36,490,271 bp on chromosome 13, 36,491,753 bp on chromosome 13, 36,491,754 bp on chromosome 13, 36,492,037 bp on chromosome 13, 36,492,926 bp on chromosome 13, 36,492,955 bp on chromosome 13, 36,493,615 bp on chromosome 13, 36,494,839 bp on chromosome 13, 36,517,239 bp on chromosome 13, 36,539,789 bp on chromosome 13, 36,539,798 bp on chromosome 13, 36,540,415 bp on chromosome 13, 36,593,549 bp on chromosome 13, 36,613,902 bp on chromosome 13, 36,644,196 bp on chromosome 13, 36,644,203 bp on chromosome 13, 36,644,207 bp on chromosome 13, 36,678,427 bp on chromosome 13, 36,697,528 bp on chromosome 13, 36,795,108 bp on chromosome 13, 36,704,369 bp on chromosome 13, 36,300,296 bp on chromosome 13, 36,567,042 bp on chromosome 13, 36,792,347 bp on chromosome 13, 36,864,280 bp on chromosome 13, 37,443,784 bp on chromosome 13 and a combination thereof. One skilled in the art will recognize that the physical positions of the polymorphisms (i.e., SNPs) may vary when additional versions of the soybean genomic sequence are published. One skilled in the art will also appreciate that the approximate physical positions of the SNPs in Table 1 are based on a publically available genomic sequence, which may be the same or different as compared to genomic sequence for a particular soybean variety. In either case, the skilled artisan can easily determine the approximate physical positions of the SNPs provided herein on any genomic sequence using sequencing and sequence analysis techniques, such as sequence alignments, BLAST searching, and the like.

Provided herein are alleles that are favorable for, positively correlate with and/or are associated with resistance to lodging. In some embodiments, at least one allele of one or more marker locus positively correlates with improved lodging resistance and is selected from the group consisting of a lodging resistance allele of a marker locus provided in Table 1 and any combination thereof. In other embodiments, at least one allele of one or more marker loci negatively correlates with lodging resistance and is selected from the group consisting of a lodging susceptibility allele of a marker locus provided in Table 1 and any combination thereof. In yet other embodiments, an allele that positively correlates with lodging resistance and an allele that negatively correlates with lodging resistance is detected in a soybean plant or soybean germplasm (i.e., the soybean plant or soybean germplasm is heterozygous).

In some embodiments, alleles that positively correlate with lodging resistance are provided. In one embodiment, the at least one allele that positively correlates with lodging resistance comprises allele A of marker locus Gm13:36431456, allele T of marker locus Gm13:36490271, allele T of marker locus Gm13:36491753, allele T of marker locus Gm13:36491754, allele T of marker locus Gm13:36492037, allele G of marker locus Gm13:36492926, allele A of marker locus Gm13:36492955, allele G of marker locus Gm13:36493615, allele G of marker locus Gm13:36494839, allele A of marker locus Gm13:36517239, allele T of marker locus Gm13:36539789, allele T of marker locus Gm13:36539798, allele C of marker locus Gm13:36540415, allele C of marker locus Gm13:36593549, allele T of marker locus Gm13:36613902, allele T of marker locus Gm13:36644196, allele T of marker locus Gm13:36644203, allele T of marker locus Gm13:36644207, allele A of marker locus Gm13:36678427, allele G of marker locus Gm13:36697528, allele T of marker locus Gm13:36795108, allele C of marker locus Gm13:36704369, allele A of marker locus Gm13:36300296, allele T of marker locus Gm13:36567042, allele A of marker locus Gm13:36792347, allele A of marker locus Gm13:36864280, allele G of marker locus Gm13:37443784, or a combination thereof. In a preferred embodiment, the at least one allele that positively correlates with lodging resistance comprises allele C of marker locus Gm13:36704369, allele A of marker locus Gm13:36300296, allele C of marker locus Gm13:36593549, or a combination thereof.

In another aspect, marker loci suitable for use in the methods provided herein are localized on chromosome 19. In some aspects, a method of identifying and/or selecting a soybean plant or soybean germplasm with improved resistance to lodging is provided and comprises detecting in the soybean plant or soybean germplasm at least one allele of one or more marker locus within or linked to a QTL associated improved lodging resistance. In one embodiment, the one or more allele detected is of one or more marker locus localizing on chromosome 19 (LG-L), such as the marker loci provided in FIGS. 3A-3C and Table 2. In some embodiments, the one or more allele detected is of one or more marker locus localizing within a chromosomal interval from about 5 cM to about 15 cM from the proximal end of chromosome 19. FIG. 1 depicts a diagram of chromosome 19 showing the proximal and distal ends in relation to several marker loci. In another embodiment, the one or more allele detected is of one or more marker locus localizing within a chromosomal interval from about 5.5 cM to about 14.5 cM from the proximal end of chromosome 19. In yet other embodiments, the one or more allele detected is of one or more marker locus localizing within a chromosomal interval: (i) from about 6 cM to about 14 cM from the proximal end of chromosome 19; (ii) from about 7 cM to about 13 cM from the proximal end of chromosome 19; (iii) from about 7.5 cM to about 12.5 cM from the proximal end of chromosome 19; (iv) from about 8 cM to about 12 cM from the proximal end of chromosome 19; (v) from about 8.5 cM to about 11.5 cM from the proximal end of chromosome 19; (vi) from about 9 cM to about 11 cM from the proximal end of chromosome 19; or (vii) from about 9.2 cM to about 10.8 cM from the proximal end of chromosome 19.

In other aspects, chromosomal intervals are defined by the marker loci flanking either end of the interval. In some embodiments, the one or more allele detected is of one or more marker locus localizing within a chromosomal interval flanked by and including marker loci BARC-039375-07306 and BARC-050993-10894 on chromosome 19. In another embodiment, the one or more marker locus is localized within a chromosomal interval flanked by and including marker loci BARC-039375-07306 and Satt182 on chromosome 19. In a preferred embodiment, the one or more marker locus is localized within a chromosomal interval flanked by and including marker loci BARC-039375-07306 and Satt232 on chromosome 19 or a chromosomal interval flanked by and including marker loci Sat_301 and Satt182 on chromosome 19. In a more preferred embodiment, the one or more marker locus is localized within a chromosomal interval flanked by and including marker loci Sat_301 and Satt232 on chromosome 19. In yet other embodiments, the one or more marker locus within or linked to the QTL associated with improved lodging resistance is localized within a chromosomal interval flanked by and including marker loci: (i) BARC-039375-07304 and BARC-065445-19463 on chromosome 19; (ii) R176_1 and Satt182 on chromosome 19; or (iii) Sat_301 and Satt446 on chromosome 19.

In a preferred embodiment, the at least one allele detected is of one or more marker locus selected from the group consisting of Gm19:1306591, Gm19:1635254, Gm19:841738, Gm19:1589758 and a combination thereof. In a more preferred embodiment, the at least one allele detected is of marker locus Gm19:1589758.

In some embodiments, the method comprises detecting one or more polymorphisms of and/or linked to one or more marker locus selected from the group consisting of Gm19:1306591, Gm19:1635254, Gm19:841738, Gm19:1589758 and a combination thereof.

In further embodiments, the one or more allele detected is of one or more marker locus localizing within one or more of the genomic DNA regions of SEQ ID NOs: 28-31. In some embodiments, the one or more allele detected is of one or more marker locus localizing within 1 cM, 2 cM, 3 cM, 4 cM, 5 cM, 6 cM, 7 cM, 8 cM, 9 cM, 10 cM, 11 cM, 12 cM, 13 cM, 14 cM, 15 cM, 20 cM, or 30 cM of marker locus Gm19:1306591, Gm19:1635254, Gm19:841738, Gm19:1589758, or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm19:1306591, Gm19:1635254, Gm19:841738, Gm19:1589758, or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from a favorable allele of marker locus Gm19:1306591, Gm19:1635254, Gm19:841738, Gm19:1589758, or a combination thereof.

In some aspects, the method comprises detecting one or more polymorphisms having a physical position on chromosome 19 of the soybean genome based on the Glyma 1 Assembly (Schmutz et al. 2010) (see Table 2). In such aspects, the physical position is on chromosome 19 of the soybean genome and selected from the group consisting of 1,306,591 bp on chromosome 19, 1,635,254 bp on chromosome 19, 841,738 bp on chromosome 19, 1,589,758 bp on chromosome 19 and a combination thereof. One skilled in the art will recognize that the physical positions of the polymorphisms (i.e., SNPs) may vary when additional versions of the soybean genomic sequence are published. One skilled in the art will also appreciate that the approximate physical positions of the SNPs in Table 2 are based on a publically available genomic sequence, which may be the same or different as compared to genomic sequence for a particular soybean variety. In either case, the skilled artisan can easily determine the approximate physical positions of the SNPs provided herein on any genomic sequence using sequencing and sequence analysis techniques, such as sequence alignments, BLAST searching, and the like.

Provided herein are alleles that are favorable for, positively correlate with and/or are associated with resistance to lodging. In some embodiments, at least one allele of one or more marker locus positively correlates with improved lodging resistance and is selected from the group consisting of a lodging resistance allele of a marker locus provided in Table 2 and any combination thereof. In other embodiments, at least one allele of one or more marker loci negatively correlates with lodging resistance and is selected from the group consisting of a lodging susceptibility allele of a marker locus provided in Table 2 and any combination thereof. In yet other embodiments, an allele that positively correlates with lodging resistance and an allele that negatively correlates with lodging resistance is detected in a soybean plant or soybean germplasm (i.e., the soybean plant or soybean germplasm is heterozygous).

In some embodiments, alleles that positively correlate with lodging resistance are provided. In one embodiment, the at least one allele that positively correlates with lodging resistance comprises allele C of marker locus Gm19:1306591, allele A of marker locus Gm19:1635254, allele G of marker locus Gm19:841738, allele G of marker locus Gm19:1589758 or a combination thereof. In a preferred embodiment, the at least one allele that positively correlates with lodging resistance comprises allele G of marker locus Gm19:1589758.

In some embodiments of the disclosure, a plurality of marker alleles are simultaneously selected for in a single plant or a population of plants. In these methods, plants are selected that contain favorable alleles from more than one resistance marker, or alternatively, favorable alleles from more than one resistance marker are introgressed into a desired soybean germplasm. One of skill in the art recognizes that the simultaneous selection of favorable alleles from more than one resistance marker in the same plant is likely to result in an additive (or even synergistic) protective effect for the plant.

One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are routine and well known in the art, and furthermore, that the identification and use of such favorable alleles is well within the scope of the methods provided herein. Furthermore still, identification of favorable marker alleles in soybean populations other than the populations used or described herein is well within the scope of method provided herein.

In some aspects, at least one allele of one or more marker locus within or linked to a QTL associated with improved resistance to lodging can be detected using one of the detection techniques described elsewhere herein. In certain aspects, the detection technique comprises amplification, e.g., via polymerase chain reaction (PCR), of a genomic DNA region encompassing the marker locus. In a preferred embodiment, the one or more marker locus is localized on chromosome 13 of soybean and selected from the group consisting of a marker locus described in Table 1 and a combination thereof. In such an embodiment, the detection step comprises PCR detection using amplification primers for amplifying at least a portion of one or more genomic DNA regions of the soybean genome having at least 80%, 81%, 82%, 83%, 84%, 85%, 86%, 87%, 88%, 89%, 90%, 91%, 92%, 93%, 94%, 95%, 96%, 97%, 98%, or 99% or 100% sequence identity to the nucleic acid sequence selected from the group consisting of SEQ ID NOs: 1-27. In a more preferred embodiment, the one or more marker locus is selected from the group consisting of Gm13:36704369, Gm13:36300296, Gm13:36567042, Gm13:36792347, Gm13:36864280, Gm13:37443784, Gm13:36593549, and any combination thereof. In such an embodiment, the detection step comprises PCR detection using amplification primers for amplifying at least a portion of one or more genomic DNA regions of the soybean genome having at least 80%, 81%, 82%, 83%, 84%, 85%, 86%, 87%, 88%, 89%, 90%, 91%, 92%, 93%, 94%, 95%, 96%, 97%, 98%, or 99% or 100% sequence identity to the nucleic acid sequence selected from the group consisting of SEQ ID 1, 2, 3, 4, 5, 6, and 7 using oligonucleotide primers comprising a nucleic acid sequence selected from the group consisting of SEQ ID NOs: 32, 33, 36, 37, 40, 41, 44, 45, 48, 49, 52, 53, 56, and 57. Exemplary amplicons produced by such a PCR amplification technique comprise at least a portion of a genomic DNA region of the soybean genome having a nucleic acid sequence represented by SEQ ID NOs: 76, 77, 78, 79, 80, 81, or 82. In some aspects, the amplification step further includes the use of allele-specific probes capable of hybridizing to a specific allele of the marker locus. For example, one or more probes comprising a nucleic acid sequence selected from the group consisting of SEQ ID NOs: 34, 35, 38, 39, 42, 43, 46, 47, 50, 51, 54, 55, 58, and 59 can be used in the present methods for detecting an allele of the marker locus associated with improved resistance to lodging. Exemplary primers and probes are provided in Table 3.

In another embodiment, the one or more marker locus is localized on chromosome 19 of soybean and selected from the group consisting of a marker locus described in Table 2 and a combination thereof. In such an embodiment, the detection step comprises PCR detection using amplification primers for amplifying at least a portion of one or more genomic DNA regions of the soybean genome having at least 80%, 81%, 82%, 83%, 84%, 85%, 86%, 87%, 88%, 89%, 90%, 91%, 92%, 93%, 94%, 95%, 96%, 97%, 98%, or 99% or 100% sequence identity to the nucleic acid sequence selected from the group consisting of SEQ ID NOs: 28-31. In a more preferred embodiment, the one or more marker locus is selected from the group consisting of Gm19: 1306591, Gm19:1635254, Gm19:841738, Gm19:1589758, and any combination thereof. In such an embodiment, the detection step comprises PCR detection using amplification primers for amplifying at least a portion of one or more genomic DNA regions of the soybean genome having at least 80%, 81%, 82%, 83%, 84%, 85%, 86%, 87%, 88%, 89%, 90%, 91%, 92%, 93%, 94%, 95%, 96%, 97%, 98%, or 99% or 100% sequence identity to the nucleic acid sequence selected from the group consisting of SEQ ID 28, 29, 30 and 31 using oligonucleotide primers comprising a nucleic acid sequence selected from the group consisting of SEQ ID NOs: 60, 61, 64, 65, 68, 69, 72, and 73. Exemplary amplicons produced by such a PCR amplification technique comprise at least a portion of a genomic DNA region of the soybean genome having a nucleic acid sequence represented by SEQ ID NOs: 83, 84, 85, or 86. In some aspects, the amplification step further includes the use of allele-specific probes capable of hybridizing to a specific allele of the marker locus. For example, one or more probes comprising a nucleic acid sequence selected from the group consisting of SEQ ID NOs: 62, 63, 66, 67, 70, 71, 74, and 75 can be used in the present methods for detecting an allele of the marker locus associated with improved resistance to lodging. Exemplary primers and probes are provided in Table 3.

TABLE 3

Non-limiting list of suitable primers and probes for the detection of various marker loci of the present disclosure.

| Marker Name | Linkage Group/ Chrom. No. | Relative Map Position (cM) | Approximate Physical Position of SNP (bp) | SEQ ID | Primer or Probe |
|---|---|---|---|---|---|
| Gm13: 36704369 | F/13 | 78.05 | 36,704,369 | 32 | Primer |
| | | | | 33 | Primer |
| | | | | 34 | Allelic Probe |
| | | | | 35 | Allelic Probe |
| Gm13: 36300296 | F/13 | 77.24 | 36,300,296 | 36 | Primer |
| | | | | 37 | Primer |
| | | | | 38 | Allelic Probe |
| | | | | 39 | Allelic Probe |
| Gm13: 36567042 | F/13 | 77.72 | 36,567,042 | 40 | Primer |
| | | | | 41 | Primer |
| | | | | 42 | Allelic Probe |
| | | | | 43 | Allelic Probe |
| Gm13: 36792347 | F/13 | 78.26 | 36,792,347 | 44 | Primer |
| | | | | 45 | Primer |
| | | | | 46 | Allelic Probe |
| | | | | 47 | Allelic Probe |
| Gm13: 36864280 | F/13 | 78.56 | 36,864,280 | 48 | Primer |
| | | | | 49 | Primer |
| | | | | 50 | Allelic Probe |
| | | | | 51 | Allelic Probe |
| Gm13: 37443784 | F/13 | 80.27 | 37,443,784 | 52 | Primer |
| | | | | 53 | Primer |
| | | | | 54 | Allelic Probe |
| | | | | 55 | Allelic Probe |
| Gm13: 36593549 | F/13 | 77.78 | 36,593,549 | 56 | Primer |
| | | | | 57 | Primer |
| | | | | 58 | Allelic Probe |
| | | | | 59 | Allelic Probe |
| Gm19: 1306591 | L/19 | 7.78 | 1,306,591 | 60 | Primer |
| | | | | 61 | Primer |
| | | | | 62 | Allelic Probe |
| | | | | 63 | Allelic Probe |

TABLE 3-continued

Non-limiting list of suitable primers and probes for the detection of various marker loci of the present disclosure.

| Marker Name | Linkage Group/ Chrom. No. | Relative Map Position (cM) | Approximate Physical Position of SNP (bp) | SEQ ID | Primer or Probe |
|---|---|---|---|---|---|
| Gm19: 1635254 | L/19 | 10.43 | 1,635,254 | 64 | Primer |
| | | | | 65 | Primer |
| | | | | 66 | Allelic Probe |
| | | | | 67 | Allelic Probe |
| Gm19: 841738 | L/19 | 4.02 | 841,738 | 68 | Primer |
| | | | | 69 | Primer |
| | | | | 70 | Allelic Probe |
| | | | | 71 | Allelic Probe |
| Gm19: 1589758 | L/19 | 10.06 | 1,589,758 | 72 | Primer |
| | | | | 73 | Primer |
| | | | | 74 | Allelic Probe |
| | | | | 75 | Allelic Probe |

In addition to the non-limiting list of exemplary primers and probes described in Table 3, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook, et al., (2000) Molecular Cloning—A Laboratory Manual (3rd Ed.), Vol. 1-3, Cold Spring Harbor Laboratory, Cold Spring Harbor, N.Y., ("Sambrook"); Current Protocols in Molecular Biology, Ausubel, et al., eds., Current Protocols, a joint venture between Greene Publishing Associates, Inc. and John Wiley & Sons, Inc., (supplemented through 2002) ("Ausubel") and PCR Protocols A Guide to Methods and Applications (Innis, et al., eds) Academic Press Inc. San Diego, Calif. (1990) (Innis). Additional details regarding detection of nucleic acids in plants can also be found, e.g., in Plant Molecular Biology (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. Any of the aforementioned marker types can be employed in the context of the invention to identify chromosome segments encompassing genetic element that contribute to superior agronomic performance (e.g., resistance or improved resistance to lodging).

IV. QTL Chromosome Intervals

In some aspects, the invention provides QTL chromosome intervals, where a QTL (or multiple QTLs) that segregate with decreased lodging are contained in those intervals. A variety of methods well known in the art are available for identifying chromosome intervals, including those methods described herein. The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for lodging resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the method described herein.

The present disclosure provides a soybean chromosome interval, where the markers within that interval demonstrate co-segregation with decreased lodging. Thus, this interval comprises at least one decreased lodging QTL. In one embodiment, the interval is a chromosomal interval located at about 67 cM to about 88 cM from the proximal end of chromosome 13. In other embodiments, the interval is a chromosomal interval localizing: (i) from about 68 cM to about 87 cM from the proximal end of chromosome 13; (ii) from about 69 cM to about 86 cM from the proximal end of chromosome 13; (iii) from about 70 cM to about 85 cM from the proximal end of chromosome 13; (iv) from about 75 cM to about 80 cM from the proximal end of chromosome 13; (v) from about 75.4 cM to about 79.5 cM from the proximal end of chromosome 13; (vi) from about 75.9 cM to about 79 cM from the proximal end of chromosome 13; (vii) from about 76.4 cM to about 78.5 cM from the proximal end of chromosome 13; or (viii) from about 76.9 cM to about 78 cM from the proximal end of chromosome 13. Alternatively, this interval can be specified as a chromosomal interval located within about 2 million base pairs (Mbp), e.g., 1.75 Mbp, 1.5 Mbp, 1.25 Mbp, 1 Mbp, 750 kbp, 500 kbp, 250 kbp, 1,000 bp, 900 bp, 800 bp, 700 bp, 600 bp, 500 bp, 400 bp, 300 bp, 200 bp, 100 bp or less of an interval at 36,410-36,419 kbp of chromosome 13 (SEQ ID NO:87).

In another aspect, the interval is a chromosomal interval located at about 5 cM to about 15 cM from the proximal end of chromosome 19. In other embodiments, the interval is a chromosomal interval localizing: (i) from about 5 cM to about 15 cM from the proximal end of chromosome 19; (ii) from about 5.5 cM to about 14.5 cM from the proximal end of chromosome 19; (iii) from about 6 cM to about 14 cM from the proximal end of chromosome 19; (iv) from about 7 cM to about 13 cM from the proximal end of chromosome 19; (v) from about 7.5 cM to about 12.5 cM from the proximal end of chromosome 19; (v) from about 8 cM to about 12 cM from the proximal end of chromosome 19; (vii) from about 8.5 cM to about 11.5 cM from the proximal end of chromosome 19; (viii) from about 9 cM to about 11 cM from the proximal end of chromosome 19; or (ix) from about 9.2 cM to about 10.8 cM from the proximal end of chromosome 19.

In yet other aspects, the interval is defined by flanking marker loci. In such aspects, the interval is a chromosomal interval flanked by and including: (i) marker loci BARC-038503-10136 and Satt554 on chromosome 13; (ii) marker loci Satt072 and BARC-027792-06674 on chromosome 13; (iii) marker loci BARC-018605-02982 and BARC-027792-06674 on chromosome 13; (iv) marker loci BARC-025859-05126 and BARC-014657-01608 on chromosome 13; (v) marker loci Gm13:36704369 and Gm13:36300296 on chromosome 13; (vi) marker loci BARC-028583-05961 and BARC-025561-06521 on chromosome 13; (vii) marker loci BARC-028887-06033 and BARC-027792-06674 on chromosome 13; (viii) marker loci BARC-018007-02494 and Satt522 on chromosome 13; (ix) marker loci BARC-039375-07306 and BARC-050993-10894 on chromosome 19; (x) marker loci BARC-039375-07306 and Satt182 on chromosome 19; (xi) marker loci BARC-039375-07306 and Satt232 on chromosome 19; (xii) marker loci Sat_301 and Satt182 on chromosome 19; (xiii) marker loci Sat_301 and Satt232 on chromosome 19; (xiv) marker loci BARC-039375-07304 and BARC-065445-19463 on chromosome 19; (xv) marker loci R176_1 and Satt182 on chromosome 19; or (xvi) marker loci Sat_301 and Satt446 on chromosome 19.

Each of the intervals described above shows a clustering of markers that co-segregate with decreased lodging (i.e., improved resistance to lodging). This clustering of markers occurs in relatively small domains on the linkage groups, indicating the presence of one or more QTL in those chromosome regions. QTL intervals were drawn to encompass the markers that co-segregate with improved resistance to lodging. The intervals are defined by the markers on their termini, where the interval encompasses all the markers that map within the interval as well as the markers that define the termini.

In some cases, an interval can be drawn, where the interval is defined by linkage to a particular marker locus. For example, an interval on chromosome 13 can be defined where any marker that is linked to the marker locus Gm13:36704369, Gm13:36300296 and/or Gm13:36593549 is a member of that interval. For example, as used here, linkage is defined as any marker that is within 25 cM, e.g., about 24, 23, 22, 21, 20, 19, 18, 17, 16, 15, 14, 13, 12, 11, 10, 9, 8, 7, 6, 5, 4, 3, 2, 1, 0.75, 0.5, 0.25 cM or less from Gm13:36704369, Gm13:36300296 and/or Gm13:36593549. In another embodiment, an interval on chromosome 19 can be defined where any marker that is linked to the marker locus Gm19:1589758 is a member of that interval. For example, as used here, linkage is defined as any marker that is within 25 cM, e.g., about 24, 23, 22, 21, 20, 19, 18, 17, 16, 15, 14, 13, 12, 11, 10, 9, 8, 7, 6, 5, 4, 3, 2, 1, 0.75, 0.5, 0.25 cM or less from Gm19:1589758.

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown.

In situations where the interval is close to or comprises one end of the linkage group, the interval can be described by one marker, for example the interval on chromosome 13 can be described as including marker Gm13:36704369 and below. In various further aspects, the interval on chromosome 13 can be described as including marker Gm13:36300296 and above. In a further aspect, the interval on chromosome 13 can be described as flanked by and including Gm13:36704369 and Gm13:36300296.

V. Genetic Maps

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL/marker genetic map relationships. However, it is not intended that the present methods be limited to any particular mapping populations, use of any particular software, or any particular set of software parameters to determine linkage of a particular marker or chromosome interval with the decreased lodging phenotype. It is well within the ability of one of ordinary skill in the art to extrapolate the novel features described herein to any soybean gene pool or population of interest, and using any particular software and software parameters. Indeed, observations regarding lodging resistance markers and chromosome intervals in populations in addition to those described herein are readily made using the teaching of the present disclosure.

Any suitable soybean strains can be used to generate mapping data or for marker association studies. A large number of commonly used soybean lines (e.g., commercial varieties) and mapping populations are known in the art. A broad range of mapping populations were used to obtain the results described in Examples.

A variety of commercial software is available for genetic mapping and marker association studies (e.g., QTL mapping). This software includes but is not limited to: JoinMap® (VanOoijen, and Voorrips (2001) "JoinMap 3.0 software for the calculation of genetic linkage maps," Plant Research International, Wageningen, the Netherlands; and, Stam, The Plant Journal 3(5): 739-744 (1993)); MapQTL® (J. W. vanOoijen, "Software for the mapping of quantitative trait loci in experimental populations" Kyazma B. V., Wageningen, Netherlands); MapManager QT (Manly and Olson, Genome 10: 327-334 (1999)); MapManager QTX (Manly, Cudmore and Meer, Mamm. Genome 12: 930-932 (2001)); GeneFlow® and QTLocate™ (GENEFLOW, Inc., Alexandria, Va.); and TASSEL ("Trait Analysis by aSSociation, Evolution, and Linkage" by Edward Buckler, and information about the program can be found on the Buckler Lab web page at the Institute for Genomic Diversity at Cornell University).

"Unified", "consensus" or "integrated" genetic maps have been created that incorporate mapping data from two or more sources, including sources that used different mapping populations and different modes of statistical analysis. The merging of genetic map information increases the marker density on the map, as well as improving map resolution. These improved maps can be advantageously used in marker assisted selection, map-based cloning, provide an improved framework for positioning newly identified molecular markers and aid in the identification of QTL chromosome intervals and clusters of advantageously-linked markers.

In some aspects, a consensus map is derived by simply overlaying one map on top of another. In other aspects, various algorithms, e.g., JoinMap® analysis, allows the combination of genetic mapping data from multiple sources, and reconciles discrepancies between mapping data from the original sources. See Van Ooijen, and Voorrips (2001) "JoinMap 3.0 software for the calculation of genetic linkage maps," Plant Research International, Wageningen, the Netherlands; and, Stam (1993) "Construction of integrated genetic linkage maps by means of a new computer package: JoinMap," The Plant Journal 3(5):739-744.

Additional integrated maps are known in the art. See, e.g., Cregan, et al., (1999) "An Integrated Genetic Linkage Map of the Soybean Genome", Crop Science 39:1464-1490; the Soybean Consensus Map 4.0 described by Hyten et al., (2010); and International Application Number PCT/US2004/024919 by Sebastian, filed Jul. 27, 2004, entitled "Soybean Plants Having Superior Agronomic Performance and Methods for their Production".

Song et al., provides another integrated soybean genetic map that incorporates mapping information from five different mapping populations (Song et al., (2004) "A New Integrated Genetic Linkage Map of the Soybean," Theor Appl Genet 109:122-128). This integrated map contains approximately 1,800 soybean markers, including SSR and SNP-type markers, as well as EST markers, RFLP markers, AFLP, RAPD, isozyme and classical markers (e.g., seed coat color). The markers that are on this map are known in the art and have been previously characterized. This information is also available at the website for the Soybean Genomics and Improvement Laboratory (SGIL) at the USDA Beltsville Agricultural Research Center (BARC). See, specifically, the description of projects in the Cregan Laboratory on that website.

The soybean integrated linkage map provided in Song et al., (2004) is based on the principle described by Stam (1993) "Construction of integrated genetic linkage maps by means of a new computer package: JoinMap," The Plant Journal 3(5):739-744; and Van Ooijen and Voorrips (2001) "JoinMap 3.0 software for the calculation of genetic linkage maps," Plant Research International, Wageningen, the Netherlands. Mapping information from five soybean populations was used in the map integration, and also used to place recently identified SSR markers onto the soybean genome. These mapping populations were Minsoy×Noir 1 (MN), Minsoy×Archer (MA), Noir 1×Archer (NA), Clark×Harosoy (CH) and A81-356022×P1468916 (MS). The JoinMap® analysis resulted in a map with 20 linkage groups containing a total of 1849 markers, including 1015 SSRs, 709 RFLPs, 73 RAPDs, 24 classical traits, six AFLPs, ten isozymes and 12 others. Among the mapped SSR markers were 417 previously uncharacterized SSRs.

Initially, LOD scores and pairwise recombination frequencies between markers were calculated. A LOD of 5.0 was used to create groups in the MS, MA, NA populations and LOD 4.0 in the MN and CH populations. The map of each linkage group was then integrated. Recombination values were converted to genetic distances using the Kosambi mapping function.

VI. Linkage Maps

From the present disclosure and widely recognized in the art, it is clear that any genetic marker that has a significant probability of co-segregation with a phenotypic trait of interest (e.g., in the present case, resistance or improved resistance to lodging) can be used as a marker for that trait. Useful QTL marker loci identified herein include one or more of the marker loci described on Tables 1 and 2. In a preferred embodiment, useful QTL marker loci include one or more marker locus selected from the group consisting of Gm13:36704369, Gm13:36300296, Gm13:36593549, Gm19:1589758 and a combination thereof.

Additional markers linked to the QTL markers can also be used to predict the resistance or resistance to lodging trait in a soybean plant. In other words, any other marker showing less than 50%, e.g., 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less recombination frequency (separated by a genetic distance less than 50 cM %, e.g., 45, 40, 35, 30, 25, 24, 23, 22, 21, 20, 19, 18, 17, 16, 15, 14, 13, 12, 11, 10, 9, 8, 7, 6, 5, 4, 3, 2, 1 cM or less) with a QTL marker of the invention is also a feature of the disclosure. Any marker that is linked to a QTL marker can also be used advantageously in marker-assisted selection for the particular trait.

Genetic markers that are linked to QTL markers are particularly useful when they are sufficiently proximal (e.g., closely linked) to a given QTL marker so that the genetic marker and the QTL marker display a low recombination frequency. In some aspects, such closely linked markers are a feature of the present disclosure. As defined herein, closely linked markers display a recombination frequency of about 10% or less, e.g., 9%, 8%, 7%, 6%, 5%, 4%, 3%, 2%, 1% or less (the given marker is within 10 cM, e.g., about 9, 8, 7, 6, 5, 4, 3, 2, 1 cM or less, of the QTL). Put another way, these closely linked loci co-segregate at least 90% of the time, e.g., about 91%, 92%, 93%, 94%, 95%, 96%, 97%, 98%, 99% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be proximal to each other.

Similarly, linked markers (including closely linked markers) of the invention can be determined by review of any suitable soybean genetic map. For example, the integrated genetic map described in Song et al., (2004) also provides a means to identify linked (including closely linked) markers. See also the website for the Soybean Genomics and Improvement Laboratory (SGIL) at the USDA Beltsville Agricultural Research Center (BARC), and see specifically the description of projects in the Cregan Laboratory on that website. That genetic map incorporates a variety of genetic markers that are known in the art or alternatively are described in that reference. Detailed descriptions of numerous markers, including many of those described in Song et al., (2004) can be found at the SOYBASE website resource.

It is not intended that the determination of linked or closely linked markers be limited to the use of any particular soybean genetic map. Indeed, a large number of soybean genetic maps are available and are well known to one of skill in the art. Another map that finds use with the invention in this respect is the integrated soybean genetic maps found on the SOYBASE website resource. Alternatively still, the determination of linked and closely linked markers can be made by the generation of an experimental dataset and linkage analysis.

It is not intended that the identification of markers that are linked (e.g., within about 50 cM or within about 10 cM) to the decreased lodging QTL markers identified herein be limited to any particular map or methodology. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any soybean genetic map can be used to determine markers that are linked and closely linked to the QTL markers of the present disclosure.

VII. Techniques for Marker Detection

Provided herein are molecular markers that have a significant probability of co-segregation with QTL that impart a decreased lodging phenotype. These QTL markers find use in marker assisted selection for desired traits (decreased lodging), and also have other uses. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP)). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization. Non-limiting examples of DNA sequencing methods useful in the methods provided herein include Next Generation Sequencing (NGS) technologies, for example, as described in Egan, A. N, et al. (2012) *American Journal of Botany* 99(2):175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) Laboratory Techniques in Biochemistry and Molecular Biology—Hybridization with Nucleic Acid Probes Elsevier, New York; Berger and Kimmel, Guide to Molecular Cloning Techniques, Methods in Enzymology volume 152 Academic Press, Inc., San Diego, Calif. ("Berger"); as well as in Sambrook and Ausubel (herein).

Typically, stringent conditions will be those in which the salt concentration is less than about 1.5 M Na ion, typically about 0.01 to about 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the thermal melting point (Tm) can be approximated from the equation of Meinkoth et al., *Anal. Biochem.* 138:267-284 (1984): Tm=81.5° C.+16.6 (log M) 4−0.41 (% GC)−0.61 (% form)−500/L; where M is the molarity of monovalent cations, % GC is the percentage of guano sine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm hybridization and/or wash conditions can be adjusted to hybridize to sequences of the desired identity. For example, if sequences with ≥90% identity are sought, the Tm can be decreased 10° C. Generally, stringent conditions are selected to be about 5° C. lower than Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm. Using the equation, hybridization and wash compositions, and desired Tm those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Inter-science, New York (1995). Hybridization and/or wash conditions can be applied for at least 10, 30, 60, 90, 120, or 240 minutes.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabeled PCR primers that are used to generate a radiolabeled amplicon. Labeling strategies for labeling nucleic acids and corresponding detection strategies can be found, e.g., in Haugland (1996) Handbook of Fluorescent Probes and Research Chemicals Sixth Edition by Molecular Probes, Inc. (Eugene Oreg.); or Haugland (2001) Handbook of Fluorescent Probes and Research Chemicals Eighth Edition by Molecular Probes, Inc. (Eugene Oreg.) (Available on CD ROM).

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also Ausubel, Sambrook and Berger, above.

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone, et al., (1995) "Molecular beacon probes combined with amplification by NASBA enable homogenous real-time detection of RNA" Nucleic Acids Res 26:2150-2155; Tyagi and Kramer, (1996) "Molecular beacons: probes that fluoresce upon hybridization" Nature Biotechnology 14:303-308; Blok and Kramer, (1997) "Amplifiable hybridization probes containing a molecular switch" Mol Cell Probes 11:187-194; Hsuih, et al., (1997) "Novel, ligation-dependent PCR assay for detection of hepatitis C in serum" J Clin Microbiol 34:501-507; Kostrikis, et al., (1998) "Molecular beacons: spectral genotyping of human alleles" Science 279:1228-1229; Sokol, et al., (1998) "Real time detection of DNA:RNA hybridization in living cells" Proc Natl Acad Sci USA 95:11538-11543; Tyagi, et al., (1998) "Multicolor molecular beacons for allele discrimination" Nature Biotechnology 16:49-53; Bonnet, et al., (1999) "Thermodynamic basis of the chemical specificity of structured DNA probes" Proc Natl Acad Sci USA 96:6171-6176; Fang, et al., (1999) "Designing a novel molecular beacon for surface-immobilized DNA hybridization studies" J Am Chem Soc 121:2921-2922; Marras, et al., (1999) "Multiplex detection of single-nucleotide variation using molecular beacons" Genet Anal Biomol Eng 14:151-156; and Vet, et al., (1999) "Multiplex detection of four pathogenic retroviruses using molecular beacons" Proc Natl Acad Sci USA 96:6394-6399. Additional details regarding MB construction and use is found in the patent literature, e.g., U.S. Pat. No. 5,925,517 (Jul. 20, 1999) to Tyagi, et al., entitled "Detectably labeled dual conformation oligonucleotide probes, assays and kits;" U.S. Pat. No. 6,150,097 (Nov. 21, 2000) to Tyagi, et al., entitled "Nucleic acid detection probes having non-FRET fluorescence quenching and kits and assays including such probes" and U.S. Pat. No. 6,037,130 (Mar. 14, 2000) to Tyagi, et al., entitled "Wavelength-shifting probes and primers and their use in assays and kits."

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli, et al., (1990) Proc Natl Acad Sci USA 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos, et al., (1995) Nucleic Acids Res 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker, et al., (1995) Mol Gen Genet 249:65; and Meksem, et al., (1995) Mol Gen Genet 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613 (the contents of which are incorporated herein by reference), the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

As herein, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qββ-replicase amplification and other RNA polymerase mediated techniques (e.g., NASBA), are found in the references noted above, e.g., Innis, Sambrook, Ausubel, Berger and Croy. Additional details are found in Mullis, et al., (1987) U.S. Pat. No. 4,683,202; Arnheim and Levinson, (Oct. 1, 1990) C&EN 36-47; The Journal Of NIH Research (1991) 3:81-94; Kwoh, et al., (1989) Proc Natl Acad Sci USA 86:1173; Guatelli, et al., (1990) Proc Natl Acad Sci USA 87:1874; Lomeli, et al., (1989) J Clin Chem 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564. Improved methods of amplifying large nucleic acids by PCR, which is useful in the context of positional cloning, are further summarized in Cheng, et al., (1994) Nature 369:684, and the references therein, in which PCR amplicons of up to 40 kb are generated.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers, (1981) Tetrahedron Letts 22(20):1859-1862, e.g., using a commercially available automated synthesizer, e.g., as described in Needham-VanDevanter, et al., (1984) Nucleic Acids Res 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-Products, Inc., BMA Biomedicals Ltd (U.K.), Bio•Synthesis, Inc., and many others.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers".

It will be appreciated that, although many specific examples of primers are provided herein (see, e.g., Table 3), suitable primers to be used with the invention can be designed using any suitable method. It is not intended that the invention be limited to any particular primer or primer pair. For example, primers can be designed using any suitable software program, such as LASERGENE®.

In some embodiments, the primers of the invention are radiolabeled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons.

It is not intended that the primers of the present methods be limited to generating an amplicon of any particular size. For example, the primers used to amplify the marker loci and alleles herein are not limited to amplifying the entire region of the relevant locus. The primers can generate an amplicon of any suitable length that is longer or shorter than the amplicons described herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited in Tables 1 and 2 also find use with the present methods.

VIII. Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present disclosure provides the means to identify plants, particularly soybean plants that are resistant or exhibit improved resistance to lodging by identifying plants having a marker allele that positively correlates with improved resistance to lodging, such as a favorable allele of one of the marker loci described in Tables 1 and 2. In a preferred embodiment, a soybean plant or soybean germplasm is identified and/or selected that comprises a favorable allele of marker locus Gm13:36704369, Gm13:36300296, Gm13:36596549, and/or Gm19:1589758. In other embodiments, the present disclosure provides the means to identify plants, particularly soybean plants that are susceptible to lodging by identifying plants having a marker allele that positively correlates with lodging susceptibility, such as an allele of one or the marker loci described in Tables 1 and 2.

Similarly, by identifying plants lacking the desired marker locus, susceptible or less resistant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

The disclosure also provides chromosome QTL intervals that find equal use in MAS to select plants that demonstrate decreased lodging. Similarly, the QTL intervals can also be used to counter-select plants that display increased lodging. Any marker that maps within the QTL interval (including the termini of the intervals) finds use with the invention. In some embodiments, the interval is a chromosomal interval that is localized: (i) from about 67 cM to about 88 cM from the proximal end of chromosome 13; (ii) from about 68 cM to about 87 cM from the proximal end of chromosome 13; (iii) from about 69 cM to about 86 cM from the proximal end of chromosome 13; (iv) from about 70 cM to about 85 cM from the proximal end of chromosome 13; (v) from about 75 cM to about 80 cM from the proximal end of chromosome 13; (vi) from about 75.4 cM to about 79.5 cM from the proximal end of chromosome 13; (vii) from about 75.9 cM to about 79 cM from the proximal end of chromosome 13; (viii) from about 76.4 cM to about 78.5 cM from the proximal end of chromosome 13; or (ix) from about 76.9 cM to about 78 cM from the proximal end of chromosome 13. In another aspect, the interval is a chromosomal interval located at about 5 cM to about 15 cM from the proximal end of chromosome 19. In other embodiments, the interval is a chromosomal interval that is localized: (i) from about 5 cM to about 15 cM from the proximal end of chromosome 19; (ii) from about 5.5 cM to about 14.5 cM from the proximal end of chromosome 19; (iii) from about 6 cM to about 14 cM from the proximal end of chromosome 19; (iv) from about 7 cM to about 13 cM from the proximal end of chromosome 19; (v) from about 7.5 cM to about 12.5 cM from the proximal end of chromosome 19; (vi) from about 8 cM to about 12 cM from the proximal end of chromosome 19; (vii) from about 8.5 cM to about 11.5 cM from the proximal end of chromosome 19; (viii) from about 9 cM to about 11 cM from the proximal end of chromosome 19; or (ix) from about 9.2 cM to about 10.8 cM from the proximal end of chromosome 19.

In yet other aspects, the interval is described as flanked by and including: (i) marker loci BARC-038503-10136 and Satt554 on chromosome 13; (ii) marker loci Satt072 and BARC-027792-06674 on chromosome 13; (iii) marker loci BARC-018605-02982 and BARC-027792-06674 on chromosome 13; (iv) marker loci BARC-025859-05126 and BARC-014657-01608 on chromosome 13; (v) marker loci Gm13:36704369 and Gm13:36300296 on chromosome 13; (vi) marker loci BARC-028583-05961 and BARC-025561-06521 on chromosome 13; (vii) marker loci BARC-028887-06033 and BARC-027792-06674 on chromosome 13; (viii) marker loci BARC-018007-02494 and Satt522 on chromosome 13; (ix) marker loci BARC-039375-07306 and BARC-050993-10894 on chromosome 19; (x) marker loci BARC-039375-07306 and Satt182 on chromosome 19; (xi) marker loci BARC-039375-07306 and Satt232 on chromosome 19; (xii) marker loci Sat_301 and Satt182 on chromosome 19; (xiii) marker loci Sat_301 and Satt232 on chromosome 19; (xiv) marker loci BARC-039375-07304 and BARC-065445-19463 on chromosome 19; (xv) marker loci R176_1 and Satt182 on chromosome 19; or (xvi) marker loci Sat_301 and Satt446 on chromosome 19.

In general, MAS uses polymorphic markers that have been identified as having a significant likelihood of co-segregation with a lodging resistance trait. Such markers are presumed to map near a gene or genes that give the plant its lodging resistance phenotype, and are considered indicators for the desired trait, and are termed QTL markers. Plants are tested for the presence of a desired allele in the QTL marker. The most preferred markers (or marker alleles) are those that have the strongest association with the lodging resistance trait.

Linkage analysis is used to determine which polymorphic marker allele demonstrates a statistical likelihood of co-segregation with the lodging resistance phenotype (thus, a "lodging resistance marker allele"). Following identification of a marker allele for co-segregation with the lodging resistance phenotype, it is possible to use this marker for rapid, accurate screening of plant lines for the lodging resistance allele without the need to grow the plants through their life cycle and await phenotypic evaluations, and furthermore, permits genetic selection for the particular lodging resistance allele even when the molecular identity of the actual lodging resistance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired lodging resistance phenotype. In brief, a nucleic acid corresponding to the marker nucleic acid allele is detected in a biological sample from a plant to be selected.

This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "TECHNIQUES FOR MARKER DETECTION." After the presence (or absence) of a particular marker allele in the biological sample is verified, the plant is selected, e.g., used to make progeny plants by selective breeding.

Soybean plant breeders desire combinations of lodging resistance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein, when genetically-linked to lodging resistance loci, provide an effective method for selecting resistant varieties in breeding programs. For example, one advantage of marker-assisted selection over field evaluations for lodging resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in lodging resistance, or multiple loci each involved in lodging resistance or resistance to different diseases, the efficiency of MAS compared to phenotypic screening becomes even greater, because all of the loci can be evaluated in the lab together from a single sample of DNA.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable lodging resistance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because lodging resistant plants may be otherwise undesirable, e.g., due to low yield, low fecundity, or the like.

IX. Introgression of Favorable Alleles

One application of MAS, in the context of the present disclosure is to use the resistance or improved resistance to lodging markers to increase the efficiency of an introgression or backcrossing effort aimed at introducing a lodging resistance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present disclosure can be utilized to guide marker assisted selection or breeding of soybean varieties with the desired complement (set) of allelic forms of chromosome segments associated with superior agronomic performance (lodging resistance, along with any other available markers for yield, disease resistance, etc.). Any of the disclosed marker alleles can be introduced into a soybean line via introgression, by traditional breeding (or introduced via transformation, or both) to yield a soybean plant with superior agronomic performance. The number of alleles associated with lodging resistance that can be introduced or be present in a soybean plant of the present invention ranges from 1 to the number of alleles disclosed herein, each integer of which is incorporated herein as if explicitly recited.

The present disclosure also extends to a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with lodging resistance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the markers of the present invention, such that the progeny are capable of inheriting the allele.

Often, a method of the present invention is applied to at least one related soybean plant such as from progenitor or descendant lines in the subject soybean plant's pedigree such that inheritance of the desired lodging resistance allele can be traced. The number of generations separating the soybean plants being subject to the methods of the present disclosure will generally be from 1 to 20, commonly 1 to 5, and typically 1, 2 or 3 generations of separation, and quite often a direct descendant or parent of the soybean plant will be subject to the method (i.e., one generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present disclosure can be used for MAS in crosses involving elite×exotic soybean lines by subjecting the segregating progeny to MAS to maintain major yield alleles, along with the lodging resistance marker alleles herein.

In some embodiments, a method is provided that comprises selecting a soybean plant or soybean germplasm having improved resistance to lodging by detecting one or more of the marker loci described herein and further crossing the selected soybean plant or soybean germplasm with a second soybean plant or soybean germplasm to introgress the improved lodging resistance QTL into a progeny soybean plant or soybean germplasm. In such embodiments, the second soybean plant or soybean germplasm displays susceptibility to lodging or decreased lodging resistance as compared to the selected soybean plant or soybean progeny. Thus, by crossing the two parental plants, the improved lodging resistance trait is then introgressed into a subset or subpopulation of progeny soybean plants or soybean germplasm and confers to these soybean progeny improved lodging resistance as compared to the second soybean parent.

In certain aspects, the marker loci provided herein are within or linked to a QTL or QTL interval that is associated with agronomic traits in addition to improved resistance to lodging. For example, marker loci are provided herein that are associated with plant height in addition to lodging severity. Soybean plants with increased height are more susceptible to lodging than soybean plants having decreased height. Thus, in some embodiments, favorable alleles of the marker loci described herein are suitable for detecting soybean plants and soybean germplasm with decreased height and improved resistance to lodging. In such embodiments, the decreased height trait can be introgressed into progeny soybean plants or germplasm using the instant methods. For example, in one embodiment, the subset or subpopulation of progeny soybean plants or soybean germplasm produced by crossing the soybean plant selected by the methods provided herein with a second soybean plant may additionally display decreased height as compared to the second soybean parent.

Progeny soybean plants and germplasm produced by the breeding a soybean plant or soybean germplasm having the improved lodging resistance trait with a soybean plant or soybean germplasm that does not have the improved lodging resistance trait can be screened using the detection methods described herein in order to identify and/or select a progeny soybean plant or germplasm in which the desired QTL has been introgressed.

X. Generation of Transgenic Cells and Plants

The present disclosure also relates to host cells and organisms which are transformed with nucleic acids corresponding to lodging resistance QTL identified according to the invention. For example, such nucleic acids include chromosome intervals (e.g., genomic fragments) that encode a lodging resistance or improved lodging resistance trait.

General texts which describe molecular biological techniques for the cloning and manipulation of nucleic acids and production of encoded polypeptides include Berger, Sambrook, and Ausubel, herein. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors of this invention which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (Fromm, et al., (1985) Proc Natl Acad Sci USA 82:5824), infection by viral vectors such as cauliflower mosaic virus (CaMV) (Hohn, et al., (1982) Molecular Biology of Plant Tumors Academic Press, New York, pp. 549-560; Howell, U.S. Pat. No. 4,407,956), high velocity ballistic penetration by small particles with the nucleic acid either within the matrix of small beads or particles, or on the surface (Klein, et al., (1987) Nature 327:70), use of pollen as vector (WO85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch, et al., (1984) Science 233:496; Fraley, et al., (1983) Proc Natl Acad Sci USA 80:4803). Additional details regarding nucleic acid introduction methods are found in Sambrook, Berger and Ausubel, supra. The method of introducing a nucleic acid of the present disclosure into a host cell is not critical to the instant disclosure, and it is not intended that the disclosure be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the disclosure.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, supra, plant regeneration from cultured protoplasts is described in Evans, et al., (1983) "Protoplast Isolation and Culture," Handbook of Plant Cell Cultures 1:124-176 (MacMillan Publishing Co., New York; Davey, (1983) "Recent Developments in the Culture and Regeneration of Plant Protoplasts," Protoplasts, pp. 12-29, (Birkhauser, Basel); Dale, (1983) "Protoplast Culture and Plant Regeneration of Cereals and Other Recalcitrant Crops," Protoplasts pp. 31-41, (Birkhauser, Basel); Binding (1985) "Regeneration of Plants," Plant Protoplasts, pp. 21-73, (CRC Press, Boca Raton, Fla.). Additional details regarding plant cell culture and regeneration include Payne, et al., (1992) Plant Cell and Tissue Culture in Liquid Systems John Wiley & Sons, Inc. New York, N.Y.; Gamborg and Phillips, (eds) (1995) Plant Cell, Tissue and Organ Culture; Fundamental Methods Springer Lab Manual, Springer-Verlag (Berlin Heidelberg New York) and Plant Molecular Biology (1993) Croy, Ed. Bios Scientific Publishers, Oxford, U.K. ISBN 0 12 198370 6. Cell culture media in general are also set forth in Atlas and Parks, (eds) The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc (St Louis, Mo.) ("Sigma-LSRCCC") and, e.g., the Plant Culture Catalogue and supplement (e.g., 1997 or later) also from Sigma-Aldrich, Inc (St Louis, Mo.) ("Sigma-PCCS").

The present disclosure also relates to the production of transgenic organisms, which may be bacteria, yeast, fungi, animals or plants, transduced with the nucleic acids of the disclosure (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present disclosure. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this disclosure. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith, (1979) Gene 8:81; Roberts, et al., (1987) Nature 328:731; Schneider, et al., (1995) Protein Expr Purif 6435:10; Ausubel, Sambrook, Berger (all supra). A catalogue of Bacteria and Bacteriophages useful for cloning is provided, e.g., by the ATCC, e.g., The ATCC Catalogue of Bacteria and Bacteriophaqe (1992) Gherna, et al., (eds) published by the ATCC. Additional basic procedures for sequencing, cloning and other aspects of molecular biology and underlying theoretical considerations are also found in Watson, et al., (1992) Recombinant DNA, Second Edition, Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Techniques for transforming plant cells with nucleic acids are widely available and can be readily adapted to the disclosure. In addition to Berger, Ausubel and Sambrook, all supra, useful general references for plant cell cloning, culture and regeneration include Jones, (ed) (1995) Plant Gene Transfer and Expression Protocols—Methods in Molecular Biology, Volume 49 Humana Press Towata N.J.; Payne, et al., (1992) Plant Cell and Tissue Culture in Liquid Systems John Wiley & Sons, Inc. New York, N.Y. (Payne); and Gamborg and Phillips, (eds) (1995) Plant Cell, Tissue and Organ Culture; Fundamental Methods Springer Lab Manual, Springer-Verlag (Berlin Heidelberg New York) (Gamborg). A variety of cell culture media are described in Atlas and Parks, (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology, Bios Scientific Publishers, Oxford, U.K.

The nucleic acid constructs of the disclosure, e.g., plasmids, cosmids, artificial chromosomes, DNA and RNA polynucleotides, are introduced into plant cells, either in culture or in the organs of a plant by a variety of conventional techniques. Techniques for transforming a wide variety of higher plant species are also well known and described in widely available technical, scientific, and patent literature. See, for example, Weissinger, et al., (1988) Ann Rev Genet 22:421-477. The DNA constructs of the disclosure, for example plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones, (ed) (1995) Plant Gene Transfer and Expression Protocols—Methods in Molecular Biology, Volume 49 Humana Press, Towata, N.J., as well as in the other references noted herein and available in the literature.

For example, the introduction of DNA constructs using polyethylene glycol precipitation is described in Paszkowski, et al., (1984) EMBO J 3:2717. Electroporation techniques are described in Fromm, et al., (1985) Proc Natl Acad Sci USA 82:5824. Ballistic transformation techniques are described in Klein, et al., (1987) Nature 327:70-73. Additional details are found in Jones, (1995) and Gamborg and Phillips, (1995), supra, and in U.S. Pat. No. 5,990,387.

Alternatively, and in some cases preferably, *Agrobacterium*-mediated transformation is employed to generate transgenic plants. *Agrobacterium*-mediated transformation techniques, including disarming and use of binary vectors, are also well described in the scientific literature. See, for example, Horsch, et al., (1984) Science 233:496; and Fraley, et al., (1984) Proc Natl Acad Sci USA 80:4803 and recently reviewed in Hansen and Chilton, (1998) Current Topics in Microbiology 240:22; and Das, (1998) Subcellular Biochemistry 29: Plant Microbe Interactions, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller, (1987) In: Genetic Engineering, vol. 6, PWJ Rigby, Ed., London, Academic Press; and Lichtenstein and Draper (1985) In: DNA Cloning, Vol. II, Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) Plant Cell Physiol 25:1353), (3) the vortexing method (see, e.g., Kindle, (1990) Proc Natl Acad Sci USA 87:1228.

DNA can also be introduced into plants by direct DNA transfer into pollen as described by Zhou, et al., (1983) Methods in Enzymology 101:433; Hess, (1987) Intern Rev Cytol 107:367; Luo, et al., (1988) Plant Mol Biol Rep 6:165. Expression of polypeptide coding genes can be obtained by injection of the DNA into reproductive organs of a plant as described by Pena, et al., (1987) Nature 325:274. DNA can also be injected directly into the cells of immature embryos and the desiccated embryos rehydrated as described by Neuhaus, et al., (1987) Theor Appl Genet 75:30; and Benbrook, et al., (1986) in Proceedings Bio Expo Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne, et al., (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); Evans, et al., (1983) Protoplasts Isolation and Culture, Handbook of Plant Cell Culture pp. 124-176, Macmillian Publishing Company, New York; and Binding (1985) Regeneration of Plants, Plant Protoplasts pp. 21-73, CRC Press, Boca Raton. Regeneration can also be obtained from plant callus, explants, somatic embryos (Dandekar, et al., (1989) J Tissue Cult Meth 12:145; McGranahan, et al., (1990) Plant Cell Rep 8:512) organs, or parts thereof. Such regeneration techniques are described generally in Klee, et al., (1987) Ann Rev Plant Phys 38:467-486. Additional details are found in Payne, (1992) and Jones (1995), both supra, and Weissbach and Weissbach, eds. (1988) Methods for Plant Molecular Biology Academic Press, Inc., San Diego, Calif. This regeneration and growth process includes the steps of selection of transformant cells and shoots, rooting the transformant shoots and growth of the plantlets in soil. These methods are adapted to the disclosure to produce transgenic plants bearing QTLs according to the methods of the disclosure.

In addition, the regeneration of plants containing nucleic acids of the present disclosure and introduced by *Agrobacterium* into cells of leaf explants can be achieved as described by Horsch, et al., (1985) Science 227:1229-1231. In this procedure, transformants are grown in the presence of a selection agent and in a medium that induces the regeneration of shoots in the plant species being transformed as described by Fraley, et al., (1983) Proc Natl Acad Sci USA 80:4803. This procedure typically produces shoots within two to four weeks and these transformant shoots are then transferred to an appropriate root-inducing medium containing the selective agent and an antibiotic to prevent bacterial growth. Transgenic plants of the present disclosure may be fertile or sterile.

It is not intended that plant transformation and expression of polypeptides that provide lodging resistance, as provided by the present disclosure, be limited to soybean species. Indeed, it is contemplated that the polypeptides that provide the desired lodging resistance in soybean can also provide such lodging resistance when transformed and expressed in other agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria and sweetpea); and Compositae (the largest family of vascular plants, including at least 1,000 genera, including important commercial crops such as sunflower).

Additionally, preferred targets for modification with the nucleic acids of the disclosure, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna* and many others.

Common crop plants which are targets of the present disclosure include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

In construction of recombinant expression cassettes of the disclosure, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of nucleic acids of the disclosure in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella, et al., (1983) Nature 303:209. Viral promoters include the 35S and 19S RNA promoters of cauliflower mosaic virus. See, Odell, et al., (1985) Nature 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) EMBO J 7:3315. Many other promoters are in current use and can be coupled to an exogenous DNA sequence to direct expression.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

A vector comprising sequences of the disclosure will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosulforon, or phosphinothricin (the active ingredient in the herbicides bialaphos or Basta). See, e.g., Padgette, et al., (1996) In: Herbicide-Resistant Crops (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil, (1996) In: Herbicide-Resistant Crops (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the disclosure, provided that these parts comprise cells comprising the isolated nucleic acid of the present disclosure. Progeny and variants, and mutants of the regenerated plants are also included within the scope of the disclosure, provided that these parts comprise the introduced nucleic acid sequences.

Transgenic or introgressed plants comprising nucleic acids of the present disclosure can be screened for transmission of the nucleic acid of the present disclosure by, for example, standard nucleic acid detection methods or by immunoblot protocols.

A preferred embodiment of the disclosure is a transgenic plant that is homozygous for the added heterologous nucleic acid; e.g., a transgenic plant that contains two added nucleic acid sequence copies. A homozygous transgenic plant can be obtained by sexually mating (self-fertilizing) a heterozygous transgenic plant that contains a single added heterologous nucleic acid. Back-crossing to a parental plant and outcrossing with a non-transgenic plant can be used to introgress the heterologous nucleic acid into a selected background (e.g., an elite or exotic soybean line).

XI. Methods for Lodging Resistant Soybean Plants

Experienced plant breeders can recognize lodging resistant soybean plants in the field, and can select the lodging resistant individuals or populations for breeding purposes or for propagation. In this context, the plant breeder recognizes soybean plants with "resistance" or "improved resistance" to lodging as compared to "susceptible", or "non-resistant" soybean plants.

Such plant breeding practitioners will appreciate that plant resistance to lodging is a phenotypic spectrum consisting of extremes in resistance, susceptibility and a continuum of intermediate resistance phenotypes. Lodging resistance also varies due to environmental effects. Evaluation of phenotypes using reproducible assays and lodging resistance scoring methods are of value to scientists who seek to identify genetic loci that impart lodging resistance, conduct marker assisted selection for resistant populations, and for introgression techniques to breed a lodging resistance trait into an elite soybean line, for example.

In contrast to fortuitous field observations that classify plants as either "resistant" or "susceptible", various systems are known for scoring the degree of plant lodging resistance or susceptibility. These techniques can be applied to different fields at different times, and provide approximate lodging resistance scores that can be used to characterize a given strain regardless of growth conditions or location.

Ratings are assigned by evaluating all plants of a cultivar in a plot, e.g., a 5 feet by 36 inches plot. Cultivar scores are based on a 1 to 9 system where lodging is scored visually for each plot and rated on a scale of 1 to 9 representing the percentage of plants in the row at harvest maturity that are less than fully erect. Plots with almost all plants fully erect are scored a 9, plots with most plants at a 45 degree angle in relation to the ground are scored a 5, and plots with almost all plants laying on the ground are scored a 1.

XII. Automated Detection/Correlation Systems of the Disclosure

In some embodiments, provided herein are methods that includes an automated system for detecting markers of the disclosure and/or correlating the markers with a desired phenotype (e.g., lodging resistance). Thus, a typical system can include a set of marker probes or primers configured to detect at least one favorable allele of one or more marker locus associated with resistance or improved resistance to lodging. These probes or primers are configured to detect the marker alleles noted in the tables and examples herein, e.g., using any available allele detection format, e.g., solid or liquid phase array based detection, microfluidic-based sample detection, etc.

For example, in one embodiment, a kit for selecting at least one soybean plant by marker assisted selection of a QTL associated with improved lodging resistance is provided that includes primers or probes for detecting one or more of the marker loci selected from the group consisting of Gm13:36431456, Gm13:36490271, Gm13:36491753, Gm13:36491754, Gm13:36492037, Gm13:36492926, Gm13:36492955, Gm13:36493615, Gm13:36494839, Gm13:36517239, Gm13:36539789, Gm13:36539798, Gm13:36540415, Gm13:36593549, Gm13:36613902, Gm13:36644196, Gm13:36644203, Gm13:36644207, Gm13:36678427, Gm13:36697528, Gm13:36795108, Gm13:36704369, Gm13:36300296, Gm13:36567042, Gm13:36792347, Gm13:36864280, Gm13:37443784, Gm19:1306591, Gm19:1635254, Gm19:841738, Gm19:1589758, and a combination thereof. In other embodiments, the one or more marker loci is localized between 36,410 and 36,419 kbp of chromosome 13 (SEQ ID NO: 87). In still other embodiments, the marker locus is localized within a chromosomal interval flanked by and including marker loci(i) marker loci BARC-038503-10136 and Satt554 on chromosome 13; (ii) marker loci Satt072 and BARC-027792-06674 on chromosome 13; (iii) marker loci BARC-018605-02982 and BARC-027792-06674 on chromosome 13; (iv) marker loci BARC-025859-05126 and BARC-014657-01608 on chromosome 13; (v) marker loci Gm13:36704369 and Gm13:36300296 on chromosome 13; (vi) marker loci BARC-028583-05961 and BARC-025561-06521 on chromosome 13; (vii) marker loci BARC-028887-06033 and BARC-027792-06674 on chromosome 13; (vii) marker loci BARC-018007-02494 and Satt522 on chromosome 13; (viii) marker loci BARC-039375-07306 and BARC-050993-10894 on chromosome 19; (ix) marker loci BARC-039375-07306 and Satt182 on chromosome 19; (x) marker loci BARC-039375-07306 and Satt232 on chromosome 19; (xi) marker loci Sat_301 and Satt182 on chromosome 19; (xii) marker loci Sat_301 and Satt232 on chromosome 19; (xiii) marker loci BARC-039375-07304 and BARC-065445-19463 on chromosome 19; (xiv) marker loci R176_1 and Satt182 on chromosome 19; or (xv) marker loci Sat_301 and Satt446 on chromosome 19.

In other aspects, a kit for selecting at least one soybean plant by marker assisted selection of a QTL associated with improved lodging resistance is provided that includes primers or probes for detecting a polymorphism in the soybean genome, wherein the physical position of the polymorphism is selected from the group consisting of 36,431,456 bp on chromosome 13, 36,490,271 bp on chromosome 13, 36,491,753 bp on chromosome 13, 36,491,754 bp on chromosome 13, 36,492,037 bp on chromosome 13, 36,492,926 bp on chromosome 13, 36,492,955 bp on chromosome 13, 36,493,615 bp on chromosome 13, 36,494,839 bp on chromosome 13, 36,517,239 bp on chromosome 13, 36,539,789 bp on chromosome 13, 36,539,798 bp on chromosome 13, 36,540,415 bp on chromosome 13, 36,593,549 bp on chromosome 13, 36,613,902 bp on chromosome 13, 36,644,196 bp on chromosome 13, 36,644,203 bp on chromosome 13, 36,644,207 bp on chromosome 13, 36,678,427 bp on chromosome 13, 36,697,528 bp on chromosome 13, 36,795,108 bp on chromosome 13, 36,704,369 bp on chromosome 13, 36,300,296 bp on chromosome 13, 36,567,042 bp on chromosome 13, 36,792,347 bp on chromosome 13, 36,864,280 bp on chromosome 13, 37,443,784 bp on chromosome 13 and a combination thereof.

In other aspects, a kit for selecting at least one soybean plant by marker assisted selection of a QTL associated with improved lodging resistance is provided that includes primers or probes for detecting a polymorphism in the soybean genome, wherein the physical position of the polymorphism is selected from the group consisting of 1,306,591 bp on chromosome 19, 1,635,254 bp on chromosome 19, 841,738 bp on chromosome 19, 1,589,758 bp on chromosome 19, and a combination thereof.

The typical system includes a detector that is configured to detect one or more signal outputs from the set of marker probes or primers, or amplicon thereof, thereby identifying the presence or absence of the allele. A wide variety of signal detection apparatus is available, including photo multiplier tubes, spectrophotometers, CCD arrays, arrays and array scanners, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is especially preferred and is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted lodging resistance phenotype are also a feature of the disclosure. For example, the instructions can include at least one look-up table that includes a correlation between the presence or absence of the favorable alleles and the predicted lodging resistance or improved lodging resistance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the presence or absence of the favorable alleles and predicted lodging resistance or improved lodging resistance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present disclosure, e.g., in an automated system. The computer readable media can include cache, main, and storage memory and/or other electronic data storage components (hard drives, floppy drives, storage drives, etc.) for storage of computer code. Data representing alleles detected by the method of the present disclosure can also be electronically, optically, or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" in the context of this disclosure refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program", by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems of the disclosure.

For example, lodging resistance marker allele values assigned to a population of progeny descending from crosses between elite lines are recorded in a computer readable medium, thereby establishing a database corresponding resistance alleles with unique identifiers for members of the population of progeny. Any file or folder, whether custom-made or commercially available (e.g., from Oracle or Sybase) suitable for recording data in a computer readable medium is acceptable as a database in the context of the present disclosure. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay(s) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between lodging resistance and the alleles of the disclosure is then executed by the computational device to identify correlations between marker alleles and predicted trait phenotypes.

Typically, the system also includes a user input device, such as a keyboard, a mouse, a touchscreen, or the like (for, e.g., selecting files, retrieving data, reviewing tables of maker information), and an output device (e.g., a monitor, a printer) for viewing or recovering the product of the statistical analysis.

Thus, in one aspect, the disclosure provides an integrated system comprising a computer or computer readable medium comprising a set of files and/or a database with at least one data set that corresponds to the marker alleles herein. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for molecular marker analysis of the present disclosure can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., lodging resistance or improved lodging resistance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, LINUX, or UNIX based (e.g., SUN™ work station) computers.

The present disclosure is illustrated by the following examples. The foregoing and following description and the various examples are not intended to be limiting but rather are illustrative of the described embodiments. Hence, it will be understood that the present disclosure is not limited to the specific details of these examples.

EXAMPLES

Example 1: QTL Mapping

Bi-parental populations were created by crossing two soybean varieties. The F1 seed was grown and bulk generation advanced twice. The F3 seed was planted and individual plants were derived to create a segregating population of F3:4 varieties. The individual varieties were planted and evaluated in field plots. Bi-parental populations of F3:4 individuals were grown at research locations across the US including North Dakota, Minnesota, Iowa, Illinois, Ohio, and Kansas. Individual varieties were grown as single replicate 5 foot plots on 36 inch rows. Bi-parental populations were grown at multiple locations within their target environments. Height data was collected at maturity by measuring the average of five plants from the soil level to the top of the mature plants for each plot. Lodging severity was scored visually for each plot using a 1-9 scale representing the percentage of plants in the row at harvest maturity that were less than fully erect. Plots with almost all plants fully erect were scored a 9, plots with most plants at a 45 degree angle in relation to the ground were scored a 5, and plots with almost all plants laying on the ground were scored a 1.

QTL mapping was performed on each of the populations and the results are listed in Table 4. To perform QTL mapping, genomic DNA must be extracted from plant tissue using any suitable genomic DNA extraction technique known in the art. One exemplary technique suitable for extracting genomic DNA from plant leaf tissue is a modification of the CTAB (cetyltriethylammonium bromide, Sigma H5882) method described by Stacey & Isaac (Methods in Molecular Biology, Vol. 28: Protocols for Nucleic Acid Analysis by Nonradioactive Probes, Ed: Isaac, Humana Press Inc, Totowa, N.J. 1994, Ch 2, pp. 9-15). In the CTAB procedure, approximately 100-200 mg of tissue is ground into powder in liquid nitrogen and homogenized in 1 ml of CTAB extraction buffer (2% CTAB, 0.02 M EDTA, 0.1 M Tris-Cl pH 8, 1.4 M NaCl, 25 mM DTT) for 30 minutes at 65° C. Homogenized samples are cooled at room temperature for 15 minutes before a single protein extraction with approximately 1 ml 24:1 v/v chloroform:octanol is done. Samples are centrifuged for 7 min at 13,000 rpm and the upper layer of supernatant is collected using wide-mouthed pipette tips. DNA is then precipitated from the supernatant by incubation in 95% ethanol on ice for 1 hour. DNA threads are then spooled onto a glass hook, washed in 75% ethanol containing 0.2 M sodium acetate for 10 minutes, air-dried for 5 minutes and resuspended in TE buffer. Five RNAse A is added to the samples, which are then incubated at 37° C. for 1 hour.

Once, genomic DNA is extracted, Multiple QTL mapping analysis (MQM) can then be performed. MQM was performed on each of the populations described above using the MQM R/QTL package under recommended parameters as described in, e.g., Broman, K. W. and Sen, S., A guide to QTL mapping with R/qtl. Springer. http://www.rqtl.org/book (2009); Arends, D. et al., R/qtl: high-throughput multiple QTL mapping, *Bioinformatics* 26(23):2990-2992 (2010); and Arends, D. et al., Tutorial-Multiple-QTL Mapping (MQM) Analysis for R/qt, http://www.rqtl.org/tutorials/MQM-tour.pdf (2014).

A novel QTL controlling plant height and lodging was found on chromosome 13 at about 77.45 cM across twenty-three breeding populations. Both individual location QTL mapping and combined mapping across locations is presented. In total, eighteen populations showed significant QTL for height and ten populations showed a statistically significant QTL for lodging severity in the claimed region at one or a combination of locations. As seen in Table 4, the variance explained by the QTL ranged from 5.13% to 35.64%. The additive effect of the QTL on height ranged from 0.8-2.68 inches and on lodging severity ranged from a score change of 0.32-0.83 depending on the population and environment, suggesting that the QTL has a large impact on both of these traits. The additive effect is provided in positive and negative values. An additive effect with a negative value indicates that the allele at this locus from the female parent contributed to increased height and/or lodging resistance, whereas an additive effect with a positive value indicates that the allele at this locus from the male parent contributed to increased height and/or lodging resistance in the population. Height and lodging are correlated traits in many environments as taller plants are more prone to lodge (see Wilcox, J. R. and Sediyama, T., Euphytica (1981) 30:323-326).

TABLE 4

QTL mapping on chromosome 13.

| Pop ID | ♀ ID | ♂ ID | Geographic Location | Trait | LOD | VAR | P Value | QTL peak | ADD | CI |
|---|---|---|---|---|---|---|---|---|---|---|
| 1 | 1 | 21 | 1 | HGT | 4.77 | 9.2 | 0.00002 | 81.65 | −1.27 | 74.75-90.03 |
| 2 | 2 | 22 | 2 | HGT | 14 | 14.72 | 0 | 79.93 | −2.15 | 77.17-87.85 |
| 2 | 2 | 22 | combined | HGT | 28.9 | 16.34 | 0 | 87.85 | −2.49 | 77.17-87.85 |
| 3 | 3 | 22 | combined | HGT | 7.37 | 6.84 | 0 | 83.84 | −2.45 | 78.89-84.68 |
| 3 | 3 | 22 | 2 | HGT | 4.5 | 7.85 | 0.00003 | 83.84 | −2.66 | 78.89-84.68 |
| 3 | 3 | 22 | 3 | HGT | 7.39 | 13.47 | 0 | 83.84 | −2.31 | 78.89-84.68 |
| 2 | 2 | 22 | 3 | HGT | 25.51 | 31.92 | 0 | 87.85 | −2.68 | 79.93-87.85 |
| 3 | 3 | 22 | 2 | LDGSEV | 4.82 | 8.19 | 0.00002 | 83.84 | 0.83 | 78.89-84.68 |
| 4 | 4 | 21 | 1 | HGT | 7.38 | 15.27 | 0 | 77.62 | −1.67 | 74.68-77.73 |
| 5 | 5 | 23 | 4 | HGT | 5.05 | 14.92 | 0.00001 | 84.68 | −1.77 | 76.22-93.1 |
| 6 | 6 | 23 | 5 | HGT | 3.7 | 6.88 | 0.0002 | 97.87 | −0.99 | 79.58-102.47 |
| 7 | 7 | 24 | combined | HGT | 15.23 | 11.48 | 0 | 71.22 | 1.53 | 70.06-71.22 |
| 7 | 7 | 24 | 6 | HGT | 4.36 | 7.03 | 0.00004 | 71.22 | 1.02 | 70.06-71.22 |
| 7 | 7 | 24 | 4 | HGT | 9.62 | 21.58 | 0 | 71.22 | 1.95 | 70.06-71.22 |
| 8 | 8 | 17 | 7 | HGT | 10.38 | 16.55 | 0 | 81.65 | −1.28 | 74.75-90.17 |
| 8 | 8 | 17 | 8 | HGT | 4.68 | 11.88 | 0.00002 | 90.03 | −1.06 | 74.75-90.17 |
| 8 | 8 | 17 | 9 | HGT | 3.96 | 8.76 | 0.00011 | 90.03 | −0.83 | 77.69-90.17 |
| 8 | 8 | 17 | combined | HGT | 16.18 | 11.1 | 0 | 90.03 | −0.97 | 81.65-90.17 |
| 9 | 9 | 25 | 10 | HGT | 4.39 | 8.07 | 0.00004 | 103.64 | −1.45 | 36.89-103.64 |
| 10 | 10 | 26 | combined | LDGSEV | 4.73 | 10.39 | 0.00002 | 74.83 | 0.38 | 71.89-80.27 |
| 10 | 10 | 26 | 11 | LDGSEV | 4 | 10.38 | 0.0001 | 74.83 | 0.38 | 71.89-80.27 |
| 11 | 11 | 27 | 11 | HGT | 11.48 | 13.71 | 0 | 74.68 | 1.75 | 68.03-81.2 |
| 11 | 11 | 27 | 11 | LDGSEV | 8.67 | 11.59 | 0 | 68.03 | −0.48 | 52.47-77.62 |
| 12 | 11 | 18 | 11 | LDGSEV | 4.45 | 14.17 | 0.00004 | 74.68 | −0.46 | 68.03-77.73 |
| 13 | 11 | 19 | combined | HGT | 4.43 | 8.03 | 0.00004 | 77.62 | 1.39 | 71.29-81.2 |
| 13 | 11 | 19 | combined | LDGSEV | 3.74 | 5.73 | 0.00018 | 77.62 | −0.33 | 12.27-81.2 |
| 13 | 11 | 19 | 12 | LDGSEV | 3.96 | 8.36 | 0.00011 | 77.62 | −0.39 | 12.27-89.77 |
| 14 | 12 | 11 | 11 | HGT | 5.71 | 18.06 | 0 | 84.88 | −0.8 | 76.45-97.87 |
| 15 | 13 | 28 | 11 | HGT | 7.94 | 35.64 | 0 | 78.04 | −1.91 | 76.67-78.04 |
| 15 | 13 | 28 | combined | LDGSEV | 7.96 | 18.92 | 0 | 78.04 | 0.48 | 60.51-78.04 |

TABLE 4-continued

QTL mapping on chromosome 13.

| Pop ID | ♀ ID | ♂ ID | Geographic Location | Trait | LOD | VAR | P Value | QTL peak | ADD | CI |
|---|---|---|---|---|---|---|---|---|---|---|
| 15 | 13 | 28 | 12 | LDGSEV | 1.96 | 8.32 | 0.01094 | 76.67 | 0.44 | 67.46-78.04 |
| 15 | 13 | 28 | 11 | LDGSEV | 8.31 | 32.5 | 0 | 78.04 | 0.52 | 76.67-78.04 |
| 16 | 14 | 29 | 13 | HGT | 18.8 | 5.99 | 0 | 79.58 | −2.15 | 76.45-84.88 |
| 17 | 15 | 2 | combined | HGT | 29.51 | 14.88 | 0 | 79.93 | 2.47 | 79.93-80.27 |
| 17 | 15 | 2 | 14 | HGT | 21.5 | 25.46 | 0 | 79.93 | 2.44 | 79.93-87.85 |
| 17 | 15 | 2 | 3 | HGT | 19.77 | 21.72 | 0 | 79.93 | 2.68 | 79.93-87.85 |
| 17 | 15 | 2 | combined | LDGSEV | 8.76 | 5.13 | 0 | 79.93 | −0.46 | 79.93-87.85 |
| 18 | 16 | 30 | 14 | HGT | 5.87 | 16.21 | 0 | 77.17 | −1.13 | 69.73-79.93 |
| 19 | 17 | 27 | 12 | LDGSEV | 5.69 | 10.07 | 0 | 79.48 | −0.43 | 71.17-93.1 |
| 20 | 18 | 31 | 12 | HGT | 2.25 | 5.34 | 0.00568 | 68.88 | −0.94 | 66.66-75.49 |
| 20 | 18 | 31 | combined | HGT | 3.84 | 5.56 | 0.00014 | 75.49 | −0.81 | 66.66-78.68 |
| 20 | 18 | 31 | 11 | HGT | 2.92 | 9.33 | 0.00121 | 75.49 | −0.87 | 71.22-83.57 |
| 21 | 18 | 32 | combined | LDGSEV | 3.45 | 7.31 | 0.00035 | 85.08 | −0.32 | 78.04-97.92 |
| 22 | 19 | 28 | combined | LDGSEV | 3.9 | 6.11 | 0.00013 | 76.45 | 0.38 | 73.98-84.88 |
| 23 | 20 | 8 | 8 | HGT | 7.36 | 11.22 | 0 | 77.24 | 0.99 | 74.08-77.24 |

Pop ID, unique identifier for population produced by the breeding pair
♀ ID, unique female parent identifier
♂ ID, unique male parent identifier
LOD, logarithm (base10) of odds
VAR, percent variance
ADD, additive effect
CI, 95% confidence interval around the identified QTL peak

Example 2: Near Isogenic Lines (NILs)

Near isogenic lines (NIL) were created by deriving single-plant sublines from F3:4 experimental soybean varieties which were heterozygous across the QTL region described in Example 1. Presented here are NILs derived from F3:4 varieties which belong to two families, each having different parents. In the first family, forty individual NILs were homozygous for the male parent allele (parent 2 in FIG. 4, SNP marker allele T of Gm13:36704369) and twenty-seven NILs were homozygous for the female parent allele (parent 1 in FIG. 4, SNP marker allele C of Gm13:36704369). In the second family, eighty-seven individual NILs were homozygous for the male parent allele (parent 4 in FIG. 4, SNP marker allele C of Gm13:36704369) and eighty-seven NILs were homozygous for the female parent allele (parent 3 in FIG. 4, SNP marker allele T of Gm13:36704369). Individual NILs were planted as 5 foot single replicate plots on 36 inch rows in a completely randomized design. Lodging severity data was collected on individual plots. Data was analyzed using the T-Test procedure in Statistical Analysis System software (SAS Institute, Inc., Cary N.C.). FIG. 4 shows significant differences (P<0.0001) in lodging severity for both families. The beneficial alleles (i.e., alleles positively correlating with improved resistance to lodging) from parents 1 and 4 share the same SNP marker allele at Gm13:36704369 (C,C) and Gm13:36300296 (A,A) while the deleterious alleles (i.e., alleles positively correlating with susceptibility to lodging) from parents 2 and 3 share the same SNP marker allele at Gm13:36704369 (T,T) and Gm13:36300296 (C,C).

Therefore, the data from the NILs confirmed the lodging effect. This novel discovery will allow soybean breeding programs to more efficiently select for lodging and height though using this QTL in marker assisted selection. The novel QTL can allow soybean breeders to more efficiently develop soybean varieties with decreased lodging by using marker assisted selection. In addition, the use of these QTLs can permit more accurate phenotyping of soybean varieties.

Example 3: SNP Data

Single nucleotide polymorphisms ("SNPs") were identified that were associated with variation in lodging score. These SNPs can be useful in developing future marker assays for molecular screening. Table 5 shows SNP data for six strains with decreased lodging score and six strains with increased lodging score. A decreased lodging score indicates increased plant lodging, or increased susceptibility to lodging, whereas an increased lodging score indicates plants with improved lodging resistance. "PHYS POS" indicates the physical map position of the SNP based on the Glymal physical assembly (Schmutz et al., 2010). "GEN POS" indicates the genetic map position based on Soybean-Gm Consensus4.0 map (Hyten et al., 2010). Any methodology can be deployed to use this information, including, but not limited to, any one or more of the sequencing or marker methods.

For example, sample tissue from soybean leaves or seeds can be extracted from leaf discs using, e.g., a modification of the CTAB method as described elsewhere herein.

Sample tissue can be screened with markers using a TAQMAN® PCR assay system (Life Technologies, Grand Island, N.Y., USA).

Exemplary TAQMAN® Assay Conditions

Reaction Mixture (Total Volume=5 μl):

| | | |
|---|---|---|
| Genomic DNA (dried) | 16 | ng |
| DDH20 | 2.42 | μl |
| Klearkall Mastermix | 2.5 | μl |
| Forward primer (100 μM) | 0.0375 | μl |
| Reverse primer (100 μM) | 0.0375 | μl |
| Probe 1 (100 μM) | 0.005 | μl |
| Probe 2 (100 μM) | 0.005 | μl |

Reaction Conditions:

94° C. 10 min 1 cycle 40 cycles of the following:

94° C. 30 sec

60° C. 60 sec

Klearkall Mastermix is available from KBioscience Ltd. (Hoddesdon, UK).

TABLE 5

| Marker | PHYS | GEN | Increase in Lodging Score | | | | | | Decrease in Lodging Score | | | | | |
|---|---|---|---|---|---|---|---|---|---|---|---|---|---|---|
| Locus Name | POS | POS | 1 | 2 | 3 | 4 | 5 | 6 | 7 | 8 | 9 | 10 | 11 | 12 |
| Gm13: 36431456 | 36431456 | 77.39 | A | A | A | A | A | A | G | G | | | G | G |
| Gm13: 36490271 | 36490271 | 77.53 | T | T | T | T | T | | C | C | C | C | C | C |
| Gm13: 36491753 | 36491753 | 77.54 | T | T | T | T | T | T | G | G | G | G | G | G |
| Gm13: 36491754 | 36491754 | 77.54 | T | T | T | T | T | T | A | A | A | A | A | A |
| Gm13: 36492037 | 36492037 | 77.54 | T | T | T | T | T | T | C | C | C | C | C | C |
| Gm13: 36492926 | 36492926 | 77.54 | G | G | G | G | | G | C | C | | C | C | C |
| Gm13: 36492955 | 36492955 | 77.54 | A | A | A | A | | A | C | C | | C | C | C |
| Gm13: 36493615 | 36493615 | 77.54 | G | G | G | G | G | G | A | A | | | A | A |
| Gm13: 36494839 | 36494839 | 77.55 | G | G | G | G | G | G | A | A | | | A | A |
| Gm13: 36517239 | 36517239 | 77.6 | A | A | A | A | | | C | C | C | C | C | C |
| Gm13: 36539789 | 36539789 | 77.65 | T | T | T | T | T | T | A | A | | | A | A |
| Gm13: 36539798 | 36539798 | 77.65 | T | T | T | T | T | T | C | C | | | C | C |
| Gm13: 36540415 | 36540415 | 77.66 | C | C | C | C | C | C | T | T | | | T | T |
| Gm13: 36593549 | 36593549 | 77.78 | C | C | C | C | C | C | T | T | T | T | T | T |
| Gm13: 36613902 | 36613902 | 77.83 | T | T | T | T | T | T | | | C | C | C | C |
| Gm13: 36644196 | 36644196 | 77.91 | T | T | T | T | T | T | | | C | C | C | C |
| Gm13: 36644203 | 36644203 | 77.91 | T | T | T | T | T | T | | | C | C | C | C |
| Gm13: 36644207 | 36644207 | 77.91 | T | T | T | T | T | T | | | C | C | C | C |
| Gm13: 36678427 | 36678427 | 77.99 | A | A | A | A | A | A | | | T | T | T | T |
| Gm13: 36697528 | 36697528 | 78.04 | G | G | G | G | G | G | | | A | A | A | A |
| Gm13: 36795108 | 36795108 | 78.27 | T | T | T | T | T | T | | | C | C | C | C |

The marker loci from Table 5 are further described in Table 1, which shows the flanking sequence to the SNP.

Example 4: QTL Mapping for Lodging Resistance

Bi-parental populations were created by crossing two soybean varieties. The F1 seed was grown and bulk generation advanced twice. The F3 seed was planted and individual plants were derived to create a segregating population of F3:4 varieties. The individual varieties were planted and evaluated in field plots.

Bi-parental populations of F3:4 individuals were grown at research locations across the US including Ohio, Illinois, Iowa, and Mississippi. Individual varieties were grown as single replicate 5 foot plots on 36 inch rows. Bi-parental populations were grown at multiple locations within their target environments. Height data was collected at maturity by measuring the average of five plants from the soil level to the top of the mature plants for each plot. Lodging severity was scored visually for each plot using a 1-9 scale representing the percentage of plants in the row at harvest maturity that were less than fully erect. Plots with almost all plants fully erect were scored a 9, plots with most plants at a 45 degree angle in relation to the ground were scored a 5, and plots with almost all plants laying on the ground were scored a 1. QTL mapping was performed on each of the populations and the results are listed in Table 6. Both individual location QTL mapping and combined mapping across locations is presented. In total, eight populations showed significant QTL for height and twenty-three populations showed significant QTL for lodging severity on chromosome 19 in the claimed region at one or a combination of locations. Height and lodging are correlated traits in many environments as taller plants are more prone to lodge.

TABLE 6

| QTL mapping on chromosome 19 | | | | | | | | | | | |
|---|---|---|---|---|---|---|---|---|---|---|---|
| YR | Pop ID | ♀ ID | ♂ ID | Geographic Location | Trait | LOD | VAR | P_Value | QTLPeak | ADD | CI |
| 2013 | 1 | 1 | 6 | 1 | HGT | 15.37 | 31.22 | 0.00000 | 9.42 | 1.50 | 9.42-10.42 |
| 2013 | 2 | 1 | 26 | Combined | HGT | 29.81 | 22.02 | 0.00000 | 9.42 | 1.37 | 9.42-10.42 |
| 2013 | 2 | 1 | 26 | 2 | HGT | 17.96 | 32.30 | 0.00000 | 9.42 | 1.64 | 9.42-10.42 |
| 2013 | 3 | 2 | 1 | 3 | HGT | 18.25 | 32.58 | 0.00000 | 10.04 | −1.75 | 10.04-12.56 |
| 2013 | 3 | 2 | 1 | 4 | HGT | 17.60 | 30.89 | 0.00000 | 10.04 | −1.71 | 10.04-12.56 |
| 2014 | 4 | 3 | 27 | 5 | LDGSEV | 14.24 | 14.96 | 0.00000 | 9.42 | 0.63 | 9.42-10.04 |
| 2014 | 5 | 4 | 27 | Combined | LDGSEV | 14.81 | 7.38 | 0.00000 | 9.42 | 0.49 | 9.42-10.04 |
| 2014 | 6 | 4 | 28 | Combined | LDGSEV | 17.43 | 10.60 | 0.00000 | 8 | 0.66 | 8-14.13 |
| 2014 | 6 | 4 | 28 | 6 | LDGSEV | 14.63 | 14.69 | 0.00000 | 8 | 0.79 | 8-10.04 |
| 2014 | 7 | 5 | 29 | Combined | LDGSEV | 19.38 | 8.74 | 0.00000 | 10.04 | 0.47 | 10.04-10.04 |
| 2014 | 8 | 6 | 27 | Combined | LDGSEV | 23.77 | 6.98 | 0.00000 | 14.57 | 0.69 | 9.42-14.57 |
| 2014 | 9 | 7 | 29 | Combined | LDGSEV | 31.13 | 14.01 | 0.00000 | 10.04 | 0.54 | 10.04-10.04 |
| 2014 | 9 | 7 | 29 | 7 | LDGSEV | 20.72 | 21.35 | 0.00000 | 10.04 | 0.81 | 10.04-10.04 |
| 2014 | 10 | 7 | 30 | Combined | LDGSEV | 39.76 | 17.38 | 0.00000 | 10.04 | 0.68 | 10.04-10.04 |
| 2014 | 10 | 7 | 30 | 6 | LDGSEV | 32.36 | 19.54 | 0.00000 | 10.04 | 0.73 | 10.04-10.04 |
| 2014 | 11 | 8 | 31 | Combined | HGT | 18.01 | 9.16 | 0.00000 | 10.04 | −1.22 | 8-10.04 |
| 2014 | 12 | 9 | 27 | Combined | LDGSEV | 47.69 | 15.10 | 0.00000 | 14.57 | 0.81 | 9.42-14.57 |
| 2014 | 12 | 9 | 27 | 8 | LDGSEV | 20.59 | 15.31 | 0.00000 | 14.57 | 0.95 | 9.42-18.85 |
| 2014 | 13 | 10 | 27 | Combined | LDGSEV | 59.11 | 14.86 | 0.00000 | 9.42 | 0.74 | 9.42-14.57 |
| 2014 | 13 | 10 | 27 | 8 | LDGSEV | 27.50 | 26.08 | 0.00000 | 14.57 | 0.98 | 10.04-14.57 |
| 2014 | 14 | 10 | 28 | Combined | LDGSEV | 24.11 | 8.46 | 0.00000 | 10.04 | 0.47 | 10.04-10.04 |
| 2014 | 14 | 10 | 28 | 6 | LDGSEV | 15.29 | 18.83 | 0.00000 | 10.04 | 0.64 | 10.04-14.85 |
| 2014 | 15 | 10 | 29 | Combined | LDGSEV | 23.65 | 8.80 | 0.00000 | 10.04 | 0.49 | 10.04-10.04 |

TABLE 6-continued

QTL mapping on chromosome 19

| YR | Pop ID | ♀ ID | ♂ ID | Geographic Location | Trait | LOD | VAR | P_Value | QTLPeak | ADD | CI |
|---|---|---|---|---|---|---|---|---|---|---|---|
| 2014 | 15 | 10 | 29 | 6 | LDGSEV | 20.55 | 20.33 | 0.00000 | 10.04 | 0.73 | 10.04-10.04 |
| 2014 | 16 | 11 | 27 | Combined | LDGSEV | 25.28 | 11.99 | 0.00000 | 4.03 | 0.67 | 4.03-10.04 |
| 2014 | 16 | 11 | 27 | 7 | LDGSEV | 17.79 | 18.34 | 0.00000 | 9.42 | 0.87 | 4.03-14.57 |
| 2014 | 17 | 11 | 29 | Combined | LDGSEV | 30.70 | 16.62 | 0.00000 | 10.04 | 0.73 | 10.04-10.04 |
| 2014 | 17 | 11 | 29 | 6 | LDGSEV | 15.77 | 15.65 | 0.00000 | 10.04 | 0.75 | 10.04-10.04 |
| 2014 | 18 | 12 | 29 | 7 | LDGSEV | 16.59 | 14.90 | 0.00000 | 8 | 0.98 | 8-10.04 |
| 2014 | 18 | 12 | 29 | 6 | LDGSEV | 19.88 | 18.95 | 0.00000 | 8 | 0.95 | 8-10.04 |
| 2014 | 19 | 13 | 29 | Combined | LDGSEV | 22.08 | 23.99 | 0.00000 | 9.28 | 0.80 | 4-10.04 |
| 2014 | 19 | 13 | 29 | 7 | LDGSEV | 14.30 | 31.21 | 0.00000 | 9.28 | 0.96 | 4-14.87 |
| 2014 | 20 | 14 | 32 | 9 | HGT | 18.52 | 9.61 | 0.00000 | 14.57 | −1.61 | 10.04-14.57 |
| 2014 | 21 | 15 | 32 | 9 | HGT | 17.37 | 12.06 | 0.00000 | 9.42 | −1.28 | 9.42-14.57 |
| 2014 | 22 | 16 | 32 | Combined | LDGSEV | 19.47 | 8.34 | 0.00000 | 9.42 | 0.19 | 9.42-10.04 |
| 2014 | 22 | 16 | 32 | 10 | LDGSEV | 19.95 | 21.99 | 0.00000 | 9.42 | 0.39 | 9.42-10.04 |
| 2014 | 23 | 17 | 32 | 9 | HGT | 14.98 | 13.64 | 0.00000 | 9.42 | −1.33 | 9.42-14.57 |
| 2014 | 24 | 18 | 32 | Combined | HGT | 18.97 | 9.08 | 0.00000 | 9.42 | −1.19 | 9.42-10.04 |
| 2014 | 24 | 18 | 32 | 9 | HGT | 18.12 | 11.00 | 0.00000 | 9.42 | −1.19 | 9.42-10.04 |
| 2014 | 25 | 19 | 33 | Combined | LDGSEV | 15.84 | 7.03 | 0.00000 | 11.29 | 0.29 | 5.46-11.29 |
| 2014 | 26 | 20 | 34 | Combined | LDGSEV | 22.10 | 9.04 | 0.00000 | 10.04 | 0.26 | 10.04-10.04 |
| 2014 | 26 | 20 | 34 | 11 | LDGSEV | 19.28 | 24.62 | 0.00000 | 10.04 | 0.42 | 10.04-14.85 |
| 2014 | 27 | 21 | 29 | Combined | LDGSEV | 48.32 | 13.49 | 0.00000 | 8 | 0.70 | 8-10.04 |
| 2014 | 27 | 21 | 29 | 6 | LDGSEV | 48.30 | 28.84 | 0.00000 | 8 | 0.91 | 8-10.04 |
| 2014 | 28 | 22 | 29 | Combined | LDGSEV | 22.72 | 13.92 | 0.00000 | 14.13 | 0.72 | 8-14.13 |
| 2014 | 29 | 23 | 29 | Combined | LDGSEV | 24.26 | 12.70 | 0.00000 | 8 | 0.67 | 8-10.04 |
| 2014 | 29 | 23 | 29 | 6 | LDGSEV | 15.50 | 16.08 | 0.00000 | 14.13 | 0.68 | 8-14.13 |
| 2014 | 30 | 24 | 29 | Combined | LDGSEV | 14.08 | 16.25 | 0.00000 | 8 | 0.63 | 8-10.04 |
| 2014 | 31 | 25 | 34 | Combined | LDGSEV | 26.41 | 15.04 | 0.00000 | 10.04 | 0.19 | 10.04-10.04 |
| 2014 | 31 | 25 | 34 | 12 | LDGSEV | 14.17 | 30.99 | 0.00000 | 10.04 | 0.37 | 10.04-14.85 |

Yr, year
Pop ID, unique identifier for population produced by the breeding pair
♀ ID, unique female parent identifier
♂ ID, unique male parent identifier
LOD, logarithm (base10) of odds
VAR, percent variance
ADD, additive effect
CI, 95% confidence interval around the identified QTL peak

Example 5. SNP Data

Biparental populations from 2013 described in Example 4 were further investigated to determine the effect that marker Gm19:1589758 had on plant height. Marker Gm19:1589758 lies within the confidence intervals described in Example 4 and is previously known to be associated with PPO-based herbicide resistance. All biparental populations from 2013 with genotypic data and height phenotypic data were included in the analysis, and heterozygous individuals were dropped from the dataset for the purposes of estimating the marker effect. All data were analyzed using T-tests in R software (see R Core Team, *R: A language and environment for statistical computing*, R Foundation for Statistical Computing, http://www.R-project.org/ (Vienna, Austria), the contents of which are hereby incorporated by reference) to test the difference between the soybean varieties homozygous for the PPO-base herbicide resistance allele (i.e., T, T at Gm19:1589758) and soybean varieties homozygous for the PPO-base herbicide resistance susceptibility (i.e., G, G at Gm19:1589758) allele. Several populations not previously identified in the overall QTL mapping analysis described in Example 1 were shown to have a significant association between marker Gm19:1589758 and plant height (Table 7). In total, Gm19:1589758 was associated with an effect on height in twelve unique populations, with the PPOase herbicide resistance allele (i.e., allele T) positively correlating with increasing height between 1.19 inches and 4.45 inches across populations. Varieties possessing PPOase herbicide resistance alleles at Gm19:1589758 on average have higher plant height and are more susceptible to lodging. Therefore, Gm19:1589758 can be used to identify and/or select plants with decreased height and/or improved resistance to lodging by detecting the PPOase herbicide susceptibility allele (i.e., the G allele).

TABLE 7

| Pop ID | ♀ ID | ♂ ID | Geographic Location | RES AVG | SUS AVG | Difference | HGT_p-value |
|---|---|---|---|---|---|---|---|
| 32 | 35 | 39 | 13 | 34.18 | 30.95 | 3.23 | 0.00012 |
| 1 | 1 | 6 | 1 | 35.07 | 31.94 | 3.13 | 0.00000 |
| 1 | 1 | 6 | 2 | 40.53 | 37.02 | 3.51 | 0.00000 |
| 33 | 1 | 40 | 14 | 44.10 | 42.54 | 1.56 | 0.00027 |
| 33 | 1 | 40 | 15 | 39.19 | 36.63 | 2.57 | 0.00000 |
| 2 | 1 | 26 | 1 | 35.72 | 33.87 | 1.85 | 0.00016 |
| 2 | 1 | 26 | 2 | 42.48 | 39.54 | 2.94 | 0.00000 |
| 2 | 1 | 26 | 3 | 40.54 | 37.81 | 2.74 | 0.00001 |
| 34 | 36 | 41 | 16 | 38.78 | 35.11 | 3.67 | 0.00005 |
| 34 | 36 | 41 | 17 | 40.22 | 35.77 | 4.45 | 0.00000 |
| 35 | 37 | 42 | 18 | 45.89 | 43.35 | 2.54 | 0.00000 |
| 36 | 37 | 14 | 18 | 42.39 | 41.02 | 1.37 | 0.00214 |
| 37 | 37 | 16 | 18 | 42.64 | 40.93 | 1.71 | 0.04346 |
| 38 | 38 | 18 | 18 | 45.61 | 42.56 | 3.05 | 0.00000 |
| 39 | 14 | 36 | 18 | 42.99 | 41.80 | 1.19 | 0.01559 |
| 40 | 16 | 38 | 17 | 39.14 | 36.88 | 2.26 | 0.00066 |
| 3 | 2 | 1 | 3 | 40.32 | 36.63 | 3.69 | 0.00000 |

Pop ID, unique identifier for population produced by the breeding pair
♀ ID, unique female parent identifier
♂ ID, unique male parent identifier
RES AVG, the average height of varieties homozygous for the PPOase herbicide resistance allele at Gm19: 1589758 within a population.
SUS AVG, the average height of varieties homozygous for the PPOase herbicide susceptibility allele at Gm19: 1589758 within a population.
The p-value is the significance of the difference between the marker classes within a population.

Example 6. Genome-Wide Association Study on Height Versus Lodging Severity

A genome-wide association study (GWAS) was conducted to test the association between 3072 genome-wide SNPs and HGT and LDGSEV in order to validate the results presented in Example 4. The phenotypic data set consisted of departmental-wide advanced trial data from the last four years representing 1044 unique elite varieties of indeterminate growth habit. Elite varieties in advanced yield trials are purified homozygous varieties representing both commercial products as well as advanced varieties that are within two years of commercial release. The analysis was conducted using the GAPIT package in R (Lipka et al., 2012). Marker Gm19:1589758 was the most significantly associated SNP with the LDGSEV trait, which is positioned at 10.06 cM on chromosome 19 (Tables 2 and 8). For HGT, three markers associated with a region on chromosome 13 were the top associations with that trait; however, marker Gm19:1589758 is the fourth most associated SNP with HGT (Table 8).

Marker Gm19:1589758, previously known to be associated with PPO-based herbicide tolerance, is also associated with plant height and lodging severity. Varieties possessing PPO resistance alleles at this locus on average have higher plant height and are more susceptible to lodging. This novel discovery will allow soybean breeding programs to more efficiently select for lodging and height though using this QTL in marker assisted selection.

TABLE 8

| Trait | Marker Locus | Chromosome | Position* | P. value |
|---|---|---|---|---|
| LDGSEV | Gm19: 1589758 | 19 | 1589758 | 0.00000 |
| LDGSEV | Gm19: 1635254 | 19 | 1635254 | 0.00000 |
| LDGSEV | Gm19: 1306591 | 19 | 1306591 | 0.00000 |
| LDGSEV | Gm13: 36792347 | 13 | 36792347 | 0.00000 |
| LDGSEV | Gm13: 36864280 | 13 | 36864280 | 0.00003 |
| LDGSEV | Gm19: 841738 | 19 | 841738 | 0.00005 |
| LDGSEV | Gm13: 36704369 | 13 | 36704369 | 0.00007 |
| LDGSEV | Gm13: 36300296 | 13 | 36300296 | 0.06673 |
| HGT | Gm13: 36567042 | 13 | 36567042 | 0.00000 |
| HGT | Gm13: 36704369 | 13 | 36704369 | 0.00000 |
| HGT | Gm13: 36864280 | 13 | 36864280 | 0.00000 |
| HGT | Gm19: 1589758 | 19 | 1589758 | 0.00000 |
| HGT | Gm13: 36792347 | 13 | 36792347 | 0.00000 |
| HGT | Gm19: 1306591 | 19 | 1306591 | 0.00000 |
| HGT | Gm13: 37443784 | 13 | 37443784 | 0.00000 |
| HGT | Gm19: 1635254 | 19 | 1635254 | 0.00001 |

*Physical position (bp) on the Glyma 1 Assembly reference (Schmutz et al., 2010).

That which is claimed:

1. A method of selecting a first soybean plant or soybean germplasm that displays improved lodging resistance, the method comprising:

(a) detecting in a first soybean plant or soybean germplasm at least one allele of one or more marker locus within or linked to a quantitative trait locus (QTL) associated with improved lodging resistance, wherein the allele positively correlates with improved lodging resistance, and wherein the at least one allele of the one or more marker locus comprises an allele selected from the group consisting of allele A of marker locus Gm13:36431456, allele T of marker locus Gm13:36490271, allele T of marker locus Gm13:36491753, allele T of marker locus Gm13:36491754, allele T of marker locus Gm13:36492037, allele G of marker locus Gm13:36492926, allele A of marker locus Gm13:36492955, allele G of marker locus Gm13:36493615, allele G of marker locus Gm13:36494839, allele A of marker locus Gm13:36517239, allele T of marker locus Gm13:36539789, allele T of marker locus Gm13:36539798, allele C of marker locus Gm13:36540415, allele C of marker locus Gm13:36593549, allele T of marker locus Gm13:36613902, allele T of marker locus Gm13:36644196, allele T of marker locus Gm13:36644203, allele T of marker locus Gm13:36644207, allele A of marker locus Gm13:36678427, allele G of marker locus Gm13:36697528, allele T of marker locus Gm13:36795108, allele C of marker locus Gm13:36704369, allele A of marker locus Gm13:36300296, allele T of marker locus Gm13:36567042, allele A of marker locus Gm13:36792347, allele A of marker locus Gm13:36864280, and allele G of marker locus Gm13:37443784;

(b) selecting a first soybean plant or soybean germplasm comprising the at least one allele from step (a), thereby selecting a soybean plant or soybean germplasm that displays improved lodging resistance; and (c) crossing the selected first soybean plant or soybean germplasm with a second soybean plant or soybean germplasm to introgress the QTL into a progeny soybean plant or soybean germplasm.

2. The method of claim 1, wherein the at least one allele comprises allele C of marker locus Gm13:36593549.

3. The method of claim 1, wherein detecting comprises amplifying a nucleic acid sequence comprising the marker locus of each allele and detecting the resulting amplified nucleic acid comprising each marker locus.

4. The method of claim 3, wherein amplifying comprises amplification of at least a portion of one or more genomic regions of the soybean genome selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, and 27.

5. The method of claim 4, wherein the wherein the amplification comprises providing one or more nucleic acid primers, wherein the nucleic acid primers comprise the nucleic acid sequence selected from the group consisting of SEQ ID NOs: 32, 33, 36, 37, 40, 41, 44, 45, 48, 49, 52, 53, 56, and 57.

6. The method of claim 5, wherein the one or more nucleic acid primers comprise a detectable label.

7. The method of claim 1, wherein detecting comprises hybridization with one or more nucleic acid probes, wherein the nucleic acid probes comprise the nucleic acid sequence selected from the group consisting of SEQ ID NOs: 34, 38, 42, 46, 50, 54, and 58.

8. The method of claim 7, wherein the one or more nucleic acid probes comprise a detectable label.

9. The method of claim 1, wherein the marker locus is further associated with decreased height of the plant.

10. The method of claim 1, wherein the second soybean plant or soybean germplasm displays decreased lodging resistance as compared to the first soybean plant or soybean germplasm, and wherein the introgressed soybean plant or soybean germ plasm displays an improved lodging resistance as compared to the second soybean plant or soybean germ plasm.

11. The method of claim 1, wherein the second soybean plant or soybean germ plasm displays increased height as compared to the first soybean plant or soybean germ plasm, and wherein the introgressed soybean plant or soybean germ plasm displays decreased height as compared to the second soybean plant or soybean germplasm.

12. The method of claim 1, further comprising (d) analyzing progeny soybean germplasm to determine the presence of improved lodging resistance; and (e) selecting progeny soybean germplasm that test positive for the presence of improved lodging resistance as being soybean germplasm into which germplasm having said QTL has been introgressed.

13. The method of claim 12, wherein the analyzing progeny soybean germ plasm further comprises determining the presence of decreased height.

* * * * *

SEQUENCE LISTING

```
<160> NUMBER OF SEQ ID NOS: 87

<210> SEQ ID NO 1
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm13:36704369

<400> SEQUENCE: 1

tgctcaataa ttttgtcaca taactgttct tgaataactt atgcctttta caaattccgt      60

cacatacgaa gttgtggcat ttgtgaattg tgatgagaag tggtaaacca ttgctctctc     120

cttgcaatac cttcactatt gtggttgttt ggcttatttc actttttgaa ttgatrttgc     180

atatgattat ttgacatatg ygctgcttgc ttgacaaaac ttgcatatgt ttttgaaatt     240

ttatttcatg agctagggtt ttccattgtt ttgaacaatg ttcatttgtg tgtacatttt     300

attcatttgg ctttatttta caacacaata tatgaagagg atatatgtca actaatttct     360

aattgtatat ttctaatcat tcaggttctt gtggcgccaa a                        401


<210> SEQ ID NO 2
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm13:36300296

<400> SEQUENCE: 2

gattggttac agaaggatag gattgtattg tagtactggg attttcttgt acttgatcca      60

aactttttta agaagctact tttataaatt tccacctttg ttttgcagct agagatctta     120

ttgatacaaa gcacgtggaa gcaataatag gaccccaaac atgggaagag acaactttgg     180

tggctgacat ttgcagccaa macatgacac cggttctatc tctagctgat gcaactccaa     240
```

```
actggtcaac tttgaagtgg ccattccttg tgcaagcctc acctaatcac tttaagcaga    300

tgaaagcagt agcagctatt gttcattcct ttggatggta cgatgttaac atagtttatg    360

atgataggga ttcttcatcc acaagaatgt tatctcatct c                        401


<210> SEQ ID NO 3
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm13:36567042

<400> SEQUENCE: 3

atcttgaggt ttcttcaaac acaatctgtt gtaaagtcat tggtggtctt ctcagctatt     60

ccacttttgg ttcatatttt cattgcataw gccttgattt tctgcacaga tytgagtttt    120

ataggtgctc ctgtagcagt ttctatttca ttatggatat ccataccatt gttggtcatg    180

tatatcatgt atgcagaaag kttcaggcag acttggacag gattttcatt tgagtcattc    240

aattacattt tcacagactt gaaactagct ttgctctcag cagcaatggt atggtatgtc    300

tctaaaaacc ttacacttag ctaaacccct ttgatgattg accttagaaa gttaaatgaa    360

gagcagtttt gtttgaaaat ctgttttctg tttttcattc t                        401


<210> SEQ ID NO 4
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm13:36792347

<400> SEQUENCE: 4

tatggaatct aaatttatta aatatcatta atatggcatg aatgaaatat atttctcatt     60

aatgacaaga ccttttatta aaatatttat tgcattacat aatgtttttt taacgcgttg    120

tgatcaaagt caacatcaat taaatggcca ctgcttttca aaaaaaatta tatgaacgct    180

gacggtttta caaacttatg wgatctatag gcgaaggcta cggtgaacca catattaagt    240

ggttcccagt agaccattat ttctaaccat aggatgtatc ttgttaccat agtatagtcc    300

acactagatc catgcaccct cccagcaact cccttatcca attcctctgg ccaccatttg    360

ccgccactgg aagcaatttt cagcggcagc atttgttttt t                        401


<210> SEQ ID NO 5
<211> LENGTH: 400
<212> TYPE: DNA
<213> ORGANISM: Glycine max
<220> FEATURE:
<221> NAME/KEY: variation
<222> LOCATION: (200)..(200)
<223> OTHER INFORMATION: SNP Gm13:36864280

<400> SEQUENCE: 5

tcaagtgtwa ctaaccacaa ttggaatgaa tataaataat ttgattatgg tcatatacaa     60

agatctaaag ttatattttc aatttattct ccatttataa tttcttaacc tttacggaag    120

cttcgtagtt gttcatatta ctaatcaaat gcatgtgatc ktgtttgaga aatgtcattt    180

tttttaatta gtttaacgtr cgggtggttg ggggaggatc atgtattcat gttacaagtt    240
```

```
aaaattttaa ttttacaata atcaaatagt aatcacttgc caattkatgt tactatgtgg    300

atttaaatgt aagtatttaa tttgctyatg accagtacta tatcattaga cgtttgaaaa    360

aaaaaagtca caaattaaaa aagtatagag aatgctttat                          400


<210> SEQ ID NO 6
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm13:37443784

<400> SEQUENCE: 6

gtttaatttt taaaaaaaaa aactgcctca gattaaaaag tgtttrttat tgttcatcta     60

tctgtaaatt ttccgtcgtc tttgttaaaa gacaaaccat tagagggtac aatgtttgtt    120

ttgatccaaa caaatatacg gcagttggca ttggacggta caattgtttg ttttgatcca    180

aacaaatata tgcaagttgg sagcacctcg tgttactcat aagacacaat cgatcgacag    240

gagagattaa taaccaattc cattaattat tgaacacaaa gtaataaatt ttctttttat    300

ccaatagatt gataaatagt aacaacgtag agtaataaca tataacaatc accttttatt    360

atttattttt aagttaaagg caatatcttc catataagag a                        401


<210> SEQ ID NO 7
<211> LENGTH: 399
<212> TYPE: DNA
<213> ORGANISM: Glycine max
<220> FEATURE:
<221> NAME/KEY: variation
<222> LOCATION: (200)..(200)
<223> OTHER INFORMATION: SNP Gm13:36593549

<400> SEQUENCE: 7

taaatgaata aaaagagaaa aaagatratw tgaaaataat aatataaaaa tttaatataa     60

tawttatttt tcttgaacga cgtgacataa ttaaaataac attatactca agggaccgag    120

caaggacatt ttaacatttg tttcaatgtt tctacatttt tcaatgcaat tgaatgtgat    180

taggacaaga ttggatggay gttaaactgg gttttaaagg aagagagtct aaggtgtgaa    240

actaaaacrt atttgtatgg tgtgaaagga aaaataaatt ttyarcagtt gaatttatta    300

ataaaaaaya taaatggatg agattgattt tcaatttttt atttttattt ttttctattt    360

actttttttc ttcctcccca ttataccctt gtacctttc                           399


<210> SEQ ID NO 8
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36540415

<400> SEQUENCE: 8

taaggatatt ttgcttwaaa aaktaaggat atttaataat tattttaaac cggattaaga     60

attattgaat aaaaaaggta taacacattc actaatgatt yaagtataag acaaatacct    120

cgctacataa taggagatac ttgcataact cgtgtatcta atatggatac agctaggtat    180

ctattaatca tgatggtaat t                                              201
```

```
<210> SEQ ID NO 9
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36490271

<400> SEQUENCE: 9

cgtgttgcat ctcaatgact ttttggccca accctttctt tgctttcggc ttttgaccat     60

gaccaatatg aaattactat attgctcttc aagttgtctt yaacaatact cattaatttc    120

aagatatgat tggtatactg ttgtggtttt caagtatata tgtaaatggg gatctaatgt    180

tttcgtttgt gtctcagaaa g                                              201


<210> SEQ ID NO 10
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36491753

<400> SEQUENCE: 10

gaaatcgttc aaatacattt tcattcaaat taacctaata atataattca acaaaaaaaa     60

watctaacag cattagtgaa gatataagat tgactgaagt kwaaaaaaac taaaaaagag    120

aaatgttaca tgtttcattc gttccgttaa caaaaattaa taatctaaca attaatattt    180

cataataata aaagcctaac a                                              201


<210> SEQ ID NO 11
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36491754

<400> SEQUENCE: 11

aaatcgttca aatacatttt cattcaaatt aacctaataa tataattcaa caaaaaaaaw     60

atctaacagc attagtgaag atataagatt gactgaagtk waaaaaaact aaaaaagaga    120

aatgttacat gtttcattcg ttccgttaac aaaaattaat aatctaacaa ttaatatttc    180

ataataataa aagcctaaca a                                              201


<210> SEQ ID NO 12
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36492037

<400> SEQUENCE: 12

aaaaattata agcattcata attaagtatt tttttttca ttcagtgttg atgcaagaga     60

ataaaagatt ccaaccttta tctgaatatt atagtgtaca ygacatcaaa ggattccttg    120

acaacattga tggcaaaaga tttctttaga cagaaagttt tgatagacat tgatatcatg    180

atatttcaga ttattttcag c                                              201
```

<210> SEQ ID NO 13
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36492926

<400> SEQUENCE: 13
agttgtgttt ggaaacttag aataatgaat gcatctaccg cacaaagcca ccatgggaat 60
acaagtgagg ctatcctagg ataaaaatgg gtaggattga stagaataat atcgtatttg 120
tattcatatm cacatttaaa aaaaaatatt tgtatccgat ttcttatccg tgtgaataat 180
aattttaatt tttattctta t 201

<210> SEQ ID NO 14
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36492955

<400> SEQUENCE: 14
tgcatctacc gcacaaagcc accatgggaa tacaagtgag gctatcctag gataaaaatg 60
ggtaggattg astagaataa tatcgtattt gtattcatat mcacatttaa aaaaaaatat 120
ttgtatccga tttcttatcc gtgtgaataa taattttaat ttttattctt atatctattg 180
aatacttgta tactcatatt c 201

<210> SEQ ID NO 15
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36493615

<400> SEQUENCE: 15
aaataatagg ttaaaagttc taactcttca tccttttaca ttattttatg agataattaa 60
tgaaactatc tagctataag aactaagaag caatgtaatt rcaatactaa taaaaatgca 120
taaarccttt aattggttta aatatagaaa gatcaaatct tatgagtacc ttaaagaata 180
aattatacta ttttttctta t 201

<210> SEQ ID NO 16
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36494839

<400> SEQUENCE: 16
ctcaaactac ttatcttttt tatctttgta agagtactta attatctttt caacttaaat 60
gaggaccata gtttcgaaac acctcaatca tcaagttgat rcttttttttt atcaagcaac 120 attaagtgaa attctattac taaaaaggaa actagcaatg tattgatcag tccttactat 180
tgctttctta ttttgatggt g 201

<210> SEQ ID NO 17
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36539789

<400> SEQUENCE: 17

```
atcaattaaa gccccaattt aagcaatccc catttccact tttaataaaa acaactaaac     60

aaggtatatt ttcaaaagca gcatcatata cttgagagtg wgacatcaay gagagttgtg    120

cataaagttt cttagaagat atttcatatg tttttggggy ggatgactaa aattattcat    180

gtatttttgt tgattacaga c                                              201
```

<210> SEQ ID NO 18
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36539798

<400> SEQUENCE: 18

```
agccccaatt taagcaatcc ccatttccac ttttaataaa aacaactaaa caaggtatat     60

tttcaaaagc agcatcatat acttgagagt gwgacatcaa ygagagttgt gcataaagtt    120

tcttagaaga tatttcatat gtttttgggg yggatgacta aaattattca tgtatttttg    180

ttgattacag acrgtattta a                                              201
```

<210> SEQ ID NO 19
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36697528

<400> SEQUENCE: 19

```
aaaaaaaatc aaatttttgt caatatactt taaaaattca actatatatc aacttgagta     60

aatgaatctt gttgytatga aaaaaaaact aaggrcattg rtagccatga caacaatgat    120

rattatgtta aaaatgatca taatagcgat cacaatgats ratgattata gtaataatct    180

taacatacat caaatattta a                                              201
```

<210> SEQ ID NO 20
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36795108

<400> SEQUENCE: 20

```
gaaacatgaa agcaaatatt atatatttat agtatattct attagctaca tgtgcataga     60

ttctatagaa gttattaaga acatctgctg tggaaaataa ygtaccttgg gtttggatat    120

atcattctct tataaattga tatatctttg ccaatgtaaa tacaccactt cccttcaaaa    180
```

gaacaggaac aaaaacggaa a 201

<210> SEQ ID NO 21
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36431456

<400> SEQUENCE: 21
tacttagcaa aaataggagg tccaaatgag aaataccaaa tttaaatgga tacccaayca 60
atatttgttt tttttttktt aaaatatgtt tttggttttc rtgaaaatgt tcaaaattta 120
tctctacaaa atttttagta tattttttgt cctcacaaat gtgaaatata taatttttta 180
gcacaaatgt aggttaggat a 201

<210> SEQ ID NO 22
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36644196

<400> SEQUENCE: 22
tacaaaactg aaatayttat caaaaggtct ctstggtgtg gtgtggaaat cactgtctts 60
gaagtaaaat ttgrytaaat ctcaatgcaa atttgaaatg ycaaccrytt tycaaggtta 120
acacaatraa cctattaacg cgcactcgtg gtcttaggct gcaattgcca ttgtcaacac 180
aagagggttt tgcttcgggc a 201

<210> SEQ ID NO 23
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36644203

<400> SEQUENCE: 23
ctgaaatayt tatcaaaagg tctctstggt gtggtgtgga aatcactgtc ttsgaagtaa 60
aatttgryta aatctcaatg caaatttgaa atgycaaccr ytttycaagg ttaacacaat 120
raacctatta acgcgcactc gtggtcttag gctgcaattg ccattgtcaa cacaagaggg 180
ttttgcttcg ggcaccagca t 201

<210> SEQ ID NO 24
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36644207

<400> SEQUENCE: 24
aatayttatc aaaaggtctc tstggtgtgg tgtggaaatc actgtcttsg aagtaaaatt 60
tgrytaaatc tcaatgcaaa tttgaaatgy caaccryttt ycaaggttaa cacaatraac 120
ctattaacgc gcactcgtgg tcttaggctg caattgccat tgtcaacaca agagggtttt 180

```
gcttcgggca ccagcatttg c                                            201


<210> SEQ ID NO 25
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36517239

<400> SEQUENCE: 25

caatttttca ttgcataaat gatgcttggc cacaaatgta gaaccattcg tattatacat    60

cagcctgaat tttgtattaa ttgcttgcct tctcttctgg mgaaaagaat cagaatgtcc   120

gtaaagatct tcaccaaaaa atcatgtcca tcatgttgaa ctggttttgg tccccttgct   180

cttcctttta ttctttcgct a                                            201


<210> SEQ ID NO 26
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36678427

<400> SEQUENCE: 26

ttttcaaaaa gtaacgaaca catattagta ttttatattt tattacgatt ctgttaacaa    60

gtatctaaac acatttaatt tatactccca aaaagagtaa waaatttcgt tcttattcat   120

ataactcaac tataagccgt gtttgttact tgagtttgat gtgtcggtta aaattaaatt   180

attttaaaga taaataaaat t                                            201


<210> SEQ ID NO 27
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm13:36613902

<400> SEQUENCE: 27

aatgtaatgt aatgtatttt gcgttgagtt tctccaagtt taagtttaaa ttactcttta    60

awttttttw aaaaaagawt taaatatagt cgctgcattt ycatcagtat tgttcacgag   120

acattccgag taacaaaaaa tattttatta atggatagag tctctttgac aaactttttc   180

acarttattt atattagaag a                                            201


<210> SEQ ID NO 28
<211> LENGTH: 400
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm19:1306591

<400> SEQUENCE: 28

atggctaaac aacgacaacc catgcattcc caamttgtta actgaatatc atgcaactcc    60

gttaggtggt catctgggtg tagctaagac cacccatcgc atcgaatcca atttcttctg   120
```

```
gacaagcctg aaacaggatg ttaaacgttt tgttaaagag tgctcgacat gccagcaaac    180

taagagtatt accaggcgtt yagcaggcyt gctgcagcca ttgycaccrc cgactggggt    240

gtgggaagac ctctcaatgg acttcatcac acacctcccc tttccaatgg cttcacggtt    300

atactcrtcg tagttgatcg atattcaaaa gggrtgcacc tgggtgcctt gcccactggt    360

ttcactgcat tcaaggtcgc caccttgttc ctggmcatta                          400


<210> SEQ ID NO 29
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm19:1635254

<400> SEQUENCE: 29

gtctgagtag tggtgacagt tttgtaaata caaccaacat ttcaacaacg gtttccctga     60

aaatgttatt aaaacctcaa aacgaaaacg gttttcagga aaatcattgt ccttttcgag    120

tattaaaaga tggttttcga gtattcaaac tgtctttgaa tgaaaccaat tttgatgtga    180

aggacttgtg ccccagccct rtctcacttc gttcactccg acatgatcaa cctctttgca    240

cccctctcac tttgtttgtg tcactccgcc tctgtcagtg tcgccattgt agcctgcacc    300

atcgctctgt caccgttgaa gtcgccattg ttgtcatggg ggtcatgagg acatattgtt    360

gttgttkcat mtggtatgcg tctatttcca tttaattcgt t                        401


<210> SEQ ID NO 30
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm19:841738

<400> SEQUENCE: 30

atgcagtgga aatcacaggc ttcacctagt taagtctcac tattttgttg aaggaactga     60

aggtctttca tttgtagttc cacagcttct ttcgatagag gcttgagttc tgaaacatat    120

tcctcatcaa ctcctgctgc tactttctct gccttgtctt tgacaaggyg ccggatctct    180

tcgcgctgaa ctgacgggaa racagcaccg agcattgcag tcagmagtct ctcgtcttct    240

tcctctatgg agtcctttcc aaagcaacac acatagatag catcaagagc cttcccagct    300

cgaatctcca ttgggactgc aggaggatca gcgttttgcc ttgcccgtct ctacagtgtt    360

gaatataatt tttttgagtt gttagggtac tagggtagtg t                        401


<210> SEQ ID NO 31
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP Gm19:1589758

<400> SEQUENCE: 31

tgcgagcaac cttcgaaayg agggaagtgg tggcttgtta tcttccacta cttcttcaac     60

aatattgtta tcgtcaccac caccaatacg aggtatcgag ttggtggagc tagaacggmt    120

catcacaaca gagagcctac ggctactcgt gttgtgattg tctttgttcg atatggacga    180
```

aggaggagta ggatgaaaaa kggtgtcttc tttttcattt tttgcttgtt ggagacgaac 240
tagtgaggtg taaaggccat tgtcgttttg gattagttca tggtgtgatc ccatctccat 300
gattttccca ctttgcacaa cagcaatcac atttgcattc cttatggtgg ataatctatg 360
tgcaatgatg attgttgtgc gccctactgc trctttgtct a 401

<210> SEQ ID NO 32
<211> LENGTH: 26
<212> TYPE: DNA
<213> ORGANISM: Artificial Sequence
<220> FEATURE:
<223> OTHER INFORMATION: Oligonucleotide Primer/Probe

<400> SEQUENCE: 32
tcaaaacaat ggaaaaccct agctca 26

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide Primer/Probe

<400> SEQUENCE: 33
ccattgctct ctccttgcaa tacc 24

<210> SEQ ID NO 34
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 34
caagcagcgc atat 14

<210> SEQ ID NO 35
<211> LENGTH: 15
<212> TYPE: DNA
<213> ORGANISM: Artificial Sequence
<220> FEATURE:
<223> OTHER INFORMATION: Oligonucleotide Primer/Probe

<400> SEQUENCE: 35
caagcagcac atatg 15

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 36
cccaaacatg ggaagagaca 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 37
cagtttggag ttgcatcagc 20

<210> SEQ ID NO 38
<211> LENGTH: 15
<212> TYPE: DNA
<213> ORGANISM: Artificial Sequence
<220> FEATURE:
<223> OTHER INFORMATION: Oligonucleotide Primer/Probe

<400> SEQUENCE: 38
ttgcagccaa cacat 15

<210> SEQ ID NO 39
<211> LENGTH: 13
<212> TYPE: DNA
<213> ORGANISM: Artificial Sequence
<220> FEATURE:
<223> OTHER INFORMATION: Oligonucleotide Primer/Probe

<400> SEQUENCE: 39
cagccaaaac atg 13

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 40
tgactcaaat gaaaatcctg tcc 23

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide Primer/Probe

<400> SEQUENCE: 41
aggtgctcct gtagcagttt ct 22

<210> SEQ ID NO 42
<211> LENGTH: 13
<212> TYPE: DNA
<213> ORGANISM: Artificial Sequence
<220> FEATURE:
<223> OTHER INFORMATION: Oligonucleotide Primer/Probe

<400> SEQUENCE: 42
ctgcctgaac ctt 13

<210> SEQ ID NO 43
<211> LENGTH: 13
<212> TYPE: DNA
<213> ORGANISM: Artificial Sequence
<220> FEATURE:
<223> OTHER INFORMATION: Oligonucleotide Primer/Probe

<400> SEQUENCE: 43
ctgcctgaaa ctt 13

<210> SEQ ID NO 44
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 44
ttaatatgtg gttcaccgta gcc 23

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 45
acgcgttgtg atcaaagtca 20

<210> SEQ ID NO 46
<211> LENGTH: 19
<212> TYPE: DNA
<213> ORGANISM: Artificial Sequence
<220> FEATURE:
<223> OTHER INFORMATION: Oligonucleotide Primer/Probe

<400> SEQUENCE: 46
cctatagatc acataagtt 19

<210> SEQ ID NO 47
<211> LENGTH: 19
<212> TYPE: DNA
<213> ORGANISM: Artificial Sequence
<220> FEATURE:
<223> OTHER INFORMATION: Oligonucleotide Primer/Probe

<400> SEQUENCE: 47
cctatagatc tcataagtt 19

<210> SEQ ID NO 48
<211> LENGTH: 25
<212> TYPE: DNA
<213> ORGANISM: Artificial Sequence
<220> FEATURE:
<223> OTHER INFORMATION: Oligonucleotide Primer/Probe

<400> SEQUENCE: 48
caattggcaa gtgattacta tttga 25

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 49
cggaagcttc gtagttgttc a 21

<210> SEQ ID NO 50
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 50
accacccgca cgtt 14

<210> SEQ ID NO 51
<211> LENGTH: 15
<212> TYPE: DNA
<213> ORGANISM: Artificial Sequence
<220> FEATURE:
<223> OTHER INFORMATION: Oligonucleotide Primer/Probe

<400> SEQUENCE: 51
ccacccgtac gttaa 15

<210> SEQ ID NO 52
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 52
aatatacggc agttggcatt g 21

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 53
tcctgtcgat cgattgtgtc 20

<210> SEQ ID NO 54
<211> LENGTH: 15
<212> TYPE: DNA
<213> ORGANISM: Artificial Sequence
<220> FEATURE:
<223> OTHER INFORMATION: Oligonucleotide Primer/Probe

<400> SEQUENCE: 54
caagttggga gcacc 15

<210> SEQ ID NO 55
<211> LENGTH: 15
<212> TYPE: DNA
<213> ORGANISM: Artificial Sequence
<220> FEATURE:
<223> OTHER INFORMATION: Oligonucleotide Primer/Probe

<400> SEQUENCE: 55
caagttggca gcacc 15

<210> SEQ ID NO 56
<211> LENGTH: 30
<212> TYPE: DNA
<213> ORGANISM: Artificial Sequence
<220> FEATURE:
<223> OTHER INFORMATION: Oligonucleotide Primer/Probe

<400> SEQUENCE: 56
atgcaattga atgtgattag gacaagattg 30

<210> SEQ ID NO 57
<211> LENGTH: 26
<212> TYPE: DNA
<213> ORGANISM: Artificial Sequence
<220> FEATURE:
<223> OTHER INFORMATION: Oligonucleotide Primer/Probe

<400> SEQUENCE: 57
agtttcacac cttagactct cttcct 26

<210> SEQ ID NO 58
<211> LENGTH: 18
<212> TYPE: DNA
<213> ORGANISM: Artificial Sequence
<220> FEATURE:
<223> OTHER INFORMATION: Oligonucleotide Primer/Probe

<400> SEQUENCE: 58
gatggacgtt aaactggg 18

<210> SEQ ID NO 59
<211> LENGTH: 18
<212> TYPE: DNA
<213> ORGANISM: Artificial Sequence
<220> FEATURE:
<223> OTHER INFORMATION: Oligonucleotide Primer/Probe

<400> SEQUENCE: 59
gatggatgtt aaactggg 18

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 60
ctcgacatgc cagcaaacta 20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 61
ttgagaggtc ttcccacacc 20

<210> SEQ ID NO 62
<211> LENGTH: 16
<212> TYPE: DNA
<213> ORGANISM: Artificial Sequence
<220> FEATURE:
<223> OTHER INFORMATION: Oligonucleotide Primer/Probe

<400> SEQUENCE: 62
attaccaggc gttcag 16

<210> SEQ ID NO 63
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 63
ccaggcgttt agca 14

<210> SEQ ID NO 64

<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 64
gaaaccaatt ttgatgtgaa gga 23

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 65
aagtgagagg ggtgcaaaga 20

<210> SEQ ID NO 66
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 66
agccctgtct cact 14

<210> SEQ ID NO 67
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 67
cagccctatc tcac 14

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 68
ttgctttgga aaggactcca 20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 69
cctcatcaac tcctgctgct 20

<210> SEQ ID NO 70
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 70
ctcggtgctg tctt 14

<210> SEQ ID NO 71
<211> LENGTH: 14
<212> TYPE: DNA
<213> ORGANISM: Artificial Sequence
<220> FEATURE:
<223> OTHER INFORMATION: Oligonucleotide Primer/Probe

<400> SEQUENCE: 71
ctcggtgctg tttt 14

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 72
cgacaatggc ctttacacct 20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 73
tcgatatgga cgaaggagga 20

<210> SEQ ID NO 74
<211> LENGTH: 16
<212> TYPE: DNA
<213> ORGANISM: Artificial Sequence
<220> FEATURE:
<223> OTHER INFORMATION: Oligonucleotide Primer/Probe

<400> SEQUENCE: 74 acacccttt tcatcc 16

<210> SEQ ID NO 75
<211> LENGTH: 16
<212> TYPE: DNA
<213> ORGANISM: Artificial Sequence
<220> FEATURE:
<223> OTHER INFORMATION: Oligonucleotide Primer/Probe

<400> SEQUENCE: 75
acaccatttt tcatcc 16

<210> SEQ ID NO 76
<211> LENGTH: 167
<212> TYPE: DNA
<213> ORGANISM: Glycine max
<220> FEATURE:
<221> NAME/KEY: variation
<222> LOCATION: (94)..(94)
<223> OTHER INFORMATION: SNP Gm13:36704369

<400> SEQUENCE: 76
ccattgctct ctccttgcaa taccttcact attgtggttg tttggcttat ttcacttttt 60
gaattgatrt tgcatatgat tatttgacat atgygctgct tgcttgacaa aacttgcata 120
tgtttttgaa attttatttc atgagctagg gttttccatt gttttga 167

<210> SEQ ID NO 77
<211> LENGTH: 91
<212> TYPE: DNA
<213> ORGANISM: Glycine max
<220> FEATURE:
<221> NAME/KEY: variation
<222> LOCATION: (48)..(48)
<223> OTHER INFORMATION: SNP Gm13:36300296

<400> SEQUENCE: 77
cccaaacatg ggaagagaca actttggtgg ctgacatttg cagccaamac atgacaccgg 60
ttctatctct agctgatgca actccaaact g 91

<210> SEQ ID NO 78
<211> LENGTH: 115
<212> TYPE: DNA
<213> ORGANISM: Glycine max
<220> FEATURE:
<221> NAME/KEY: variation
<222> LOCATION: (79)..(79)
<223> OTHER INFORMATION: SNP Gm13:36567042

<400> SEQUENCE: 78
aggtgctcct gtagcagttt ctatttcatt atggatatcc ataccattgt tggtcatgta 60
tatcatgtat gcagaaagkt tcaggcagac ttggacagga ttttcatttg agtca 115

<210> SEQ ID NO 79
<211> LENGTH: 126
<212> TYPE: DNA
<213> ORGANISM: Glycine max
<220> FEATURE:
<221> NAME/KEY: variation
<222> LOCATION: (89)..(89)
<223> OTHER INFORMATION: SNP Gm13:36792347

<400> SEQUENCE: 79
acgcgttgtg atcaaagtca acatcaatta aatggccact gcttttcaaa aaaaattata 60
tgaacgctga cggttttaca aacttatgwg atctataggc gaaggctacg gtgaaccaca 120
tattaa 126

<210> SEQ ID NO 80
<211> LENGTH: 172
<212> TYPE: DNA
<213> ORGANISM: Glycine max
<220> FEATURE:
<221> NAME/KEY: variation
<222> LOCATION: (86)..(86)
<223> OTHER INFORMATION: SNP Gm13:36864280

<400> SEQUENCE: 80
cggaagcttc gtagttgttc atattactaa tcaaatgcat gtgatcktgt ttgagaaatg 60
tcattttttt taattagttt aacgtrcggg tggttggggg aggatcatgt attcatgtta 120
caagttaaaa ttttaatttt acaataatca aatagtaatc acttgccaat tk 172

<210> SEQ ID NO 81
<211> LENGTH: 110
<212> TYPE: DNA
<213> ORGANISM: Glycine max
<220> FEATURE:
<221> NAME/KEY: variation
<222> LOCATION: (69)..(69)
<223> OTHER INFORMATION: SNP Gm13:37443784

<400> SEQUENCE: 81
aatatacggc agttggcatt ggacggtaca attgtttgtt ttgatccaaa caaatatatg 60
caagttggsa gcacctcgtg ttactcataa gacacaatcg atcgacagga 110

<210> SEQ ID NO 82
<211> LENGTH: 80
<212> TYPE: DNA
<213> ORGANISM: Glycine max
<220> FEATURE:
<221> NAME/KEY: variation
<222> LOCATION: (37)..(37)
<223> OTHER INFORMATION: SNP Gm13:36593549

<400> SEQUENCE: 82
atgcaattga atgtgattag gacaagattg gatggaygtt aaactgggtt ttaaaggaag 60
agagtctaag gtgtgaaact 80

<210> SEQ ID NO 83
<211> LENGTH: 95
<212> TYPE: DNA
<213> ORGANISM: Glycine max
<220> FEATURE:
<221> NAME/KEY: variation
<222> LOCATION: (39)..(39)
<223> OTHER INFORMATION: SNP Gm19:1306591

<400> SEQUENCE: 83
ctcgacatgc cagcaaacta agagtattac caggcgttya gcaggcytgc tgcagccatt 60
gycaccrccg actggggtgt gggaagacct ctcaa 95

<210> SEQ ID NO 84
<211> LENGTH: 91
<212> TYPE: DNA
<213> ORGANISM: Glycine max
<220> FEATURE:
<221> NAME/KEY: variation
<222> LOCATION: (40)..(40)
<223> OTHER INFORMATION: SNP Gm19:1635254

<400> SEQUENCE: 84
gaaaccaatt ttgatgtgaa ggacttgtgc cccagccctr tctcacttcg ttcactccga 60
catgatcaac ctctttgcac ccctctcact t 91

<210> SEQ ID NO 85
<211> LENGTH: 146
<212> TYPE: DNA
<213> ORGANISM: Glycine max
<220> FEATURE:
<221> NAME/KEY: variation
<222> LOCATION: (80)..(80)
<223> OTHER INFORMATION: SNP Gm19:841738

<400> SEQUENCE: 85
cctcatcaac tcctgctgct actttctctg ccttgtcttt gacaaggygc cggatctctt 60
cgcgctgaac tgacgggaar acagcaccga gcattgcagt cagmagtctc tcgtcttctt 120
cctctatgga gtcctttcca aagcaa 146

<210> SEQ ID NO 86
<211> LENGTH: 98
<212> TYPE: DNA
<213> ORGANISM: Glycine max
<220> FEATURE:

<221> NAME/KEY: variation
<222> LOCATION: (34)..(34)
<223> OTHER INFORMATION: SNP Gm19:1589758

<400> SEQUENCE: 86
tcgatatgga cgaaggagga gtaggatgaa aaakggtgtc ttctttttca ttttttgctt 60
gttggagacg aactagtgag gtgtaaaggc cattgtcg 98

<210> SEQ ID NO 87
<211> LENGTH: 8990
<212> TYPE: DNA
<213> ORGANISM: Glycine max

<400> SEQUENCE: 87
tcatcgtctt aggaatcaaa atgaatatta atcttgattg ttttaaaaga caagtaaaat 60
aaattaatgt aacaatccaa cccacgtaac ttcaattaat ttaagttaga ttattgaatg 120
catcacagca acctaatcta ataaatattc ctgttactgt ttactcactt tagacttgtg 180
tgttttttcc tctttataat cttcatctcg tacttttcat ttgtataaat gtttttatat 240
ataaatttaa ctatttattt aaacatgttt agattcgaag aatttgggat ttgttctgta 300
actaagtata ctactggtta ttgctttagg cggcgtgaat atgccggctg cataggatgc 360
catataatac taaagtaata tactaatatc caatttttct gattttattt ttgaaaggtc 420
accaatgtgg ttcaattttt taaataacct ctgctgcgtt taggtgcaaa taataatatt 480
gcaaaamttt attttatttt attttttgta tagtttgaaa ggctaattgg cagattaaga 540
agtggggaat tcccagcatc actaccaaca taaattagga gcgcaggctg attagtggca 600
gtgggcaata ggttattcgg ggaacaataa ggttttatct ttatggggaa aaataaatat 660
ttaactatgg tgaactattg catacatttt gtcctatata taaagcatct ttgtttgaaa 720
ggacacttca tggctaactt attttgaatt aaaaatttat atattggcat actttgcttt 780
tcattgycaa aaagaatttt ttgatgagtt gcttatattt aactacatag ttaaattaaa 840
cgagtatttt atgcaattga tttaagaatc aaacttgtta catttccaca agaacaaaaa 900
tgagtcttta atagtttttt atatatagaa gaaaaagaaa agacaaaata gaaagaagaa 960
actagatcct aatgagtcaa actcattttg ttggtaaaaa aaaggctcta attgtagtgg 1020
gtaaacattc caaacaaaga aagagtcttc atgcattgca ttatgtttag caagcagcta 1080
gagaatattt tgaatgacaa gaakatgagg ttggtagtga caccacatga gagtatgctg 1140
agatgaagtt gcttagctga tttcagatga tgactcttta atagtawaaa atgttttaac 1200
aacaacaata catttaagtt ttaagcctct aaagaataaa taatattttt attaatagta 1260
gtcttacaca atatcattaa atagtaaatc atgtatggay caacatgttg gcattagtgr 1320
agttagatac taattttta aggtttcata tttaaatttt gtagctaaaa aratgtgatt 1380
aggaggaaaa attatactcc tatttggtaa cgagaaaaaa aaaggagtga ttgtgttgga 1440
atacaagtgt gaggtgaaat cttacatcgt atatgaatga aaatgttgag caagtgaagg 1500
caacactcac aaacttgagt ttcaaaattt taggttaaag tgtggtgttt gattcactta 1560
tgtggtttca caatacccat trgtgcaaat ctcttcattg tttacctctt csrttgcaaa 1620
acaattgata taagagttta ttgtttgact tggtgatcga ctcggatgag taagatgacg 1680
gtggtggatt ctaggcctgg agatyccttg tgtcgaaagt tttcctarta gtgggtccaa 1740
gcggcatgtc ccattgatgg rgtggcgtgt ctcgtcggtg caagtatcta gagcacgtag 1800
actaatggtc accatgaaaa tactcgtaaa tgataatgac ttccacttga ggagaaagct 1860

```
accatawaga tgaaactcat acttagggat gtcaatgggg tggggcgggg agtactccct   1920
cgccccccaa gtaacccctc atccccatcc tcgatttcta tcatggggga tttttttttcc  1980
actatccccg ttctcgtgga ccttgaaatt ttataaaaaa aaatattaat tttaaattct   2040
aatacaagta aatttaaaaa agacttaaaa agcctcacaa cataatacty aaactcaaat   2100
aatycatata ttgttaaact caaataaaca aacatggaca acaagtttaa tttgaaataa   2160
tacaagcata atgttcaata acaatacaaa tagttaaaac tacaaatatt tttttgcaat   2220
attttcaaca atcctacaat atttaaaata taaaatamwa ttatataagg gaattatgta   2280
atttcytcag ggcaggaccc tacgatgagg gaggggggt gatcctcatc cccgccatgc    2340
ccttgaaaga atatttatcc ctgtcccyat aggggaaaaa tccccgtctg yagggtccca   2400
tacaagatag tccctgtggg gatycttgtt tacgcgtcca aattgacacc tctactcaca   2460
cttgcggggg agattgttgg aatataagtg tgaagtgaag tcgcatatcg tgtaggaatg   2520
aaaatgttga gcaycgtata agtaaagaca atagacccat aaatctgagt cttaaggttt   2580
tcagttagat tgtactgtca agttcactta tgtagttgct cgaggctcat tggtgtaaat   2640
cttttaagtg taaatatttt aagtgtttac cccctcggtt gcacaacatt tgatattaga   2700
gacgatggtt tgacttagtg accggttcag agggtaagat aacgacggtg gatcctaggt   2760
ctggagatcc tttrtatcga aagtcttctt tgtgatgggt ccaggtgagg tgtctcggac   2820
taccatgtga atgagactca gacttgaggg agagattgtt agaatacaag tgtgaggtga   2880
agtttgatat tgtgtaagaa tgagaatatt gagcatcata taagtaaaga caaaatccat   2940
aaaattgaay ttaaggtttt ggattaaaat atgatgtcaa gttcacttat atgattactc   3000
atgacccata agtataaatc tctctggtgt ttactctcct tycttgattg taaatataat   3060
gaatgagtga aaataaataa aaaataaaga agatgtaaag agacttcagc agcatagaag   3120
cattgcaaat taaatagatt taatgactag agcataaaaa aaawttatgt atggagtaaa   3180
atataaaaat tagatatgaa gtcttaaatg caaagtgtaa ataagtgtag gaaaaataat   3240
taatggaact taaaataaat tattaattaa atattattta aaatggtgtt caagtaaata   3300
tagttgagtc taattataga tttgagcata agtttgtgca caatgttgaa tcgcttgtac   3360
gattggtatt atttgtttaa ctgatacatg aaatgggtta aggacacgac acaatttaat   3420
tgtatagtct aattaaataa ttacatctca aaggttaagc cgttaagaac acaacacgag   3480
ttacattgtc attatattct tagaaatggg tcctcctcta taacgattag tgataaatgg   3540
atataaatta taaacctgtt aaacaatgtc aaaggatctt atagtctctt tatcttgtta   3600
atttatgggg aaaaaaggac atgtttcgtt ctttcatcag ttctttattt taaaattaat   3660
ttgttttata caaaatttta tactattcag cgatcaaatg ttcatttaaa atctattaat   3720
ttaatttttc tttgtaactt gtaggcttac accactgtct acccgttgtc tgaacaccct   3780
gtttaattgt atttttaaaa aacaattttt ttttttgaaa ataaaaacca aacatatact   3840
cagtaagatt agttttggta tttattttgt tgtgctgctt atttaattaa aactgaactt   3900
taactttwag aacttatatt aaattttaat gttgactttc attgtacaag tttctgcaac   3960
taaaatttta attttaataa aaagaacact taaaatattg tacctatatt ttgtgacaat   4020
taattaaata gataactgat atccgttcat tcatacttga ttagttgaat agcatatgct   4080
ctttttttaaa attctgacaa tttcattaaa tcgactttta tcgacaacca agtagttaag  4140
atacccaata acatatgaac aacaatgctt cwatcgcttt tatatatgtg tgtgtatttc   4200
```

```
ccaagaatat tgcgaagaga ttatgagact ccatttgaaa aggttagcct caaaaaataa   4260
tttcaatatt tatttttct tttatgtcat tcaattccat gctcacattc ttttcaataa   4320
tttaaattca tttatatgtc attcaatata ttctcatgta tgattccctc tttaaaaaaa   4380
aaactgataa gttttgttga gttttgtaat gattgtttta aaatacatat ttaatatttt   4440
ttatattctg tatatcattt ttgtcggtga ttgtcatgaa ataagaataa aatccacctc   4500
ctttactgtc tatttagttt aagagaaata ttgttcagta taaaaacact tttcgtcatt   4560
tttacccgaa tgatgatttt attcaaatta tattttttat ttttaaatca atatttgaca   4620
atartgaaaa caaaggataa acattcccca ttaagctttc ttctcatttt atgtgtaaaa   4680
tgtaaataat tcgtaccaaa tatcaacgtt cttagtttat aggaaaggaa ctgaagaaat   4740
agagataaaa attaaattga aaaataaawa acaggagagc catatttaaa ttgttgtttt   4800
taaaataaaa ttttctctct gtcttttatt tctatttcaa tctaataaga aaaacatcat   4860
tattaatatt ttgccttacg tttttcttg tctctcactg ttacacatca cgaatgagaa    4920
ttacaataat tttattctat taaagagtat gtattaaaaa agtatgtgaa aatttatcaa   4980
tgaattgaat tgtctattat tcctgttaca acatcaacgc gtgatgcatt aggaattagt   5040
aaatgcataa acgtttagct tcttcattca atagggcttt ttgaagtata gagcactaaa   5100
ttgtaatttt attttcttta atttctgatg taggatttcg gtttttctat tttaattttt   5160
ttattttaat ctaatgttta ataaacgttt ttaatatttt tttaattaat taaaatgttt   5220
tttatggtag cttaatggag tatgttaaat ctagagctca attcatcaaa atgaaagata   5280
aaatacatac caatttgagg tttggacttt ggacaaaaaa atcagggttt atattttcaa   5340
aatagagctc gaacaaaaat tgtaaagaaa aawcttagtt gaatcttatt ttaatcattt   5400
aaagaaaaaa taaaatatag acttcttaac caacgagttt aactagttgt ttagttgagc   5460
aattaggtga attatcattt tatatctcct tatatttgtt tgtgtttgat ttgtatgact   5520
aaaattatat actttcattg tttttaataa tattatctaa aaaaaatwkt tttattattt   5580
gagattctat ttttaatgtg tcattttttt attattaata tcagatttta atgaaagtta   5640
ctaatttaga agaaaaaaat ttcttaaatg caaatagtaa aattaacgat ataaaccgat   5700
ttgtttaatt aacataaaaa ttgattaatt ttaattaaat ttaagtttgg agtagtatac   5760
tctstctatt caattttata agatagttta agattttgat acaagtatta acaaatacaa   5820
ttaatatttt aaatttcata aaaaatatta tgatttttta atatgtcttt tattttttta   5880
attaattaga tttattatta ttattataca atgacaacta ctcctgttaa ggacactcca   5940
taacaaaata tagttaatgt tttatttgtt ttctaaaatc acaactaatg taaaatatat   6000
ttttaatgtc ttataaagaa caatggggga gtatttctat aaataaataa aaaaaaacgg   6060
gggagtatta tttaaaagaa tgcacctgga caaattttag gcagccagca aaatcatatt   6120
tgcaaataaa aaattgattg attgttactc cgttggcaag atgttattct ttcattattg   6180
aaccaatggg gattgatttt tataatttaa aaaagttgtt aaaaaaatga ggcatcacag   6240
agttggaaaa ggcgaagaag aaagaaagag tgggaaaagg tggagacaca agaaagatgg   6300
gggcgcagaa acatcacgtg aagacaacat gaactccgac agccacatag tcaacacaga   6360
atgccccacg tgggccccac tcmcccgctt ctgattcgct ctccctttct acgcagcgtt   6420
ttcgccgtcg gtgccgcctg cgctgcaata aaayattagt taattaaatc ccaaacttga   6480
ttacaataaa taaataaata ttaccctcca cgaagcacaa gaatagtgaa ccaaaawaac   6540
aaacgaatga atgcgtccct tccactcgca ctcatagcca ttgagatccg cgccgcaacg   6600
```

```
cgaatcacga ggacaccctc tcatcttatc tagtacccac gctactcatc atcaacctga   6660
aaaacccctt tctctctctc tctcaaataa tgctttaata aatcgaatca gattcactgg   6720
ttacacagag taaaaattta gaatcgaccc tatctttaaa acattgtcta gtttattcgt   6780
aattcaattg caacgtaaaa ccacttaaac ctgacttaac tctcactagt tcagttttgc   6840
tttcagttat aaaaaaattg caaccaagtg gggcccacgg tgacaccacg aaacaataca   6900
aagttgtttc cttttgtcat tttaattttt taggtgaaag tattttaatt tcagtatagg   6960
gttaatagca acgcttgcct agccaaatgt ctagcatagg gataaagaac aaaccaatca   7020
agtaatatgt ggagagagga agaggcccca ccacaaaaac ctaatcaaac gcgcaacaat   7080
gccggcgaca tgtctgtcag atctcaacya accaaatcca acagcggtta gattaatcgg   7140
aaaacgcaca aatatggcaa aactctaaat ggataacgtt agagataccg atgtttcttg   7200
cgcgcaaaac ctaacacaaa caaatagaag ctaaaaagat agagagaaaa tgagaaacct   7260
aaagattaat aataacacat gatggaaatt ggaatattta tatattttga gaaattgcag   7320
aaacaaccat gagatactct gaataagagt cctcagttgc aaaaaaaaaa agcaaccaag   7380
caaaagcacg tttgctttcg gttataacgt gtatttacat aacgtgccgg ttatatatct   7440
tcatcatcac aaaatggtca acaaatccga gcatcatgtc atccactact cactttgctg   7500
ctccctcgag ggcactttcg tcaaaaaatg cgtagtagta cctcccagat gcttaaaaaa   7560
ccaaaaaaac aataattgca aaaaacagaa ctccctgcat gaatcaggca acctccggga   7620
gaggaggyac gttcaggtca agatccagga gtatgcggcg gttataatca gagtcggagt   7680
cgccgcggcg gaaatcggcg gcggggcgtt cgaagccgca ggtctcgcgg cgcgagacgg   7740
cgaccatggt gtccgcacgc gcgaatgcgt cgaagaatag aacaggacgc gccaccggga   7800
agacagcgga ggagagaggg gtgagggtaa ggtctagcgg tggcggtggc gggggagagg   7860
atgagtcgag ggtgctggtc tggctgggac tacgagcgtt tatgttgttr ttgttaagga   7920
tgagttccga gggtgtcggg aaattggtct tggccttggc gccacgaaac tcacgcgcgg   7980
cggtgtcgta ggcgcgcgcg gcttcctcgg cggtgtcgaa agtgccgagc cagacgcggg   8040
ttttcttgcc gggatcgcgg atctcggcgg cgtagcggcc ccaggggcgt ttcctgacgc   8100
ctctgtagcg gatctctttg tgggccggtg ataggcttgg gccgggccca atgagcgcgg   8160
tggctcggct gtctcttgga gccattagcg ttatttttcc tttggattca aatctttctc   8220
aacggggagc agaaaagtta tgagaggagt aagaagcgtg tgggattgag acaatgtctg   8280
agggggaaca agcgtgttgg actggtttta tagccctcta tggagagaga gagaaaccac   8340
accgtgggcg tgcgtcttta atgttacgct cctcacgcgc gtgtttccca ctcaatgtgg   8400
cttcccttac acgaaccttg cgtctttatt gttttctttt gcattacttg ccaagattgt   8460
tttttcttc ttctttactt accttgattt tcttctgtag tagtataaaa tgaggaaatt   8520
ttgactttag cttttattta ttacttattt ttctctataa aattcaaatt actattatta   8580
tatataaaat aagtggattt ttttattcta ataattttta aaaatttctc ttccttcata   8640
atattttttt tatatacagt atttatttta agaattgaca amaaaaaatt gatgaaagta   8700
tcgtatacta acagtctaac atgatattca aacactagat ggatattaag agaaatattt   8760
tcttgacttt ttattaaaca gttaacaaat actgtatagg acaaaagata ctaaaacaat   8820
```

-continued

```
gattttataa atttgaagaa tgaaaatcca agaaacattg atctgttaaa atactttaaa   8880

taaagaacag attttcatta attattacta cacaccaaaa tcctaaataa gtaaaaataa   8940

tcgacacgta cttatctgaa atttttgctg aatgaaatga attaacagaa              8990
```